US010086068B2

(12) United States Patent
Walser et al.

(10) Patent No.: US 10,086,068 B2
(45) Date of Patent: *Oct. 2, 2018

(54) PEANUT FORMULATIONS AND USES THEREOF

(71) Applicant: Aimmune Therapeutics, Inc., Brisbane, CA (US)

(72) Inventors: Bryan Walser, Menlo Park, CA (US); Howard V. Raff, Mill Valley, CA (US)

(73) Assignee: Aimmune Therapeutics, Inc., Brisbane, CA (US)

( * ) Notice: Subject to any disclaimer, the term of this patent is extended or adjusted under 35 U.S.C. 154(b) by 18 days.

This patent is subject to a terminal disclaimer.

(21) Appl. No.: 15/276,440

(22) Filed: Sep. 26, 2016

(65) Prior Publication Data

US 2017/0021012 A1    Jan. 26, 2017

Related U.S. Application Data

(63) Continuation of application No. 14/207,127, filed on Mar. 12, 2014, now Pat. No. 9,492,535.

(60) Provisional application No. 61/784,863, filed on Mar. 14, 2013.

(51) Int. Cl.
| *A61K 39/35* | (2006.01) |
| *A61K 39/36* | (2006.01) |
| *A61K 39/00* | (2006.01) |
| *A61K 39/38* | (2006.01) |
| *C07K 1/00* | (2006.01) |
| *C07K 14/00* | (2006.01) |
| *C07K 17/00* | (2006.01) |
| *G01N 33/68* | (2006.01) |
| *A23L 33/185* | (2016.01) |
| *A23L 25/00* | (2016.01) |
| *G01N 33/483* | (2006.01) |

(52) U.S. Cl.
CPC ............ *A61K 39/35* (2013.01); *A23L 25/30* (2016.08); *A23L 33/185* (2016.08); *G01N 33/483* (2013.01); *G01N 33/6893* (2013.01); *A23V 2002/00* (2013.01); *A61K 2039/542* (2013.01); *A61K 2039/577* (2013.01); *G01N 2500/20* (2013.01); *G01N 2800/24* (2013.01)

(58) Field of Classification Search
None
See application file for complete search history.

(56) References Cited

U.S. PATENT DOCUMENTS

| 3,809,767 | A | 5/1974 | Sair |
| 9,198,869 | B2 | 12/2015 | Walser et al. |
| 9,492,535 | B2 * | 11/2016 | Walser ............... G01N 33/6893 |
| 2002/0018778 | A1 | 2/2002 | Caplan |
| 2004/0234548 | A1 | 11/2004 | Caplan |
| 2008/0031787 | A1 | 12/2008 | Li et al. |
| 2012/0164306 | A1 | 6/2012 | Girsh |
| 2013/0090344 | A1 | 4/2013 | Thakur et al. |
| 2014/0093541 | A1 | 4/2014 | Clark et al. |
| 2014/0207105 | A1 | 7/2014 | Laulicht et al. |
| 2014/0363470 | A1 | 12/2014 | Koppelman et al. |
| 2016/0030289 | A1 | 2/2016 | Walser et al. |
| 2016/0051593 | A1 | 2/2016 | Raff et al. |
| 2018/0042816 | A1 | 2/2018 | Walser et al. |

FOREIGN PATENT DOCUMENTS

| JP | 2014-509606 A | 4/2014 |
| WO | 1992015285 A1 | 9/1992 |
| WO | 2010069595 A1 | 6/2010 |
| WO | 2012001074 A1 | 1/2012 |
| WO | 2012123759 A1 | 9/2012 |
| WO | WO-2013/087119 A1 | 6/2013 |
| WO | 2014159609 A1 | 10/2014 |

OTHER PUBLICATIONS

U.S. Appl. No. 14/207,127, Non-Final Office Action, dated Nov. 6, 2015, 8 pages.
U.S. Appl. No. 14/207,127, Notice of Allowance, dated Aug. 11, 2016, 8 pages.
PCT/US2014/024401, International Search Report, dated Jul. 21, 2014.
PCT/US2014/024405, International Search Report, dated Aug. 18, 2014.
Anagnostou, K. et al. Assessing the efficacy of oral immunotherapy for the desensitization of peanut allergy in children (STOP II: A phase 2 randomized controlled trial. *The Lancet*, v. 383(9925) pp. 1297-1304 (2014).
Bernard, H. et al. Identification of a new natural Ara h 6 isoform and of its proteolytic product as major allergens in peanut, *J. of Agricultural and Food Chem.*, v 55(23), pp. 9663-9669 (2007).
Boyce, J.A., et al, Guidelines for the diagnosis and management of food allergy in the United States: Report of the DIAID-sponsored expert panel. *J. Allergy and Clincal Immunology*, v. 126(6), pp. S1-S58 (2010).
Chen, X., et al. Ara h2 and Ara h6 have similar allergenic activity and are substantially redundant. *International Archives of Allergy and Immunology*, v 160, pp. 251-258 (2013).
Clark A.T. et al. Successful oral tolerance induction in severe peanut allergy. *Allergy*, v 64, pp. 1218-1220 (2009).
Flinterman, A.E. et al. Children with peanut allergy recognize predominantly Ara h2 and Ara h6, which remains stable over time. *Clin. Exp. Allergy*, v 37, pp. 1221-1228 (2007).
Jones, S.M. et al., State of the art on food allergen immunotherapy: Oral, sublingual, and epicutaneous. *J. Allergy and Clinical Immunology*, v 133(2) pp. 318-323 (2014).

(Continued)

*Primary Examiner* — Nora M Rooney
(74) *Attorney, Agent, or Firm* — Morrison & Foerster, LLP

(57) ABSTRACT

The present application relates to compositions for oral immunotherapy of peanut allergies. Further, the present application relates to methods for the preparation of the compositions for immunotherapy, and their use in immunotherapy.

38 Claims, 21 Drawing Sheets

(56) References Cited

OTHER PUBLICATIONS

Koid, A., et al. Purified Natural Ara h6: an important Marker for IgE response to peanut. *J. Immunology*, v. 188, pp. 177.15 Meeting Abstract Supplemental (2012).

Koppelman, S.J. et al. Digestion of peanut allergens Ara h1, Ara h2, Ara h3, and Ara h6: A comparative in vitro study and partial characterization of digestion-resistant peptides. *Molecular Nutrition and Food Research*, v. 54, pp. 1711-1721 (2010).

Koppelman, S.J., et al. Quantification of major peanut allergens Ara h1 and Ara h2 in the peanut varieties Runner, Spanish, Virginia, and Valencia, bred in different parts of the world. *Allergy*, v 56, pp. 132-137 (2001).

Koppelman, S.J., et al. Relevance of Ara h1, Ara h2, and Ara h3 in Peanut Allergic Patients, as Determined by Immunoglobulin E Western Blotting, Basophil-Histamine Release, and Intracutaneous testing: Ara h2 is the Most Important Peanut Allergen. *Clin. Exp. Allergy*, v 34, pp. 583-590 (2004).

Morishita, M. et al., Is the oral route possible for peptide and protein drug delivery? *Drug Discovery Today*, v. 11(19/20), pp. 905-910 (2006).

Muheem, A. et al. A review on the strategies for oral delivery of proteins and peptides and their clinical perspectives. *Saudi Pharmaceutical Journal* (2014).

Pele, M. Peanut allergens. *Romanian Biotechnological Letters*, v 15(2), pp. 5204-5212 (2010).

Porterfield, H.S. et al. Effector activity of peanut allergens: A critical role for Ara h2, Ara h6 and their variants. *Clin. Exp. Allergy*, v 39(7), pp. 1099-1108 (2009).

Sicherer, S.H. et al., Food allergy: Epidemiology, pathogenesis, diagnosis, and treatment. *J. Allergy and Clinical Immunology*, v 133(2), pp. 291-307, 307.e1-307.e5 (2014).

Singh, H. et al. Developing RP-HPLC method for detection of peanut allergens. [online] AACC International Annual Meeting, Oct. 16-19, 2011 [Retrieved on Feb. 17, 2016]. Retrieved from the Internet: <URL: http://www.aaccnet.org/meetings/Documents/2011Abstracts/p11ma199.htm>.

Varshney, P. et al., A randomized controlled study of peanut oral immunotherapy: Clinical desensitization and modulation of the allergic response. *J. Allergy and Clinical Immunology*, v 127(3) pp. 654-660 (2011).

Wang, J. et al. Food Allergy, *J. Clinical Investigations*, v 121(3), pp. 827-835 (2011).

Altschul, A.S. et al. (Sep. 2001). "Manufacturing and Labeling Issues For Commercial Products: Relevance to Food Allergy," *J. Allergy Clin. Immunol.* 108(3):468.

Blumchen, K. et al. (Jul. 2010). "Oral Peanut Immunotherapy in Children With Peanut Anaphylaxis," *J Allergy Clin Immunol.* 126(1):83-91.

Bock, S.A. et al. (Dec. 1988). "Doubleblind, Placebo-Controlled Food Challenge (DBPCFC) As An Office Procedure: A Manual,". *J Allergy Clin Immunol.* 82(6):986-997.

Bock, S.A. et al. (Oct. 1990). "Patterns of Food Hypersensitivity During Sixteen Years Of Double-Blind, Placebo-Controlled Food Challenges," *J Pediatr.* 117(4):561-567.

Bock, S.A. et al. (Jan. 2001). "Fatalities Due To Anaphylactic Reactions To Foods," *J Allergy Clin. Immunol.* 107(1):191-193.

Bousquet, J. (2004). "Primary and Secondary Prevention Of Allergy And Asthma By Allergen Therapeutic Vaccines," in *Allergens and Allergen Immunotherapy* 18:105-114.

Buchanan, A.D. et al. (Jan. 2007). "Egg Oral Immunotherapy In Nonanaphylactic Children With Egg Allergy," *J. Allergy Clin. Immunol.* 119:199-205.

Burks, W. et al. (1998). "Review Article Series II: Peanut Allergens," *Allergy* 53:725-730.

Burks, W. (2000). "Diagnosis Of Allergic Reactions To Food," *Pediatr. Ann.* 29:744-752. [First page of Document Only].

Burks, W. (May 2002). "Current Understanding Of Food Allergy," *Ann. NY. Acad. Sci.* 964:1-12.

Burks, W. (Jun. 2003). "Skin Manifestations Of Food Allergy," *Pediatrics* 111(6):1617-1624.

Burks, W. (Apr. 2003). "Peanut Allergy: A Growing Phenomenon," *J. Clin. Invest.* 111(7):950-952.

Burks, A.W. (2009). "Early Peanut Consumption: Postpone Or Promote?," *J. Allergy Clin.Immunol.* 123(2):424-425.

Burks, W. (2004). "Chapter 17: Food Allergens," *Clin. Allergy Immunol.* 18:319-337.

Burks, a.W. et al. (Jul. 19, 2012). "Oral Immunotherapy for Treatment of Egg Allergy in Children," *N. Engl. J. Med.* 367:233-243.

Burks, W. (American Academy of Allergy, Asthma, and Immunology National Conference. Orlando, Florida, Mar. 6, 2012). 2012 American Academy of Allergy, Asthma & Immunology Annual Meeting. "Food Allergy" "Oral Immunotherapy for Food Allergens" "Food Allergy Guidelines" "Oral Desensitization in Patients with Food Allergy" Orlando, FL Mar., 2012, 108 pages.

Fiocchi, A. et al. (Jul. 2006). "Food Allergy and The Introduction Of Solid Foods To Infants: A Consensus Document," *Ann. Allergy Asthma Immunol.* 97:10-21.

Frew, A.J. (2003). "25. Immunotherapy Of Allergic Disease," *J. Allergy Clin. Immunol.* 111(2 Suppl): S712-S719.

Fung, et al. (Jan. 8, 2013). "Relating Microarray Component Testing and Reported Food Allergy and Food-Triggered Atopic Dermatitis: A Real-World Analysis," *Annals of Allergy, Asthma & Immunology* 110(3):173-177.

Hofmann, A.M. et al. (Aug. 2009). "Safety of A Peanut Oral Immunotherapy Protocol In Children With Peanut Allergy," *J. Allergy Clin. Immunol.* 124:286-291, 14 pages.

Jones, S.M. et al. (Aug. 2009). "Clinical Efficacy and Immune Regulation With Peanut Oral Immunotherapy," *J. Allergy Clin. Immunol.* 124(2):292-30197, 20 pages.

Jones, S. M. et al. (2014). "State of the Art On Food Allergen Immunotherapy: Oral, Sublingual, and Epicutaneous," *J. Allergy Clin. Immunol.* 133(2):318-323.

Joshi, P.S. et al. (Jun. 2002). "Interpretation Of Commercial Food Ingredient Labels By Parents Of Food-Allergic Children," *J. Allergy Clin. Immunol.* 109( 6):1019-1021.

Kapsenberg, M.L. et al. (Jun. 1999). "The Paradigm Of Type 1 and Type 2 Antigen-Presenting Cells. Implications For Atopic Allergy," *Clin. Exp. Allergy* 29(Suppl 2):33-36.

Kim, E.H., et al. (Mar. 2011). "Sublingual Immunotherapy For Peanut Allergy: Clinical and Immunologic Evidence Of Desensitization," *J. Allergy Clin. Immunol.* 127(3):640-646, 19 pages.

Koid, A. et al. (Jan. 8, 2014). "Ara h 6 Complements Ara h 2 As An Important Marker For IgE Reactivity To Peanut," *J. Agric. Food Chem.* 62(1):206-213, 18 pages.

Koppelman et al. (Feb. 19, 1999). "Heat-Induced Conformational Changes of Ara h 1, A Major Peanut Allergen, Do Not Affect Its Allergenic Properties," *J. Biol. Chem.* 274(8):4770-4777.

Krieg et al. (Apr. 6, 1995). "CpG Motifs in Bacterial DNA Trigger Direct B-Cell Activation," *Nature* 374:546-549.

Krimpenfort et al. (1988). "Transcription Of T Cell Receptor β-Chain Genes Is Controlled By A Downstream Regulatory Element," *EMBO J.* 7(3):745-750.

Kulis, et al. (Feb. 2012). The 2S Albumin Allergens of *Archis hypogaea*, Ara h 2 and Ara h 6, are the Major Elicitors of Anaphylaxis and Can Effectively Desensitize Peanut-Allergic Mice, *Clinical & Experimental Allergy: Journal of British Society for Allergy and Clinical Immunology* 42(2):326-336, 18 pages.

Lehmann, K. et al. (2006). "Structure and Stability of 2S Albumin-Type Peanut Allergens: Implications For The Severity Of Peanut Allergic Reactions," *Biochem. J.* 395:463-472.

Lehrer, S.B. et al. (1999). "Immunotherapy For Food Allergies. Past, Present, Future," *Clin. Rev. Allergy Immunol.* 17(3):361-381.

Mondoulet et al. (Feb. 21, 2012). "Epicutaneous Immunotherapy (EPIT) Blocks the Allergic Esophago-Gastro-Enteropathy Induced by Sustained Oral Exposure to Peanuts in Sensitized Mice," *Plos One* 7(2):e31967, 10 pages.

Narisety, S.D. et al. (Sep. 2009). "Open-Label Maintenance After Milk Oral Immunotherapy For IgE-Mediated Cow's Milk Allergy," *J. Allergy Clin. Immunol.* 124(3):610-612, 6 pages.

(56) References Cited

OTHER PUBLICATIONS

Nelson, H.S. et al. (1997). "Treatment Of Anaphylactic Sensitivity To Peanuts By Immunotherapy With Injections Of Aqueous Peanut Extract," *J. Allergy Clin. Immunol.* 99(6 Pt 1):744-751.
Oppenheimer, J.J. et al. (Aug. 1992). "Treatment Of Peanut Allergy With Rush Immunotherapy," *J. Allergy Clin. Immunol.* 90(2):256-262.
Pingali et al. (May 16, 2011, e-pub. Feb. 26, 2011). "Mixing Order Of Glidant and Lubricant—Influence On Powder and Table Properties," *Int. J. Pharm.* 409:269-277, 22 pages.
Pisetsky, D.S. (Oct. 1996). "Immune Activation by Bacyterial DNA: A New Genetic Code," *Immunity* 5:303-310.
Poms, R.E. et al. (2004). "Effect Of Roasting History and Buffer Composition On Peanut Protein Extraction Efficiency," *Mol. Nutr. Food Res.* 48:459-464.
Sampson, H.A. et al. (2005). "Symposium On The Definition And Management Of Anaphylaxis: Summary Report," *J. Allergy Clin. Immunol.* 115(3):584-591.
Schmitt, D.A. et al. (2010, e-pub. Dec. 22, 2009). "Processing Can Alter the Properties Of Peanut Extract Preparations," *J. Agric. Food Chem.* 58:1138-1143.
Secrist, H. et al. (Mar. 1995). "Interleukin 4 Production By CD4+ T Cells From Allergic Individuals Is Modulated By Antigen Concentration and Antigen-Presenting Cell Type," *J. Exp. Med.* 181(3):1081-1089.
Sen, M. et al. (2002). "Protein Structure Plays a Critical Role In Peanut Allergen Stability and May Determine Immunodominant IgE-Binding Epitopes," *The Journal Of Immunology* 169:882-887.
Sicherer, S.H. et al. (Jul. 1998). "Clinical Features Of Acute Allergic Reactions To Peanut and Tree Nuts In Children," *Pediatrics* 102(1):1-6.
Sicherer, S.H. (Nov. 1999). "Food Allergy: When and How To Perform Oral Food Challenges," *Pediatr. Allergy Immunol.* 10(4):226-234.
Sicherer, S.H. et al. (May 2010). "Immunologic features Of Infants With Milk Or Egg Allergy Enrolled In An Observational Study (Consortium of Food Allergy Research) Of Food Allergy)," *J. Allergy Clin. Immunol.* 125:1077-1083, 14 pages.
Skolnick, H.S. et al. (2001). "The Natural History Of Peanut Allergy," *J. Allergy Clin. Immunol.* 107(2):367-374.
Skripak, J.M. et al. (Dec. 2008). "A Randomized, Double-Blind, Placebo-Controlled Study Of Milk Oral Immunotherapy For Cow's Milk Allergy," *J. Allergy Clin. Immunol.* 122(6):1154-1160, 20 pages.
Skripak, J.M. et al. (2009). "Mammalian Milk Allergy: Avoidance Strategies and Oral Desensitization," *Curr. Opin. Allergy Clin. Immunol.* 9:259-264.
Thyagarajan, A. et al. (2009). "Basophil Suppression in Peanut Allergic Subjects undergoing Peanut Oral Immunotherapy (OIT)," *Journal of Allergy and Clinical Immunology* 123:S214-S214, Abstract No. 826, (Abstract Only).
Vierk, K. et al. (2002). "Recalls Of Foods Containing Undeclared Allergens Reported To The US Food And Drug Administration, Fiscal Year 1999," *J. Allergy Clin. Immunol.* 109(6):1022-1026.
Wilson, D.R. et al. (2005). "Sublingual Immunotherapy For Allergic Rhinitis: Systematic Review and Meta-Analysis," *Allergy* 60(1):4-12.
Yamamoto et al. (1992). "DNA From Bacteria, But Not From Vertebrates, Induces Interferons, Activates Natural Killer Cells And Inhibits Tumor Growth," *Microbial. Immunol.* 36:983-997.
Zhuang, Y. et al. (Sep. 5, 2012). "Redefining the Major Peanut Allergens," *Immunologic Research* 55(1-3):125-134.
Zimmerman et al. (1998). "Cutting Edge: CpG Oligodeoxynucleotides Trigger Protective and Curative Th1 Responses in Lethal Murine Leishmaniasis," *J. Immunol.* 160:3627-3630.
Australian Patent Examination Report No. 1, dated Mar. 31, 2013, for Australian Patent Application No. AU2014240404, 3 pages.
European Extended Search Report for European Application No. 14776121.7, dated Sep. 7, 2016, 8 pages.
European Communication Rule 114(2) for European Application No. 14776121.7, dated Oct. 12, 2017, 63 pages.
European Communication Rule 94(3) for European Application No. 14776121.7, dated Dec. 19, 2017, 9 pages.
European Communication Rule 70(2) and 70a(2) for European Application No. 1477621.7, dated Sep. 23, 2016, 1 page.
Response to Communication Rule 70a(2) for European Application No. 1477621.7, dated Mar. 26, 2017, 13 pages.
European Communication Rule 161(2) for European Application No. 1477621.7, dated Oct. 23, 2015, 2 page.
Response to Communication Rule 161(1) for European Application No. 1477621.7, dated Apr. 29, 2016, 17 pages.
International Preliminary Report on Patentability Search Report for PCT Application PCT/US2014/024401, dated Sep. 15, 2015, 10 pages.
Notice of Allowance for Patent Application No. 14/207,165, dated Jul. 23, 2015, 10 pages.
Pre-interview First Office Action for U.S. Appl. No. 14/207,165, dated Mar. 12, 2015, 4 pages.
U.S. Appl. No. 15/870,477, Reyna et al, filed Jan. 12, 2018.

\* cited by examiner

Schematic for Initial (Visit 01) Day Treatment

FIGURE 1B

Schematic for Build Up Phase Dose Escalation - Day of Symptom

Initial First Day Escalation Schedule

| Dose no. | Peanut dose (mg) | Cumulative Peanut dose (mg)* |
|---|---|---|
| 1 | 0.5 mg' | 0.5 mg |
| 2 | 1.0 mg | 1.5 mg |
| 5 | 1.5 mg | 3.0 mg |
| 6 | 3.0 mg | 6.0 mg |
| 7 | 6.0 mg | 12 mg |

Frequency standard every 30 min

\* If no de-escalation

Subjects at the end of the first day, tolerating less than 1.5 mg single dose, will be considered an initial day escalation desensitization failure.

Subjects tolerating 1.5, 3, 6mg single dose will go home on the greatest tolerated dose to be given daily (first dose given in Clinical Research Center under observation). All escalations will occur no sooner than 2 weeks and dose increases in the Clinical Research Center from 1.5 to 3 to 6 mg will be attempted.

All subjects will return on Day 2 and receive their maximum tolerated dose under direct observation.

Subjects with moderate symptoms observed on Day 2 will return on Day 3 for the next lower dose under observation in the
Clinical Research Center or monitored clinic setting.

Doses on day 2, 3 and 4 must be at least 1.5 mg or the subject will be considered an escalation failure

Schematic for Build Up Phase Dose Escalation – Day of Symptom

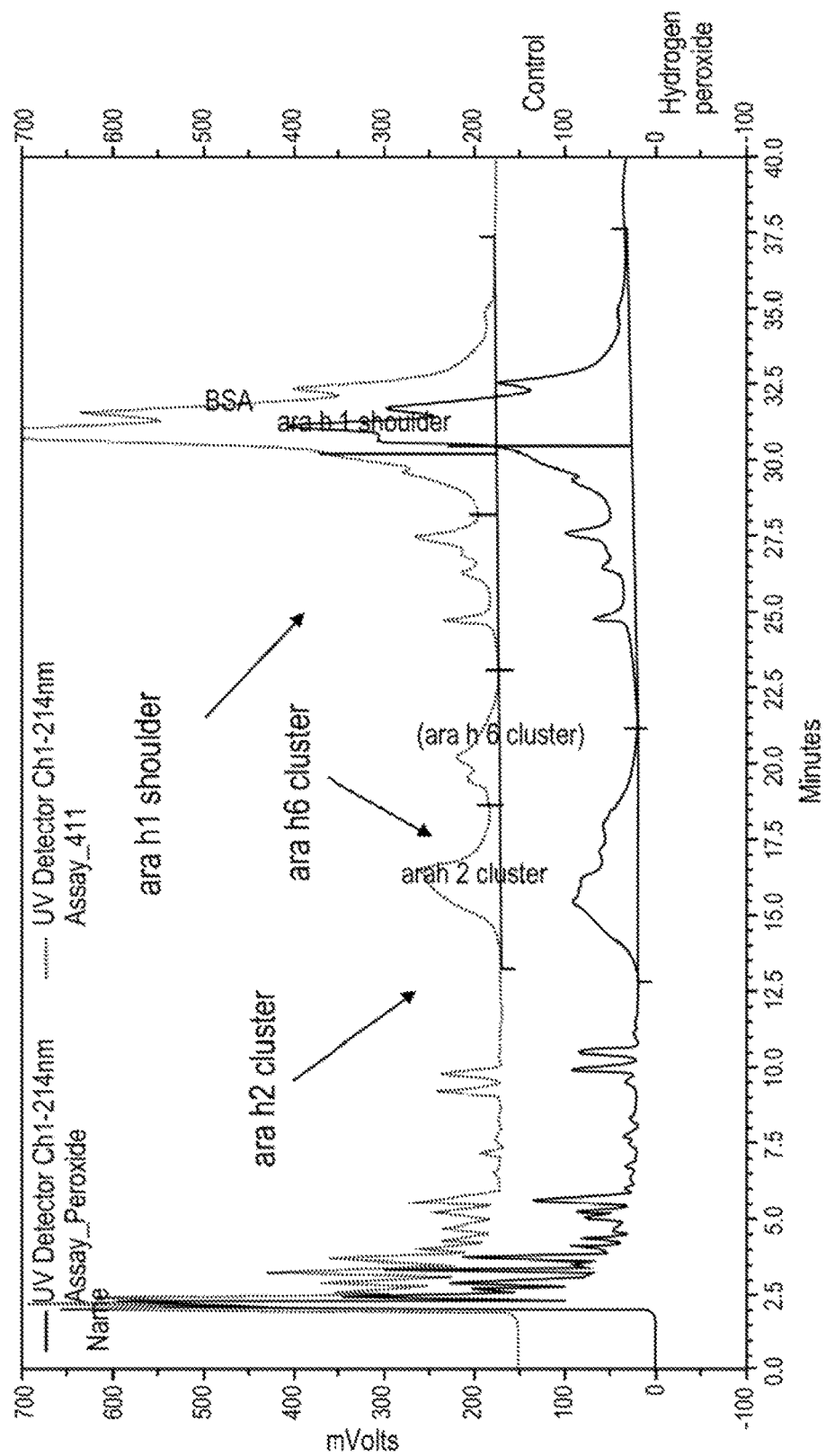

PEANUT FORMULATIONS AND USES THEREOF

CROSS REFERENCE

This application is a continuation of co-pending U.S. patent application Ser. No. 14/207,127, filed Mar. 12, 2014, which claims the benefit of priority to U.S. Provisional Application No. 61/784,863, filed Mar. 14, 2013, the entirety of which is incorporated herein by reference.

This application is related to U.S. Provisional Application No. 61/784,964, filed Mar. 14, 2013, entitled "Manufacture of Peanut Formulations for Oral Desensitization", which is incorporated herein by reference in its entirety.

BACKGROUND OF THE INVENTION

Allergies affect humans and companion animals and some allergic reactions (for example, those to insects, foods, latex, and drugs) can be so severe as to be life threatening.

Allergic reactions result when a subject's immune system responds to an allergen. Typically, there is no allergic reaction the first time a subject is exposed to a particular allergen. However, it is the initial response to an allergen that primes the system for subsequent allergic reactions. In particular, the allergen is taken up by antigen presenting cells (APCs; e.g., macrophages and dendritic cells) that degrade the allergen and then display allergen fragments to T-cells. T-cells, in particular CD4+ "helper" T-cells, respond by secreting a collection of cytokines that have effects on other immune system cells. The profile of cytokines secreted by responding CD4+ T-cells determines whether subsequent exposures to the allergen will induce allergic reactions. Two classes of CD4+ T-cells (Th1 and Th2; T-lymphocyte helper type) influence the type of immune response that is mounted against an allergen.

The Th1-type immune response involves the stimulation of cellular immunity to allergens and infectious agents and is characterized by the secretion of IL-2, IL-6, IL-12, IFN-gamma, and TNF-beta by CD4+ T helper cells and the production of IgG antibodies. Exposure of CD4+ T-cells to allergens can also activate the cells to develop into Th2 cells, which secrete IL-4, IL-5, IL-10, and IL-13. IL-4 production stimulates maturation of B cells that produce IgE antibodies specific for the allergen. These allergen-specific IgE antibodies attach mast cell and basophil receptors, where they initiate a rapid immune response to the next exposure to allergen. When the subject encounters the allergen a second time, the allergen is quickly bound by these surface-associated IgE molecules, resulting in the release of histamines and other substances that trigger allergic reactions. Subjects with high levels of IgE antibodies are known to be particularly prone to allergies.

SUMMARY OF THE INVENTION

The present inventors have developed new formulations of peanut flour comprising characterized peanut allergens that may be formulated into a pharmaceutical composition that, when administered to a patient according to a treatment regimen provided herein, provides oral immunotherapy (OIT) for subjects that are allergic to peanuts. Following treatment, subjects administered an oral food challenge (OFC) are partially or fully desensitized to peanuts.

Provided herein is a composition, comprising peanut flour comprising one or more peanut allergens and optionally, one or more gliders, one or more lubricants, one or more diluents.

In one embodiment, the composition is for use for treatment of peanut allergy.

In another embodiment, the composition is for use for desensitization of subjects suffering from allergies to peanuts.

In another embodiment, the one or more peanut proteins are Ara h1, Ara h2, Ara h6, or a combination thereof.

A composition described herein may be formulated for oral administration. In one embodiment, the composition of claim 1, wherein the composition is formulated as a capsule, a tablet, a mini-tablet, a powder, or a sprinkle.

In another embodiment, the composition is a capsule comprising a white opaque HPMC capsule shell (e.g., Capsugel).

The one or more diluents may be selected from the group consisting of alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), microcrystalline cellulose (e.g., Avicel®); silicified microcrystalline cellulse; microcrystalline dextrose; amylose; magnesium aluminum silicate; polysaccharide acids; bentonites; gelatin; polyvinylpyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), lactose (e.g., lactose monohydrate, lactose anhydrous, etc.); dicalcium phosphate; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, a starch, e.g., a natural starch such as corn starch or potato starch, a pregelatinized starch such as Colorcon (Starch 1500), National 1551 or Amijel®, or sodium starch glycolate such as Promogel® or Explotab®; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and combinations thereof. In one embodiment, the diluent is microcrystalline cellulose or starch 1500. In another embodiment, the diluents are microcrystalline cellulose and starch 1500.

The one or more glidants may be selected from the group consisting of colloidal silicon dioxide (Cab-O-Sil), talc (e.g., Ultra Talc 4000), and combinations thereof. In one embodiment, the glidant is Cab-O-Sil.

The one or more lubricants may be selected from the group consisting of stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and combinations thereof. In one embodiment, the lubricant is magnesium stearate. In another embodiment, the lubricant is sodium stearyl fumerate.

The composition may be formulated in a dose of about 0.5 mg, about 1.0 mg, about 10.0 mg, 100 mg, about 475 mg, about 500 mg or about 1000 mg.

The composition may comprise peanut flour in a concentration from about 0.05% to about 100% w/w, or from about 0.1% to about 100% w/w. In one embodiment, the composition comprises peanut flour in a concentration from about 0.5%, about 1%, about 2%, about 4%, or about 100% w/w. In another embodiment, the composition comprises peanut flour in a concentration from about 0.7%, about 1.42%, about 3.93%, or about 100% w/w.

The composition may comprise peanut flour in a concentration from about a target unit weight from about 0.5 mg/capsule to about 1100 mg/capsule; or from about 1.0 mg/capsule to about 1000 mg/capsule. In one embodiment, the composition comprises peanut flour in a concentration from about a target unit weight of about 1.0 mg/capsule, about 2 mg/capsule, about 20 mg/capsule, about 200 mg/capsule, or about 1000 mg/capsule. In another embodiment, the amount of peanut flour is 50% w/w of the flour in the composition.

The total amount of peanut flour may be from about 8% to about 15% w/w, from about 9% to about 12% w/w, or from about 10% to about 11% w/w of the composition.

In one embodiment, the total amount of peanut flour is about 11% w/w of the composition.

In one embodiment, the concentration of Ara h1 in said composition comprises from about 8% to about 15% w/w, from about 9% to about 12% w/w, or from about 10% to about 11% w/w of the composition.

In one embodiment, the concentration of Ara h2 in said composition comprises about 8% to about 15% w/w, from about 9% to about 12% w/w, or from about 9% to about 10% w/w of the composition.

In one embodiment, the concentration of Ara h6 in said composition comprises about 2% to about 10% w/w, from about 3% to about 9% w/w, or from about 4% to about 6% w/w of the composition.

In one embodiment, the dose of the composition is 0.5 mg and the concentration of Ara h1 comprises from about 0.035 to about 0.075 mg;

In another embodiment, the dose of the composition is 1.0 mg and the concentration of Ara h1 comprises from about 0.075 to about 0.15 mg;

In another embodiment, the dose of the composition is 10.0 mg and the concentration of Ara h1 comprises from about 0.5 to about 1.5 mg;

In another embodiment, the dose of the composition is 100.0 mg and the concentration of Ara h1 comprises from about 7.5 to about 15 mg; or In another embodiment, the dose of the composition is 475 mg and the concentration of Ara h1 comprises from about 35 to about 60 mg.

In one embodiment, dose of the composition is 0.5 mg and the concentration of Ara h2 comprises from about 0.035 to about 0.075 mg;

In another embodiment, the dose of the composition is 1.0 mg and the concentration of Ara h2 comprises from about 0.075 to about 0.175 mg;

In another embodiment, the dose of the composition is 10.0 mg and the concentration of Ara h2 comprises from about 0.5 to about 1.75 mg;

In another embodiment, the dose of the composition is 100.0 mg and the concentration of Ara h2 comprises from about 7.5 to about 15 mg; or In another embodiment, the dose of the composition is 475 mg and the concentration of Ara h2 comprises from about 45 to about 65 mg.

In one embodiment, the dose of the composition is 0.5 mg and the concentration of Ara h6 comprises from about 0.015 to about 0.06 mg;

In another embodiment, the dose of the composition is 1.0 mg and the concentration of Ara h6 comprises from about 0.025 to about 1.0 mg;

In another embodiment, the dose of the composition is 10.0 mg and the concentration of Ara h6 comprises from about 0.35 to about 1.0 mg;

In another embodiment, the dose of the composition is 100.0 mg and the concentration of Ara h6 comprises from about 3.5 to about 10 mg; or In another embodiment, the dose of the composition is 475 mg and the concentration of Ara h6 comprises from about 15 to about 40 mg.

The composition may comprise one or more diluents in an amount of from about 1% to about 99% w/w, from about 60% to about 90%, or from about 5% to about 20% w/w of the composition. In one embodiment, the concentration of diluent comprises about 10%, 65%, about 85%, about 87% or about 88% w/w of the composition.

The target unit weight of the diluent may comprise from about 10 to about 60 mg/capsule or from about 100 to about 410 mg/capsule. In one embodiment, the target unit weight of the diluent comprises about 14, about 52, about 125.55, about 126.99, about 446.61, or about 394 mg/capsule.

The glider may comprise from about 0.01% to about 10% w/w of the composition. In one embodiment, the glider comprises about 0.01%, about 0.05%, about 0.1%, about 0.25%, about 0.5%, about 0.75%, about 1.0%, about 1.25%, or about 1.5% w/w of the composition.

The composition of claim 1, wherein the target unit weight of the glider comprises from about 0.05 to about 5 mg/capsule. In one embodiment, the glider comprises about 0.725, about 2.625 or about 3.0 mg/capsule. In another embodiment, the glider is colloidal silicon dioxide (Cab-O-Sil).

The lubricant may comprise from about 0.01% to about 10% w/w of the composition. In one embodiment, the lubricant comprises about 0.01%, about 0.05%, about 0.1%, about 0.25%, about 0.5%, about 0.75%, about 1.0%, about 1.25%, or about 1.5% w/w of the composition.

The target unit weight of the lubricant may comprise from about 0.05 to about 5 mg/capsule In one embodiment, the lubricant comprises about 0.725, about 2.625 or about 3.0 mg/capsule. In another embodiment, the lubricant comprises magnesium stearate.

Any of the compositions provided herein may further comprise a food product. A food product as provided herein may be any food with which the formulation may be mixed for consumption.

Provided herein is a composition comprising (a) peanut flour in a concentration from about 0.05% to about 100% w/w or from about 0.1% to about 100% w/w; (b) one or more diluents in an amount of from about 1% to about 99% w/w, from about 60% to about 90%, or from about 5% to about 20% w/w of the composition; (c) one or more gliders in an amount 0.01% to about 10% w/w of the composition; and (d) one or more lubricant in an amount of from about 0.01% to about 10% w/w of the composition.

The composition may comprise peanut flour comprising one or more peanut protein allergens, one or more diluents, one or more lubricants and one or more gliders. In one embodiment, the peanut proteins comprise Ara h1, Ara h2 and Ara h6.

In another embodiment, the one or more diluents comprise starch 1500 and microcrystalline cellulose.

In another embodiment, the one or more lubricants comprise magnesium stearate.

In another embodiment, the glidant comprises colloidal silicon dioxide (Cab-O-Sil).

In another embodiment, the composition further comprises a food product.

The protein extraction and analytical methods described herein may, in some instances, be used for quality control of peanut flour. In one embodiment, the HPLC methods allow for identification of protein flour for exclusion from use in a composition provided herein. In another embodiment, the HPLC methods allow for development of consistent characterized peanut allergens for use in a composition provided herein.

Provided herein is a composition comprising peanut flour comprising one or more peanut proteins and optionally, one or more gliders, one or more lubricants, one or more diluents, wherein the concentration of Ara h1 in the peanut flour comprises from about 0.035 to about 60.0 mg as determined by reverse phase HPLC.

Also provided herein is a composition comprising peanut flour comprising one or more peanut proteins and optionally, one or more gliders, one or more lubricants, one or more diluents, wherein the concentration of Ara h2 in the peanut flour comprises from about 0.035 to about 65.0 mg as determined by reverse phase HPLC.

Also provided herein is a composition comprising peanut flour comprising one or more peanut proteins and optionally, one or more gliders, one or more lubricants, one or more diluents, wherein the concentration of Ara h6 in the peanut flour comprises from about 0.015 to about 40.0 mg as determined by reverse phase HPLC.

Provided herein is a method of identifying a composition for treatment for desensitization of peanut allergy in a subject, comprising: (a) determining the concentrations of Ara h1, Ara h2 and Ara h6 in a composition of peanut flour by RP-HPLC; (b) comparing the concentrations to the concentrations of a reference standard; and (c) identifying a composition for desensitization of peanut allergy in a subject, wherein the sample contains at least the concentrations of Ara h1, Ara h2 and Ara h6 of the reference standard.

The method may, in some instances, further comprise administering a composition described herein to a subject, wherein the composition comprises at least the concentrations of Ara h1, Ara h2 and Ara h6 of the reference standard.

The method may be used to compare lots of peanut flour and, in some instances, exclude peanut flour from use in a composition or method described herein where the sample does not contain at least the reference standard amount of Ara h1, Ara h2 and Ara h6.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1B illustrates an exemplary initial first day escalation schedule.

FIG. 20: Chromatogram results showing the effects of treating peanut flour for 24 hours with 3% peroxide.

DETAILED DESCRIPTION OF THE INVENTION

Figure 1A:
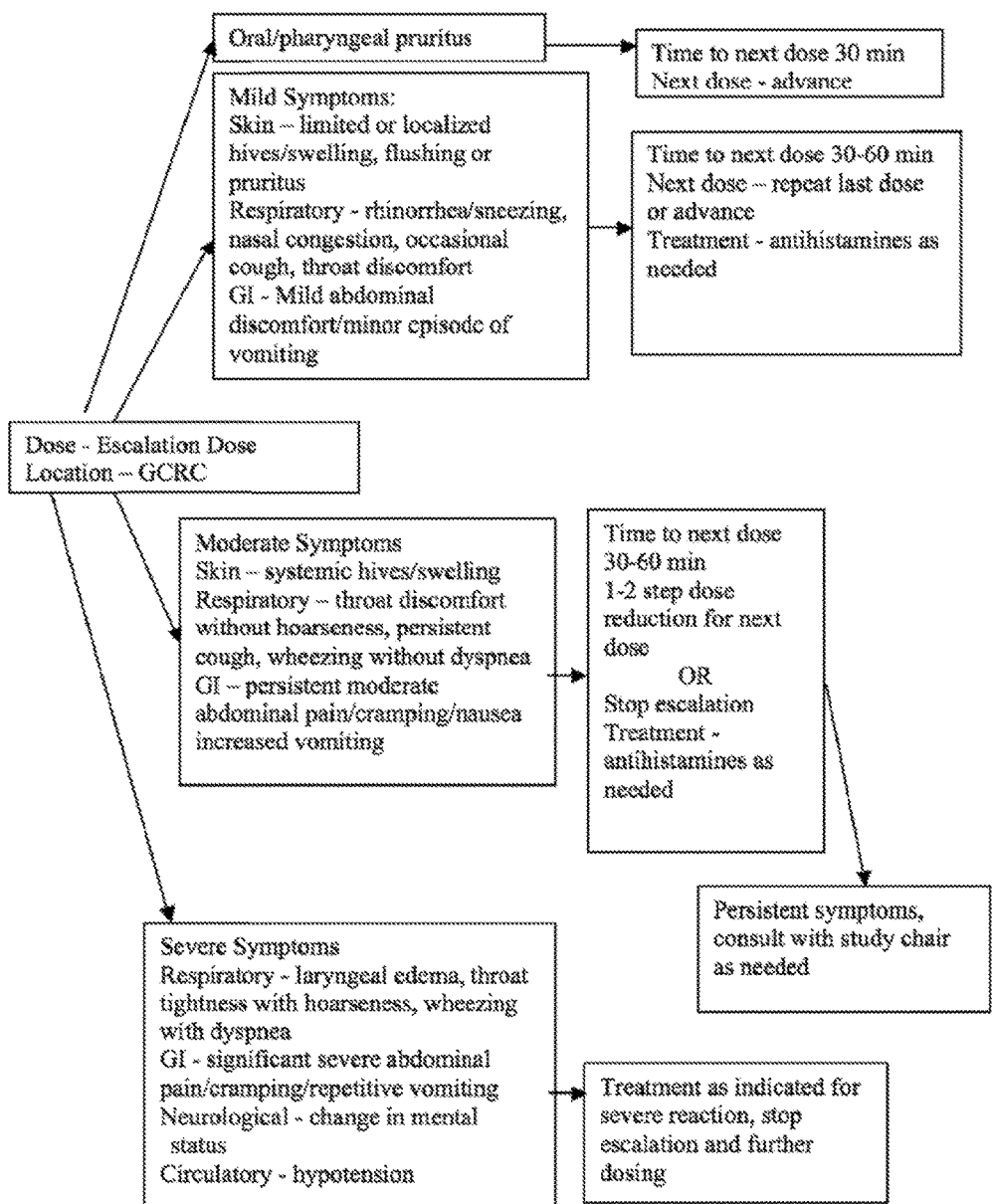
FIG. 1A Illustrates a Schematic for Initial (Visit 01) Day Treatment.

During the past decade, much has been learned about allergens in peanut. Peanuts are commonly associated with severe reactions, including life threatening anaphylaxis. The current standard of care in management of food allergy is dietary avoidance of the food and education of the subject/family in the acute management of an allergic reaction. The burden of avoidance and constant fear of accidental exposure negatively impacts the health-related quality of life for both subjects and their families. Quality of life surveys indicate that families with children having food allergies have significant impact on food preparation, social activities, finding appropriate childcare, school attendance, and level of stress among other things.

Currently, the only treatment for peanut allergy is a peanut-free diet and ready access to self-injectable epinephrine. However, strict avoidance diets can be complicated due to difficulty in interpreting labels and by the presence of undeclared or hidden allergens in commercially prepared foods. Accidental ingestions are unfortunately common, with up to 50% of food-allergic subjects having an allergic reaction over a two-year period. Allergic reactions to peanut can be severe and life threatening; and peanut and/or tree nut allergies account for the vast majority of fatal food-induced anaphylaxis. This combination of strict avoidance diets, the high incidence of accidental exposures, and the risk of severe or even fatal reactions with accidental exposures adds a tremendous burden and stress on subjects and their families. Further complicating matters is the fact that only about 20% of children will outgrow peanut allergy, meaning that the majority of people with peanut allergy will have it for the rest of their lives. If we couple the rising prevalence and increased consumption of peanut in Western countries with the facts that only approximately 1 in 5 will outgrow their allergy, that allergic reactions have the potential to be severe or even fatal, and that accidental exposures are common, developing an effective treatment for peanut allergy becomes even more imperative.

Specific immunotherapy for food allergy, in particular peanut allergy, in the forms of oral immunotherapy (OIT) and sublingual immunotherapy (SLIT) has been studied in recent years and has demonstrated encouraging safety and efficacy results in early clinical trials, including beneficial immunologic changes. OIT has shown evidence for inducing desensitization in most subjects with immunologic changes over time indicating progression toward clinical tolerance.

Peanut OIT: In Jones et al., peanut allergic children underwent an OIT protocol consisting of an initial dose escalation day, bi-weekly build-up (to 2 g) and daily maintenance phase followed by an OFC. After tolerating less than 50 mg peanut protein during an oral food challenge (OFC) at baseline, 27 of the 29 subjects ingested 3.9 g of peanut protein at the completion of OIT protocol.

Recently, Dr. Wesley Burks. (American Academy of Allergy, Asthma, and Immunology National Conference. Orlando, Fla., Mar. 6, 2012) presented work showing that 10 children with PA completed an OIT protocol and underwent an oral food challenge (OFC) 4 weeks after cessation of oral intake of peanut to evaluate the development of clinical "sustained unresponsiveness". Three out of 10 subjects passed the OFC; the authors considered these subjects as clinically tolerant. Over the course of treatment, peanut IgE levels lower than 85 kU/L at a time point of 3 months into OIT was predictive of subjects who became immune tolerant.

A multi-center double-blinded randomized placebo-controlled study reported by Varshney, et al., examined twenty-eight subjects. Three subjects withdrew early in the study because of allergic side effects. After completing up-dosing, a double-blind placebo-controlled food challenge was performed, in which all remaining peanut OIT subjects (n=16) ingested the maximum cumulative dose of 5000 mg (approximately 20 peanuts), whereas placebo subjects (n=9) could tolerate only a median cumulative dose of 280 mg (range, 0-1900 mg; p<0.001). In contrast with the placebo group, the peanut OIT group showed reductions in skin prick test size (P<0.001) and increases in peanut-specific IgG4 (P<0.001). Peanut OIT subjects had initial increases in peanut-specific IgE (P<0.01) but did not show significant change from baseline by the time of oral food challenge.

Definitions

Unless defined otherwise, all technical and scientific terms used herein have the same meaning as is commonly understood by one of skill in the art to which the inventions described herein belong. All patents and publications referred to herein are incorporated by reference.

The term "animal", as used herein, refers to humans as well as non-human animals, including, for example, mammals, birds, reptiles, amphibians, and fish. Preferably, the non-human animal is a mammal (e.g., a rodent, a mouse, a rat, a rabbit, a monkey, a dog, a cat, a primate, or a pig). An animal may be a transgenic animal.

The term "antigen", as used herein, refers to a molecule that elicits production of an antibody response (i.e., a humoral response) and/or an antigen-specific reaction with T-cells (i.e., a cellular response) in an animal.

The term "allergen", as used herein, refers to a subset of antigens which elicit the production of IgE in addition to other isotypes of antibodies. The terms "allergen", "natural allergen", and "wild-type allergen" may be used interchangeably. Preferred allergens for the purpose of the present invention are protein allergens.

The phrase "allergic reaction", as used herein, relates to an immune response that is IgE mediated with clinical symptoms primarily involving the cutaneous (e.g., uticana, angiodema, pruritus), respiratory (e.g., wheezing, coughing, laryngeal edema, rhinorrhea, watery/itching eyes), gastrointestinal (e.g., vomiting, abdominal pain, diarrhea), and cardiovascular (i.e., if a systemic reaction occurs) systems. For the purposes of the present invention, an asthmatic reaction is considered to be a form of allergic reaction.

The phrase "anaphylactic allergen", as used herein, refers to a subset of allergens that are recognized to present a risk of anaphylactic reaction in allergic individuals when encountered in its natural state, under natural conditions. For example, for the purposes of the present invention, pollen allergens, mite allergens, allergens in animal danders or excretions (e.g., saliva, urine), and fungi allergens are not considered to be anaphylactic allergens. On the other hand, food allergens, insect allergens, and rubber allergens (e.g., from latex) are generally considered to be anaphylactic allergens. Food allergens are particularly preferred anaphylactic allergens for use in the practice of the present invention. In particular, nut allergens (e.g., from peanut, walnut, almond, pecan, cashew, hazelnut, pistachio, pine nut, brazil nut), dairy allergens (e.g., from egg, milk), seed allergens (e.g., from sesame, poppy, mustard), soybean, wheat, and fish allergens (e.g., from shrimp, crab, lobster, clams, mussels, oysters, scallops, crayfish) are anaphylactic food allergens according to the present invention. Particularly interesting anaphylactic allergens are those to which reactions are commonly so severe as to create a risk of death.

The phrase "anaphylaxis" or "anaphylactic reaction", as used herein, refers to a subset of allergic reactions characterized by mast cell degranulation secondary to cross-linking of the high-affinity IgE receptor on mast cells and basophils induced by an anaphylactic allergen with subsequent mediator release and the production of severe systemic pathological responses in target organs, e.g., airway, skin digestive tract, and cardiovascular system. As is known in the art, the severity of an anaphylactic reaction may be monitored, for example, by assaying cutaneous reactions, puffiness around the eyes and mouth, vomiting, and/or diarrhea, followed by respiratory reactions such as wheezing and labored respiration. The most severe anaphylactic reactions can result in loss of consciousness and/or death.

The phrase "antigen presenting cell" or "APC", as used herein, refers to cells which process and present antigens to T-cells to elicit an antigen-specific response, e.g., macrophages and dendritic cells.

When two entities are "associated with" one another as described herein, they are linked by a direct or indirect covalent or non-covalent interaction. Preferably, the association is covalent. Desirable non-covalent interactions include, for example, hydrogen bonding, van der Walls interactions, hydrophobic interactions, magnetic interactions, etc.

The phrase "decreased anaphylactic reaction", as used herein, relates to a decrease in clinical symptoms following treatment of symptoms associated with exposure to an anaphylactic allergen, which can involve exposure via cutaneous, respiratory, gastrointestinal, and mucosal (e.g., ocular, nasal, and aural) surfaces or a subcutaneous injection (e.g., via a bee sting).

The term "epitope", as used herein, refers to a binding site including an amino acid motif of between approximately six and fifteen amino acids which can be bound by an immunoglobulin (e.g., IgE, IgG, etc.) or recognized by a T-cell receptor when presented by an APC in conjunction with the major histocompatibility complex (MHC). A linear epitope is one where the amino acids are recognized in the context of a simple linear sequence. A conformational epitope is one where the amino acids are recognized in the context of a particular three dimensional structure.

An allergen "fragment" according to the present invention is any part or portion of the allergen that is smaller than the intact natural allergen. In preferred embodiments of the invention, the allergen is a protein and the fragment is a peptide.

The phrase "immunodominant epitope", as used herein, refers to an epitope which is bound by antibody in a large percentage of the sensitized population or where the titer of the antibody is high, relative to the percentage or titer of antibody reaction to other epitopes present in the same antigen. In one embodiment, an immunodominant epitope is bound by antibody in more than 50% of the sensitive population, more preferably more than 60%, 70%, 80%, 90%, 95%, or 99%.

The phrase "immunostimulatory sequences" or "ISS", as used herein, relates to oligodeoxynucleotides of bacterial, viral, or invertebrate origin that are taken-up by APCs and activate them to express certain membrane receptors (e.g., B7-1 and B7-2) and secrete various cytokines (e.g., IL-1, IL-6, IL-12, TNF). These oligodeoxynucleotides contain unmethylated CpG motifs and when injected into animals in conjunction with an antigen, appear to skew the immune response towards a Th1-type response. See, for example, Yamamoto et al., *Microbiol. Immunol.* 36:983, 1992; Krieg et al., Nature 374:546, 1995; Pisetsky, *Immunity* 5:303, 1996; and Zimmerman et al., *J. Immunol.* 160:3627, 1998.

As used herein, the terms "comprising," "including," and "such as" are used in their open, non-limiting sense.

The term "about" is used synonymously with the term "approximately." As one of ordinary skill in the art would understand, the exact boundary of "about" will depend on the component of the composition. Illustratively, the use of the term "about" indicates that values slightly outside the cited values, i.e., plus or minus 0.1% to 10%, which are also effective and safe. In another embodiment, the use of the term "about" indicates that values slightly outside the cited values, i.e., plus or minus 0.1% to 5%, which are also effective and safe. In another embodiment, the use of the term "about" indicates that values slightly outside the cited values, i.e., plus or minus 0.1% to 2%, which are also effective and safe.

"Isolated" (used interchangeably with "substantially pure") when applied to polypeptides means a polypeptide or a portion thereof, which has been separated from other proteins with which it naturally occurs. Typically, the polypeptide is also substantially (i.e., from at least about 70% to about 99%) separated from substances such as antibodies or gel matrices (polyacrylamide) which are used to purify it.

Compositions/Formulations

Provided herein are compositions (formulations) for oral immunotherapy of peanut flour protein.

A composition may comprise peanut flour, or alternatively, one or more proteins isolated from peanut flour, and optionally, may further comprise one or more diluents, one or more glidants, and one or more lubricants.

In one embodiment, a composition comprises peanut flour, or alternatively, one or more proteins isolated from peanut flour, one or more diluents, one or more glidants, and one or more lubricants.

A composition may contain, in one aspect, peanut flour, or alternatively, one or more proteins isolated from peanut flour. In one embodiment, peanut flour comprises Arah1, Arah2 and Arah6 proteins. In another embodiment, peanut flour contains as active ingredients: Arah1, Arah2 and Arah6 proteins.

In one embodiment, a composition comprises one or more diluents. "Diluents" for use in the formulations include, but are not limited to, alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), microcrystalline cellulose (e.g., Avicel®); silicified microcrystalline cellulse; microcrystalline dextrose; amylose; magnesium aluminum silicate; polysaccharide acids; bentonites; gelatin; polyvinylpyrrolidone/vinyl acetate copolymer; crosspovidone; povidone; starch;

pregelatinized starch; tragacanth, dextrin, a sugar, such as sucrose (e.g., Dipac®), glucose, dextrose, molasses, mannitol, sorbitol, xylitol (e.g., Xylitab®), lactose (e.g., lactose monohydrate, lactose anhydrous, etc.); dicalcium phosphate; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, a starch, e.g., a natural starch such as corn starch or potato starch, a pregelatinized starch such as Colorcon (Starch 1500), National 1551 or Amijel®, or sodium starch glycolate such as Promogel® or Explotab®; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and combinations thereof. In one embodiment, the formulation comprises microcrystalline cellulose or starch 1500. In another embodiment, the formulation comprises microcrystalline cellulose and starch 1500.

Suitable glidants (anti-caking agents) for use in the solid dosage forms described herein include, but are not limited to, colloidal silicon dioxide (Cab-O-Sil) and talc (e.g., Ultra Talc 4000). In one embodiment, the composition comprises Cab-O-Sil.

Suitable lubricants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and combinations thereof. In one embodiment, the composition comprises magnesium stearate. In another embodiment, the composition comprises sodium stearyl fumerate.

In some embodiments, a formulation may further comprise one or more filling agents. "Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and combinations thereof.

In one embodiment, a final formulation, comprises peanut flour (containing characterized peanut allergen proteins Ara h1, Ara h2 and Ara h6) formulated with a diluent, a glidant and a lubricant in graduated doses, comprising capsules containing 0.5 mg, 1 mg, 10 mg, 100 mg, 475 mg and 1000 mg each of peanut flour. Each capsule may be opened and the content mixed into taste-masking food immediately prior to administration.

In another embodiment, a final formulation, consists of peanut flour (containing characterized peanut allergen proteins Ara h1, Ara h2 and Ara h6) formulated with a bulking and a flow agent in graduated doses, comprising capsules containing 0.5 mg, 1 mg, 10 mg, 100 mg, 475, mg, 500 mg, or 1000 mg of peanut flour. Each capsule may be opened and the content mixed into taste-masking food immediately prior to administration.

In one embodiment, the dose of the composition is 0.5 mg and the concentration of Ara h1 comprises from about 0.035 to about 0.075 mg;

In another embodiment, the dose of the composition is 1.0 mg and the concentration of Ara h1 comprises from about 0.075 to about 0.15 mg;

In another embodiment, the dose of the composition is 10.0 mg and the concentration of Ara h1 comprises from about 0.5 to about 1.5 mg;

In another embodiment, the dose of the composition is 100.0 mg and the concentration of Ara h1 comprises from about 7.5 to about 15 mg; or In another embodiment, the dose of the composition is 475 mg and the concentration of Ara h1 comprises from about 35 to about 60 mg.

In one embodiment, dose of the composition is 0.5 mg and the concentration of Ara h2 comprises from about 0.035 to about 0.075 mg;

In another embodiment, the dose of the composition is 1.0 mg and the concentration of Ara h2 comprises from about 0.075 to about 0.175 mg;

In another embodiment, the dose of the composition is 10.0 mg and the concentration of Ara h2 comprises from about 0.5 to about 1.75 mg;

In another embodiment, the dose of the composition is 100.0 mg and the concentration of Ara h2 comprises from about 7.5 to about 15 mg; or In another embodiment, the dose of the composition is 475 mg and the concentration of Ara h2 comprises from about 45 to about 65 mg.

In one embodiment, the dose of the composition is 0.5 mg and the concentration of Ara h6 comprises from about 0.015 to about 0.06 mg;

In another embodiment, the dose of the composition is 1.0 mg and the concentration of Ara h6 comprises from about 0.025 to about 1.0 mg;

In another embodiment, the dose of the composition is 10.0 mg and the concentration of Ara h6 comprises from about 0.35 to about 1.0 mg;

In another embodiment, the dose of the composition is 100.0 mg and the concentration of Ara h6 comprises from about 3.5 to about 10 mg; or In another embodiment, the dose of the composition is 475 mg and the concentration of Ara h6 comprises from about 15 to about 40 mg.

In one embodiment, the percentage w/w of Ara h protein in a composition is as follows:

| | dose | | | | |
|---|---|---|---|---|---|
| Mg protein | 0.5 mg | 1.0 mg | 10 mg | 100 mg | 475 mg |
| mg peanut flour/composition | 1 | 2.06 | 20.64 | 200 | 1000 |
| mg peanut protein/composition | 0.5 | 1.03 | 10.32 | 100 | 500 |
| average mg Ara h 2/composition | 0.056 | 0.12 | 1.16 | 11.29 | 56.44 |
| mg Ara h 2/composition (high) | 0.061 | 0.13 | 1.27 | 12.29 | 61.45 |
| mg Ara h 2/composition (low) | 0.053 | 0.11 | 1.09 | 10.58 | 52.90 |
| average mg Ara h 6/capsule | 0.029 | 0.06 | 0.59 | 5.72 | 28.60 |

-continued

| Mg protein | dose | | | | |
|---|---|---|---|---|---|
| | 0.5 mg | 1.0 mg | 10 mg | 100 mg | 475 mg |
| mg Ara h 6/composition (high) | 0.032 | 0.06 | 0.65 | 6.30 | 31.50 |
| mg Ara h 6/composition (low) | 0.025 | 0.05 | 0.52 | 5.00 | 25.00 |
| average mg Ara h 1/ capsule | 0.050 | 0.10 | 1.03 | 9.96 | 49.81 |
| mg Ara h 1/composition (high) | 0.056 | 0.11 | 1.15 | 11.14 | 55.70 |
| mg Ara h 1/composition (low) | 0.044 | 0.09 | 0.91 | 8.82 | 44.10 |

In yet another embodiment, the ratio of Ara h2: Ara h6 in a composition after treatment with acid, base or oxidation is about 2. The degradation as measured by HPLC may be used as an indication of stability.

Amounts of Ara h proteins are based upon peanut protein being about 50% w/w of the flour and the ratio of Ara h proteins in the extractable protein is representative of the composition within the composition.

The active pharmaceutical agent may be initially sourced from raw peanuts, *Arachis hypogaea*, a member of the legume family. Raw peanuts are procured from multiple farming sources by, for example, the Golden Peanut Company, where the shelled, raw peanuts are processed into 12% defatted roasted peanut flour (PF). The PF may be further processed under cGMP conditions.

Under cGMP manufacturing conditions, the PF (approximately 50% peanut protein w/w) is formulated with a diluent, a glidant and a lubricant, and is subsequently encapsulated as 0.5, 1, 10, 100, 475, 500 or 1000 mg of peanut flour in size 3, 00 or 000 Hydroxypropyl Methyl Cellulose (HPMC) capsules.

The diluent provides the opportunity to formulate the low and high doses to contain adequate volume for dispersal from the opened capsule. The glidant and lubricant add flowability to the PF such that the capsule is easily emptied of flour by the subject. For clinical trials, the capsules will be bulk packed into amber colored bottles. At the time of use, capsule(s) containing CPNA will be opened and the content mixed into taste-masking food immediately prior to administration.

Compositions for use in the methods described herein include, but are not limited to, about 0.5 mg, about 1.0 mg, about 10.0 mg, about 100 mg, about 475 mg, about 500 mg, and/or about 1000 mg doses.

In one embodiment, a composition provided herein is contained within a capsule including, but not limited to a white opaque HPMC capsule shell (e.g., Capsugel) and may further contain, in some instances, a coloring agent (e.g., pigment blends, and/or color such as caramel color).

In one embodiment, a composition described herein comprises peanut proteins in a concentration from about 0.05% to about 100% w/w, or any integer therein. In another embodiment, a composition described herein comprises one or more peanut proteins in a concentration from about 0.1% to about 100% w/w. In another embodiment, a composition described herein comprises one or more peanut proteins in a concentration from about 0.5%, about 1%, about 2%, about 4%, or about 100% w/w. In another embodiment, a composition described herein comprises one or more peanut proteins in a concentration from about 0.7%, about 1.42%, about 3.93%, or about 100% w/w.

In one embodiment, a composition described herein comprises one or more peanut proteins in a target unit weight from about 0.5 mg/capsule to about 1100 mg/capsule, or any integer therein. In yet another embodiment, a composition described herein comprises one or more peanut proteins in a target unit weight from about 1.0 mg/capsule to about 1000 mg/capsule. In yet another embodiment, a composition described herein comprises one or more peanut proteins in a target unit weight of about 1.0 mg/capsule to about 2 mg/capsule, about 20 mg/capsule, about 200 mg/capsule, or about 1000 mg/capsule.

The concentration of diluent in a composition described herein may be from about 1% to about 99% w/w of the composition. In one embodiment, the concentration of diluent in a composition described herein may be from about 10% to about 90% w/w of the composition. For example, the diluent may be starch 1500 and the concentration may be about 9.86% to about 10% w/w of the composition.

The target unit weight of the diluent may be from about 10 to about 60 mg/capsule. For example, the diluent may be starch 1500 and the target unit weight may be about 14, about 14.5, or about 52.5 mg/capsule.

In one embodiment, the diluent may be microcrystalline cellulose and the concentration may be about 90% to about 60% w/w of the composition. For example, the diluent may be microcrystalline cellulose and the concentration may be about 88.66%, about 87.58%, about 85.07%, or about 65.66% w/w of the composition In one embodiment, the target unit weight of the diluent may be from about 100 to about 410 mg/capsule. For example, the diluent may be microcrystalline cellulose and the target unit weight may be about 125.55, about 126.99, about 446.61, or about 394 mg/capsule.

The concentration of glider in a composition described herein may be from about 0.01% to about 10% w/w of the composition. In one embodiment, the glider is Cab-O-Sil and the concentration of glider in a composition described herein may be about 0.01%, about 0.05%, about 0.1%, about 0.25%, about 0.5%, about 0.75%, about 1.0%, about 1.25%, or about 1.5% w/w of the composition.

The target unit weight of the glider may be from about 0.05 to about 5 mg/capsule. In one embodiment, the glider is Cab-O-Sil and the target unit weight is about 0.725, about 2.625 or about 3.0 mg/capsule.

The concentration of lubricant in a composition described herein may be from about 0.01% to about 10% w/w of the composition. In one embodiment, the lubricant is magnesium stearate and the concentration of lubricant in a composition described herein may be about 0.01%, about 0.05%, about 0.1%, about 0.25%, about 0.5%, about 0.75%, about 1.0%, about 1.25%, or about 1.5% w/w of the composition.

The target unit weight of the lubricant may be from about 0.05 to about 5 mg/capsule. In one embodiment, the lubricant is magnesium stearate and the target unit weight is about 0.725, about 2.625 or about 3.0 mg/capsule.

In one embodiment, a 0.5 mg composition comprises:

| Component: | Dose: 0.5 mg | |
|---|---|---|
| | Concentration % w/w | Target Unit Weight (mg/capsule) |
| Peanut flour | 0.70 | 1.0 |
| Starch 1500 | 9.86 | 14.0 |
| Microcrystalline cellulose | 88.66 | 125.55 |

-continued

Dose: 0.5 mg

| Component: | Concentration % w/w | Target Unit Weight (mg/capsule) |
|---|---|---|
| Cab-O-Sil | 0.50 | 0.725 |
| Magnesium stearate | 0.50 | 0.725 |
| Total | 100 | 142 |

In one embodiment, a 1.0 mg composition comprises:

Dose: 1.0 mg

| Component: | Concentration % w/w | Target Unit Weight (mg/capsule) |
|---|---|---|
| Peanut flour | 1.42 | 2.06 |
| Starch 1500 | 10.00 | 14.5 |
| Microcrystalline cellulose | 87.58 | 126.99 |
| Cab-O-Sil | 0.50 | 0.725 |
| Magnesium stearate | 0.50 | 0.725 |
| Total | 100 | 145 |

In one embodiment, a 10.0 mg composition comprises:

Dose: 10 mg

| Component: | Concentration % w/w | Target Unit Weight (mg/capsule) |
|---|---|---|
| Peanut flour | 3.93 | 20.64 |
| Starch 1500 | 10.00 | 52.5 |
| Microcrystalline cellulose | 85.07 | 446.61 |
| Cab-O-Sil | 0.50 | 2.625 |
| Magnesium stearate | 0.50 | 2.625 |
| Total | 100 | 525 |

In one embodiment, a 100.0 mg composition comprises:

Dose: 100 mg

| Component: | Concentration % w/w | Target Unit Weight (mg/capsule) |
|---|---|---|
| Peanut flour | 33.34 | 200.0 |
| Starch 1500 | 0 | 0 |
| Microcrystalline cellulose | 65.66 | 394.0 |
| Cab-O-Sil | 0.50 | 3.0 |
| Magnesium stearate | 0.50 | 3.0 |
| Total | 100 | 600 |

In one embodiment, a 100 mg formulation comprises a fill weight of 525 mg in a size 00 or 000 capsule. This formulation contains 38% Peanut Flour, 61% Microcrystalline Cellulose, 0.5% Cab-O-Sil, and 0.5% Magnesium Stearate.

In another embodiment, another 100 mg formulation was created by diluting the peanut flour with additional Microcrystalline cellulose. Fill weight was increased to 600 mg with a corresponding formulation consisting of 33% Peanut Flour, 66% Microcrystalline Cellulose, 0.5% Cab-O-Sil, and 0.5% Magnesium Stearate, resulting in improved flow characteristics and allowed for capsule weight to be maintained at a consistent level.

In one embodiment, a 500.0 mg composition comprises:

Dose: 475 mg

| Component: | Concentration % w/w | Target Unit Weight (mg/capsule) |
|---|---|---|
| Peanut flour | 100 | 1000 |
| Starch 1500 | 0 | 0 |
| Microcrystalline cellulose | 0 | 0 |
| Cab-O-Sil | 0 | 0 |
| Magnesium stearate | 0 | 0 |
| Total | 100 | 1000 |

It will be understood that quantitative formulas will be adjusted depending on manufacturing fill weights.

A "measurable serum concentration" or "measurable plasma concentration" describes the blood serum or blood plasma concentration, typically measured in mg, µg, or ng of therapeutic agent per ml, dl, or 1 of blood serum, absorbed into the bloodstream after administration. As used herein, measurable plasma concentrations are typically measured in ng/ml or µg/ml.

"Pharmacodynamics" refers to the factors which determine the biologic response observed relative to the concentration of drug at a site of action.

"Pharmacokinetics" refers to the factors which determine the attainment and maintenance of the appropriate concentration of drug at a site of action.

"Bioavailability" refers to the percentage of the weight of peanut allergen(s) dosed that is delivered into the general circulation of the animal or human being studied. The total exposure ($AUC_{(0-\infty)}$) of a drug when administered intravenously is usually defined as 100% Bioavailable (F %). "Oral bioavailability" refers to the extent to which peanut allergen(s) are absorbed into the general circulation when the pharmaceutical composition is taken orally as compared to intravenous injection.

"Blood plasma concentration" refers to the concentration of a peanut allergen(s) in the plasma component of blood of a subject. It is understood that the plasma concentration of peanut allergen(s) may vary significantly between subjects, due to variability with respect to metabolism and/or possible interactions with other therapeutic agents. In accordance with one aspect of the present invention, the blood plasma concentration of peanut allergen(s) may vary from subject to subject. Likewise, values such as maximum plasma concentration ($C_{max}$) or time to reach maximum plasma concentration ($T_{max}$), or total area under the plasma concentration time curve ($AUC_{(0-\infty)}$) may vary from subject to subject. Due to this variability, the amount necessary to constitute "a therapeutically effective amount" of peanut allergen(s) may vary from subject to subject.

"Carrier materials" include any commonly used excipients in pharmaceutics and should be selected on the basis of compatibility with peanut allergen(s) and the release profile properties of the desired dosage form. Exemplary carrier materials include, e.g., binders, suspending agents, disintegration agents, filling agents, surfactants, solubilizers, stabilizers, lubricants, wetting agents, diluents, and the like.

"Pharmaceutically compatible carrier materials" may comprise, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

"Plasticizers" are compounds which may be used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, dimethyl isosorbide and combinations thereof.

A "therapeutically effective amount" or "effective amount" is that amount of peanut allergen(s) to achieve a pharmacological effect. The term "therapeutically effective amount" includes, for example, a prophylactically effective amount. An "effective amount" of peanut allergen(s) is an amount effective to achieve a desired pharmacologic effect or therapeutic improvement without undue adverse side effects. The effective amount of a peanut allergen(s) will be selected by those skilled in the art depending on the particular subject and the disease level. It is understood that "an effect amount" or "a therapeutically effective amount" can vary from subject to subject, due to variation in metabolism, age, weight, general condition of the subject, the condition being treated, the severity of the condition being treated, and the judgment of the prescribing physician.

"Treat" or "treatment" as used in the context of an epilepsy-related disorder refers to any treatment of a disorder or disease related to epilepsy, such as preventing the disorder or disease from occurring in a subject which may be predisposed to the disorder or disease, but has not yet been diagnosed as having the disorder or disease; inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

"Absorption" typically refers to the process of movement of peanut allergen(s) from the gastrointestinal tract into a blood vessel.

The compositions described herein can be formulated for administration to a subject via any conventional means including, but not limited to, oral administration routes. As used herein, the term "subject" is used to mean an animal, preferably a mammal, including a human or non-human. The terms subject and subject may be used interchangeably. The formulations are for prevention and treatment of symptoms associated with exposure to limited amounts of peanut allergen in children and adults. In one embodiment, a subject is from about 4 to about 26 years of age.

In some embodiments, solid dosage forms may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder) a capsule (including both soft or hard capsules, e.g., capsules made from animal-derived gelatin or plant-derived HPMC, or "sprinkle capsules"), solid dispersion, solid solution, pellets, or granules. In other embodiments, the formulation is in the form of a powder. In still other embodiments, the formulation is in the form of a tablet, including but not limited to, a fast-melt tablet. Additionally, formulations may be administered as a single capsule or in multiple capsule dosage form. In some embodiments, the formulation is administered in two, or three, or four, capsules or tablets or capsules.

In some embodiments, solid dosage forms, e.g., tablets, effervescent tablets, and capsules, are prepared by mixing peanut flour comprising characterized peanut allergens with one or more pharmaceutical excipients to form a bulk blend composition. When referring to these bulk blend compositions as homogeneous, it is meant that the particles are dispersed evenly throughout the composition so that the composition may be readily subdivided into equally effective unit dosage forms, such as tablets, pills, and capsules. The individual unit dosages may also comprise film coatings, which disintegrate upon oral ingestion or upon contact with diluent. These formulations can be manufactured by conventional pharmacological techniques.

Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., *The Theory and Practice of Industrial Pharmacy* (1986). Other methods include, e.g., spray drying, pan coating, melt granulation, granulation, fluidized bed spray drying or coating (e.g., Wurster coating), tangential coating, top spraying, tableting, extruding and the like.

The pharmaceutical solid dosage forms described herein can comprise the compositions described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in *Remington's Pharmaceutical Sciences*, 20th Edition (2000), a film coating is provided around the formulation. In one embodiment, some or all of the particles are coated. In another embodiment, some or all of the particles are microencapsulated. In yet another embodiment, some or all of the peanut allergens are amorphous material coated and/or microencapsulated with inert excipients. In still another embodiment, the particles not microencapsulated and are uncoated.

Compressed tablets are solid dosage forms prepared by compacting the bulk blend formulations described above. In various embodiments, compressed tablets which are designed to dissolve in the mouth will comprise one or more flavoring agents. In other embodiments, the compressed tablets will comprise a film surrounding the final compressed tablet. In some embodiments, the film coating can provide a delayed release of the formulation. In other embodiments, the film coating aids in subject compliance (e.g., Opadry® coatings or sugar coating). Film coatings comprising Opadry® typically range from about 1% to about 3% of the tablet weight. In other embodiments, the compressed tablets comprise one or more excipients.

A capsule may be prepared, e.g., by placing the bulk blend formulation, described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulations are placed in a sprinkle capsule, wherein the capsule may be swallowed whole or the capsule may be opened and the contents sprinkled on food prior to eating. In some embodiments of the present invention, the therapeutic dose is split into multiple (e.g., two, three, or four) capsules. In some embodiments, the entire dose of the formulation is delivered in a capsule form.

In various embodiments, the particles and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In one aspect of the present invention, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with peanut allergens which sufficiently isolate peanut allergens from other non-compatible excipients. Materials compatible with peanut allergens are those that delay the release of the peanut allergens in vivo.

Exemplary microencapsulation materials useful for delaying the release of the formulations include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, Eudragit® NE30D, and Eudragit® NE 40D, cellulose acetate phthalate, sepifilms such as mixtures of HPMC and stearic acid, cyclodextrins, and mixtures of these materials.

Microencapsulated peanut allergens may be formulated by methods known by one of ordinary skill in the art. Such known methods include, e.g., spray drying processes, spinning disk-solvent processes, hot melt processes, spray chilling methods, fluidized bed, electrostatic deposition, centrifugal extrusion, rotational suspension separation, polymerization at liquid-gas or solid-gas interface, pressure extrusion, or spraying solvent extraction bath. In addition to these, several chemical techniques, e.g., complex coacervation, solvent evaporation, polymer-polymer incompatibility, interfacial polymerization in liquid media, in situ polymerization, in-liquid drying, and desolvation in liquid media could also be used. Furthermore, other methods such as roller compaction, extrusion/spheronization, coacervation, or nanoparticle coating may also be used.

The formulations described herein are administered and dosed in accordance with good medical practice, taking into account the clinical condition of the individual subject, the site and method of administration, scheduling of administration, and other factors known to medical practitioners.

Methods of Use

Compositions described herein may be used to treat using oral immunotherapy (OIT) a subject suffering from a peanut allergy.

Peanuts and peanut flour are common foods and additives found in many food products. The intended clinical use for Characterized Peanut Allergen (CPA) is found in relatively small quantities (0.5 to 4000 mg/dose) compared to quantities contained in food and will be delivered via the same route as orally ingested peanut-containing products.

Currently, preclinical studies exploring treatment modalities in food allergy animal models are limited. The principle model for induction of peanut allergy in mice is to expose mice by oral gavage to peanut proteins in the form of peanut butter, ground roasted peanuts, or purified peanut proteins, in combination with cholera toxin. After 3 to 6 weekly exposures the mice are challenged to demonstrate an allergic response. Mice may be challenged by intraperitoneal injection with sub-lethal doses of with a formulation described herein and scored for reaction severity. The intent is to demonstrate that the principle elicitors of anaphylaxis are specific Ara h proteins, rather than a combination of all peanut proteins. In an immunotherapy protocol, mice are treated with whole peanut extract, extract depleted of Ara h proteins, or with purified Ara h proteins alone. Upon challenge post treatment, changes in body temperature, symptom score and mouse mast cell protease-1 release mice may be assessed. Mice that are desensitized to further challenge may be treated with an entire extract or the Ara h protein combination.

The cellular requirements underlying peanut induced anaphylaxis may be determined explored in wild-type C57BL/6, B-cell deficient, CD40L-deficient, mast cell deficient or FcεRI ε-chain-deficient mice sensitized to peanut proteins. After intraperitoneal challenge with a formulation described herein, anaphylaxis is assessed by measurement of antigen-specific immunoglobulins (Igs), overall symptom score, body temperature, vascular permeability, mast cell mediator release and anaphylactic reactions. The B-cell, mast cell and CD40L deficient mice may be sensitized to peanut proteins as shown by production of IgE, and Th2-associated cytokines. The FcεRI ε-deficient mice may experience anaphylaxis albeit somewhat less severe than the wild-type animals.

In a model of esophago-gastro-enteropathy induced by long term feeding of peanuts to sensitized mice described by Mondoulet et al., 2012, epicutaneous immunotherapy with a formulation described herein may lessen the severity of gastro-intestinal lesions. (Mondoulet et al., 2012).

Data obtained from these models, which may demonstrate one or more of the hallmarks of human food allergic reactions, and are to be considered with respect to variability of human food allergy.

A subject treated with a composition described herein may exhibit a decreased anaphylactic reaction, relating to a decrease in clinical symptoms following treatment of symptoms associated with exposure to an anaphylactic allergen, which can involve exposure via cutaneous, respiratory, gastrointestinal, and mucosal (e.g., ocular, nasal, and aural) surfaces or a subcutaneous injection (e.g., via a bee sting) following treatment. In one embodiment, a subject may exhibit a decreased anaphylactic reaction of about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90% or more compared to a subject receiving a placebo or a subject not receiving treatment.

A subject treated with a composition described herein may exhibit a decreased humoral response and/or T cell response following treatment. In one embodiment, a subject may exhibit a decreased humoral response and/or T cell response of about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90% or more compared to a subject receiving a placebo or a subject not receiving treatment.

A subject treated with a composition described herein may exhibit a decreased IgE response and/or a decreased mast cell response following treatment. In one embodiment, a subject may exhibit a decreased IgE response and/or a decreased mast cell response of about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90% or more compared to a subject receiving a placebo or a subject not receiving treatment.

A subject treated with a composition described herein may be better able to withstand an oral food challenge (OFC) following treatment.

A subject treated with a composition described herein may be desensitized to peanut allergy following treatment. In one embodiment, a subject may be desensitized by about 2%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90% or more compared to a subject receiving a placebo or a subject not receiving treatment.

The compositions described herein may be administered in an escalation schedule. In one embodiment, escalating doses are administered to the subject on day 1 of treatment. For example, a subject may be administered, 1, 2, 3, 4 or 5 doses of a composition described herein on day 1. In another example, a subject may be administered 5 doses of a composition described herein in 30 minute increments on day 1. Subjects return on day 2 and receive a maximum tolerated dose. Subjects with moderate symptoms observed on day 2 may return on day 3 for the next lower dose under observation in the Clinical Research Center or monitored clinic setting. Subjects able to withstand treatment on the initial day of treatment may be administered one or more further doses of a composition described herein.

In one embodiment, a subject is further administered 1, 2, 3, 4, 5, 6, 7, 8 or 9 additional escalating doses of a composition described herein. The additional escalating doses may be administered to a subject in two-week intervals.

Following the final administration, the subject may, in some instances, be subject to an oral food challenge to determine if the subject has been desensitized to peanut allergy.

One non-limiting exemplary method is described herein:

| Initial Day Escalation Schedule | | |
| --- | --- | --- |
| Dose # | Peanut Protein Dose | Cumulative Peanut Protein Dose* |
| 1 | 0.5 mg | 0.5 mg |
| 2 | 1.0 mg | 1.5 mg |
| 3 | 1.5 mg | 3.0 mg |
| 4 | 3.0 mg | 6.0 mg |
| 5 | 6.0 mg | 12 mg |

*If no de-escalation

Doses are administered at a frequency standard of every 30 minutes.

Subjects at the end of the first day, tolerating less than 1.5 mg single dose, in some instances, may be considered an initial day escalation desensitization failure.

Subjects tolerating only a 1.5 or 3 mg single dose will go home on the greatest tolerated dose to be given daily (first dose given in Clinical Research Center under observation). All escalations will occur no sooner than 2 weeks and single dose increases in the Clinical Research Center from 1.5 to 3 to 6 mg will be attempted.

All subjects will return on Day 2 and receive their maximum tolerated dose under direct observation. Subjects with moderate symptoms observed on Day 2 will return on Day 3 for the next lower dose under observation in the Clinical Research Center or monitored clinic setting. Doses on day 2, 3 and 4 may be at least 1.5 mg or the subject, in some instances, may be considered an escalation failure.

Following the initial escalation, if a subject does not have an adverse event, the following dose schedule is followed:

| Escalation Dosing | | | |
| --- | --- | --- | --- |
| Dose # | Dose (Protein) | Interval (weeks) | % Increase |
| 6 | 12 mg | 2 | |
| 7 | 20 mg | 2 | 67% |
| 8 | 40 mg | 2 | 100% |
| 9 | 80 mg | 2 | 100% |
| 10 | 120 mg | 2 | 50% |
| 11 | 160 mg | 2 | 33% |
| 12 | 200 mg | 2 | 25% |
| 13 | 240 mg | 2 | 20% |
| 14 | 300 mg | 2 | 25% |

One or more additional exemplary dosing schedules are provided herein below in the examples.

In one embodiment of such methods, immediately prior to administration, an encapsulated capsule formulation may be broken apart and the ingredients mixed into taste-masking food.

Subjects may be monitored for onset of systemic symptoms including, for example, flushing, intensive itching on the skin, and sneezing and runny nose. Sense of heat, general discomfort and agitation/anxiety may also occur.

Provided herein is a method of desensitizing a subject suffering from a peanut allergy comprising administering one or more doses of a composition of any of the preceding claims on one more days to said subject.

In one embodiment, the subject is desensitized by at least about 2% compared to a subject administered a placebo or not receiving treatment.

In another embodiment, the subject exhibits a reduced humoral response and/or a reduced T cell response.

In another embodiment, the subject exhibits reduced anaphylaxis, a reduced mast cell response, a reduced IgE response, reduced hives, or a combination thereof.

In some embodiments, a composition described herein may be administered in conjunction with a food product.

A subject may be administered a composition described herein 1, 2, 3, 4 or 5 doses on a first day of treatment.

In one embodiment, a subject is administered 5 doses.

In another embodiment, the subject is administered said doses in 30 minute intervals.

The method may, in some instances further comprise one or more additional treatments.

In some embodiments, the one or more additional treatments comprise administration of a composition in two-week intervals.

In other embodiments, the one or more additional treatments comprise 1, 2, 3, 4, 5, 6, 7, 8, 9, or more doses of a composition.

Provided herein is a method of desensitizing a subject suffering from a peanut allergy comprising administering one or more doses of a composition of any of the preceding claims, said method comprising the following steps: (a) administering to said subject escalating doses of 0.5 mg, 1.0 mg, 1.5 mg. 3.0 mg, and 0.6 mg in 30-minute intervals on day 1 of the treatment regimen; (b) optionally, administering to said patient a maximum tolerated dose on day 2 of the treatment regimen; and (c) administering to said subject single doses of 12 mg, 20 mg, 40 mg, 80 mg, 120 mg, 160 mg, 200 mg, 240 mg, and 300 mg in two-week intervals.

In one embodiment, the method further comprises administering an oral food challenge (OFC) following completion of the treatment regimen.

Combination Therapies

The formulations and methods described herein may also be used in conjunction with other well known therapeutic reagents that are selected for their particular usefulness against the condition that is being treated. In general, the formulations described herein and, in embodiments where combinational therapy is employed, other agents do not have to be administered in the same formulation, and may, because of different physical and chemical characteristics, have to be administered by different routes. The determination of the mode of administration and the advisability of administration, where possible, in the same formulation, is well within the knowledge of the skilled clinician. The initial administration can be made according to established protocols known in the art, and then, based upon the observed effects, the dosage, modes of administration and times of administration can be modified by the skilled clinician.

The particular choice of compounds used will depend upon the diagnosis of the attending physicians and their judgment of the condition of the subject and the appropriate treatment protocol. The compounds may be administered concurrently (e.g., simultaneously, essentially simultaneously or within the same treatment protocol) or sequentially, depending upon the condition of the subject, and the actual choice of compounds used. The determination of the order of administration, and the number of repetitions of administration of each therapeutic agent during a treatment protocol, is well within the knowledge of the skilled physician after evaluation of the severity of peanut allergy being treated and the condition of the subject.

It is understood that the dosage regimen to treat, prevent, or ameliorate peanut allergy, can be modified in accordance with a variety of factors. These factors include the age, weight, sex, diet, and/or medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In some embodiments, the formulation is administered with at least one other antihistamine agent, corticosteroid, beta agonist, anti-inflammatory agent, an anti-IgE antibody (e.g., omalizumab) and/or epinephrine.

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art without departing from the embodiments; it should be understood that various alternatives to the embodiments described herein may be employed in practicing the methods described herein.

Example 1: Oral Desensitization to Peanut in Peanut-Allergic Children and Adults Using Characterized Peanut Allergen (CPNA) Oral Immunotherapy (OIT) [ARC 001]

| | |
|---|---|
| Title | Oral Desensitization to Peanut in Peanut-Allergic Children and Adults using Characterized Peanut Allergen (CPNA) Peanut Oral Immunotherapy (OIT) |
| Short Title | CPNA Peanut OIT |
| Number of Subjects | 50 peanut allergic subjects will be randomized 1:1 to peanut OIT versus placebo. |

| | |
|---|---|
| Study Design | This is a multi-center, randomized, double-blind placebo-controlled study of efficacy and safety of characterized peanut OIT in peanut allergic individuals. All eligible subjects will receive an escalating dose of characterized peanut allergen or placebo. At or around 6 months, all eligible and enrolled subjects on active therapy will have an extra 250 mg dose of peanut protein (measured as 500 mg of flour) administered to test for desensitization, and all eligible and enrolled placebo subjects will have a placebo challenge dose, to maintain double-blinding. All subjects will continue up-dosing afterwards per protocol ARC002. Those subjects not passing at 6 months will be re-challenged with 250 mg of peanut protein (measured as 500 mg of flour) at 7 months, and those again not passing will be re-challenged at 8 and/or 9 months. When ≥80% of subjects on active treatment have passed the peanut flour challenge, the placebo patients will undergo a 2 gm OFC to test for desensitization, and then be switched to active treatment per protocol ARC002. |
| Study Duration | From 6 up to 9 months |
| Primary Endpoint | The primary end point is percent of patients desensitized to peanut challenge. |
| Secondary Endpoints | The safety of peanut OIT based on dosing symptoms and reported adverse events including serious adverse events
Changes in peanut-specific IgE and IgG4, changes in SPT mean wheal diameters. |
| Study Product and Design | Characterized Peanut Allergen. Doses characterized and normalized for total protein and specific peanut allergen ratios will ascend per the protocol given below. Study product will be provided in break-apart capsules formulated to 0.5, 1.0, 10 or 100 mg of peanut protein. |
| Inclusion Criteria | Age 4 through 26 years
Serum IgE to peanut of >0.35 $kU_A/L$ [determined by UniCAP ™ within the past 12 months] and/or a SPT to peanut >3 mm compared to control
Experience dose-limiting symptoms at a cumulative dose of ≤125 mg of peanut protein (measured as 250 mg of peanut flour) on screening OFC
Written informed consent from adult subjects
Written informed consent from parent/guardian for minor subjects
Written assent from minor subjects as appropriate (i.e., above the age of seven years)
Female subjects of child-bearing potential must use birth control |
| Exclusion Criteria | History of cardiovascular disease
History of other chronic disease (other than asthma, atopic dermatitis, or rhinitis) requiring therapy (e.g., heart disease, diabetes)
History of eosinophilic gastrointestinal disease
Current participation in any other interventional study
Subject is on 'build-up phase" of immunotherapy to another allergen (i.e., has not reached maintenance dosing)
Severe asthma (2007 NHLBI Criteria Steps 5 or 6, see Appendix 2)
Mild or moderate (2007 NHLBI Criteria Steps 1-4) asthma with any of the following criteria met:
    FEV1 <80% of predicted, or FEV1/FVC <75%, with or without controller medications (only for age 6 or greater and able to do spirometry) or
    ICS dosing of >500 mcg daily fluticasone (or equivalent inhaled corticosteroids based on NHLBI dosing chart) or
    1 hospitalization in the past year for asthma or ER visit within the past six months
Use of steroid medications (IV, IM or oral) in the following manners
    history of daily oral steroid dosing for >1 month during the past year or
    burst or steroid course in the past 3 months or
    >2 burst oral steroid course in the past year
Inability to discontinue antihistamines for the initial day of escalation, skin testing or OFC
Use of omalizumab within the past six months, or current use of other non-traditional forms of allergen immunotherapy (e.g., oral or sublingual) or immunomodulator therapy (not including corticosteroids)
Use of β-blockers (oral), angiotensin-converting enzyme (ACE) inhibitors, angiotensin-receptor blockers (ARB) or calcium channel blockers
Pregnancy or lactation |

| | | | | | | | |
|---|---|---|---|---|---|---|---|
| Treatment Description | All eligible subjects will receive a peanut OFC. Those subjects who have dose-limiting symptoms to a cumulative dose of 125 mg of peanut protein (measured as 250 mg of peanut flour) or less will be randomized to active treatment or placebo. Subjects will receive daily oral dosing of CPNA or placebo OIT. Ideally, subjects will on Day 1 escalate to 6 mg followed by 26-weeks of escalation on a biweekly basis. Therapy details are found below. After at least 6 months of up-dosing therapy and at least 2 weeks after up-dosing to the 300 mg dose, an additional dose of 250 mg of peanut protein (measured as 500 mg of peanut flour) will be administered to those subjects on active therapy to test for desensitization. Those on placebo will be administered a placebo challenge. Up-dosing per protocol ARC 002 will then continue. Those not passing the 6 month challenge will be re-challenged at 7 months; those not passing at 7 months will be re-challenged at 8 and/or 9 months. At such time that ≥80% of subjects on active pass challenge with 250 mg peanut protein (500 mg peanut flour), subjects will be unblinded, and a 1 gm cumulative peanut protein (measured as 2 gm of peanut flour) OFC will be performed to test for desensitization among the placebo patients. Placebo subjects will then be switched to active, and all subjects will be eligible for a longer-term safety dose escalation protocol (protocol ARC002). All escalation doses occur in a Clinical Research Center or monitored setting. | | | | | | |
| Study Procedures | The following procedures will be performed according to the schedules in Appendix 1: Medical and allergy history (including dietary history) Physical examination Spirometry at baseline Peak flow rates Pregnancy tests Plasma analysis for IgE and IgG4 to peanut (UniCAP ™) Oral food challenge to peanut Blood draws pre- and post-OFC for those subjects ≥30 kg Skin prick test Study product administration Initial day escalation Oral Immune Therapy (OIT) Build up and maintenance OIT | | | | | | |

Schedule of Events

| Procedure | Visit 00 Screening | Visit 00A Baseline | Blood draw (5-10 days post-OFC) | Visit 01 Initial Escalation Days 1-3[1] | Study Product Build-up[2] | Visit 02 3 month (12 weeks) | Visit 03 6-9 months (active patients passing challenge) | Blood draw (5-10 days post OFC, placebos) |
|---|---|---|---|---|---|---|---|---|
| Medical/Allergy History | X | | | | | X | X | |
| Spirometry | | X | | | | | | |
| Physical Exam | X | | | | | | | |
| Peak Flow Rate[3] | X | X | | | | | X | |
| Pregnancy Test[4] | X | X | | | | X | X | |
| Diet History | X | | | X | | X | X | |
| Targeted History/Physical Exam | | X | | X | X | X | X | |
| Blood draw for those ≥30 kg | | X | X | | | | | X |
| Peanut specific IgE, IgG4 | X | | | | | | X | |
| SPT | X | | | | | | X | |
| Clinical Research Center Peanut OIT Administration[5] | | | | X | X | X | | |
| Daily Home administration[6] | | | | X | X | X | X | |
| Oral food challenge-1 gm peanut protein (all subjects) | | X | | | | | | |
| Oral food challenge-1 gm peanut protein (placebo subjects) | | | | | | | X | |

| Procedure | Visit 00 Screening | Visit 00A Baseline | Blood draw (5-10 days post-OFC) | Visit 01 Initial Escalation Days 1-3[1] | Study Product Build-up[2] | Visit 02 3 month (12 weeks) | Visit 03 6-9 months (active patients passing challenge) | Blood draw (5-10 days post OFC, placebos) |
|---|---|---|---|---|---|---|---|---|
| Passing challenge of 250 mg protein (500 mg of flour) administered as a single dose, 3-8 hours after the usual daily maintenance dose | | | | | | | X | |

[1]Peanut OIT subjects will have initial escalation to at least 1.5 mg on Day 1, return Day 2, return Day 3 if symptoms, return for dose escalation every 2 weeks.
[2]Peanut OIT subjects will have escalation visits every 2 weeks, unless epinephrine is administered as described below. Phone calls will occur 1 week after each escalation visit to assess dosing compliance and symptoms.
[3]Only prior to any OFC, at baseline, a peak flow rate may be performed if spirometry results cannot be obtained
[4]For females of childbearing age.
[5]In Clinical Research Center or monitored clinic setting.
[6]Daily home dosing for peanut OIT with characterized peanut allergen 1. Peanut OIT 1.1 Rationale for Selection of Study Population The study will enroll 50 subjects from 4 to 26 years old. All subjects enrolled must undergo an initial DBPCFC to peanut that must be positive at a cumulative dose of 125 mg of peanut protein (measured as 250 mg of peanut flour) or less, regardless of how they were initially diagnosed as peanut allergic. This will enroll subjects that are sensitive to peanut exposure and expected to benefit from desensitization to the equivalent of a whole peanut, and corresponds to a specific level of allergen exposure conducted during the enrollment oral food challenge. The lower cutoff of 4 years of age was selected due to the fact that patients affected the most severely by peanut allergy ingestion are generally children, and for sufficient developmental maturity to comply with study protocols, given parental assistance. The upper age limit of 26 years was selected to insure that the patients do not have underlying cardiovascular conditions that could preclude the use of epinephrine in subjects exposed to the risk of anaphylaxis.

1.2 Rationale for Selection of Study Drug Regimen

The rationale for dosing builds on the work of the Consortium of Food Allergy Research (CoFAR) and its investigators. The dosing consists of a single-day initial escalation at very low doses, followed by a build-up phase of dose escalation, with a single escalation occurring every 2 weeks. This has been demonstrated to be well tolerated and efficacious in previous studies and will be used in this current trial.

1.3 Known and Potential Risks and Benefits to Human Participants 1.3.1 Risks

Peanut is a commonly-consumed food and as such has a well understood safety profile. Except for allergic reactions in patients with peanut allergy, it does not cause discernible side effects in humans.

In patients with peanut allergy, there have been many oral immunotherapy studies performed using procedures and dosing similar to those proposed in this Phase 2 study. In general, safety profile has been very good across the studies, and based on those studies approximately 80%, 15% and <1% of the subjects are expected to have a mild, moderate or severe symptoms, respectively, during some point in their dosing with the peanut immunotherapy. It is important to note that essentially all adverse events have been allergy-related, predictable, and reversible. The only major atypical adverse event has been a single reported case of eosinophilic esophagitis, reversible upon stopping dosing.

Specifically, the buildup and daily maintenance doses of peanut OIT may cause allergic symptoms including sneezing, rhinorrhea, urticaria, angioedema, flushing, flares of eczema, ocular, nasal, oral and/or throat pruritus, nausea, vomiting, abdominal discomfort, cough, wheezing and/or shortness of breath in addition to severe anaphylaxis. The likelihood of a subject experiencing any allergic symptoms is expected to be lessened by initiating dosing at extremely small amounts of characterized peanut allergen and by buildup dosing under observation in a clinical setting until the maintenance dose is achieved.

Oral food challenges may induce an allergic response. Allergic reactions can be severe including life-threatening allergic reactions; however, the risk of an allergic reaction is reduced by initiating the challenge with a very small amount of the food, gradually increasing the dose, and stopping the challenge at the first sign of a reaction. If subjects have an allergic reaction during the challenges, they may need oral, intramuscular, or intravenous medications (subjects will have an IV catheter placed before the OFCs). Trained personnel, including a physician, as well as medications and equipment, will be immediately available to treat any reaction. The anticipated rate of serious life threatening anaphylactic reactions would be <0.1%.

There may be a risk that during participation in the trial the subjects may decrease their vigilance against accidental peanut ingestion because they believe they are protected from it. This phenomenon has been reported in previous trials, and subjects in the trial will be warned that they should continue to practice their usual vigilance against accidental ingestion of peanuts or peanut-containing foods.

1.3.2 Benefits

The immediate benefits for the subject include the potential decrease in the subject's reactivity to peanuts after an accidental ingestion of peanut.

2. Objectives 2.1 Primary Objective

Demonstrate the efficacy of Characterized Peanut Allergen through reduction in clinical reactivity to limited amounts of peanut allergen in peanut-allergic children and young adults (ages 4-26).

2.2 Secondary Objective(s)

Demonstrate the safety of Characterized Peanut Allergen as measured by incidence of adverse events and dosing symptoms.

Evaluate the immunological effects of peanut OIT therapy.

3. Study Design

Subjects age 4 through 26 years with a serum IgE to peanut of >0.35 kUA/L and/or a SPT to peanut of >3 mm versus control will be screened. All eligible subjects will undergo initial double blind placebo controlled peanut OFC. Those who have dose-limiting symptoms at a cumulative dose of <125 mg of peanut protein (measured as 250 mg of peanut flour) will be enrolled into the study, since they would be expected to benefit from protection against limited amounts of allergen exposure. Those who successfully consume >250 mg of peanut flour during the OFC will be considered to be screen failures and will be followed per local standard of care.

Fifty (50) subjects who pass screening will be randomized 1:1 to active peanut protein or placebo. Randomization will be stratified by the maximally tolerated dose during screening.

Subjects will escalate their OIT dose biweekly for six months, up to an expected daily dose of 300 mg of peanut protein in subjects able to tolerate up-dosing.

Clinical data and blood samples will be collected at pre-specified intervals. If a subject is removed from therapy because of failing escalation or build-up the subject will continue to be followed for safety.

The characterized peanut allergen/placebo OIT treatment is comprised of an initial escalation day, an initial build-up phase to last approximately 24 weeks to achieve a dose of at least 300 mg/day, with a maintenance of the last dose for 2 weeks, and followed at approximately week 26 by a challenge dose of an additional 250 mg of peanut protein (measured as 500 mg of peanut flour) for those on active therapy and a placebo challenge for the placebo subjects. Subjects on active therapy will subsequently continue with up-dosing per protocol ARC002, while placebo patients will continue on placebo. Any patients on active therapy not tolerating the week 26 challenge will be re-challenged again with 250 mg of peanut protein (measured as 500 mg of peanut flour) at week 30; those not tolerating that challenge will again continue up-dosing as tolerated and be re-challenged again at week 34 and/or week 38. At such time as ≥80% of patients on active therapy tolerate challenge with 250 mg of peanut protein (measured as 500 mg of peanut flour), all subjects will be unblinded, the placebo subjects switched to active, and the placebo patients administered a 1 gm cumulative peanut OFC (measured as 2 gm of peanut flour). The active-arm challenge is to assess protection against approximately one peanut's worth of peanut protein, since accidental exposures are typically to limited amounts of allergen. Passing this challenge with no more than mild clinical symptoms would be associated with de-sensitization to at least a total daily dose of 550 mg of peanut protein (300 mg maintenance dose+250 mg challenge). Since subjects are enrolled only if they are sensitive to 125 mg or less on the enrollment oral food challenge, this would represent a nearly 5× increment in the dose tolerated, which (given a six-month treatment period) is in line with the previous CoFAR demonstration of a 10× increment after treatment for one year. The placebo challenge maintains double-blinding during assessment, while the exit OFC for placebo patients will be a standard OFC to assess potential desensitization off therapy, and due to safety considerations since these subjects will not have had anything but potential accidental exposure to allergen since enrolling in the trial (i.e., they will not have been administered desensitization OIT).

Dosing Schedule for Peanut OIT

| Initial Day Escalation Schedule | | |
|---|---|---|
| Dose # | Peanut Protein Dose | Cumulative Peanut Protein Dose* |
| 1 | 0.5 mg | 0.5 mg |
| 2 | 1.0 mg | 1.5 mg |
| 3 | 1.5 mg | 3.0 mg |
| 4 | 3.0 mg | 6.0 mg |
| 5 | 6.0 mg | 12 mg |

*If no de-escalation; Frequency standard every 30 min

Subjects at the end of the first day tolerating less than 1.5 mg single dose will be considered an initial day escalation desensitization failure.

Subjects tolerating only 1.5 or 3 mg single dose will go home on the greatest tolerated dose to be given daily (first dose given in Clinical Research Center under observation). All escalations will occur no sooner than 2 weeks and single dose increases in the Clinical Research Center from 1.5 to 3 to 6 mg will be attempted.

All subjects will return on Day 2 and receive their maximum tolerated dose under direct observation.

Subjects with moderate symptoms observed on Day 2 will return on Day 3 for the next lower dose under observation in the Clinical Research Center or monitored clinic setting.

Doses on day 2, 3 and 4 must be at least 1.5 mg or the subject will be considered an escalation failure.

| Escalation Dosing | | | |
|---|---|---|---|
| Dose # | Dose (Protein) | Interval (weeks) | % Increase |
| 6 | 12 mg | 2 | |
| 7 | 20 mg | 2 | 67% |
| 8 | 40 mg | 2 | 100% |
| 9 | 80 mg | 2 | 100% |
| 10 | 120 mg | 2 | 50% |
| 11 | 160 mg | 2 | 33% |
| 12 | 200 mg | 2 | 25% |
| 13 | 240 mg | 2 | 20% |
| 14 | 300 mg | 2 | 25% |

Capsules are to be opened and contents sprinkled over an age-appropriate food.

Those subjects who achieve a dose of 300 mg of peanut protein during the initial build-up period will continue maintenance therapy before challenge until 6 months of total treatment. Those subjects who achieve less than 300 mg of peanut protein during this initial buildup phase will continue up-dosing as tolerated, and have their assessment challenge two weeks after they are able to achieve and maintain a 300 mg dose. Those unable to achieve a dose of at least 300 mg of peanut protein by 36 weeks will be considered an endpoint failure.

Follow-up Assessment is conducted at 6 months:

Those on active treatment will take their usual daily dose of peanut protein on the day of their assessment. They will be given in clinic within 4-8 hours later an extra 250 mg dose of peanut protein (measured as 500 mg of peanut flour) to mimic an accidental exposure and will be observed for reactions. Those that experience mild or less symptoms will be considered a success. All others will be considered a failure.

For those on placebo, a placebo challenge will be performed to maintain double-blinding during assessment. At such time as ≥80% of patients on active tolerate challenge, a 2 gm (cumulative) peanut flour OFC will be performed to identify potentially desensitized individuals in the placebo group. Because it is unlikely that the placebo subjects will be desensitized, it would not be safe to give them a full challenge dose of 300 mg of peanut protein. For that reason an OFC is a safer way to measure their then-existing desensitization state.

Those patients on active not tolerating challenge will continue up-dosing per protocol ARC002, and will be re-challenged with 250 mg of peanut protein (measured as 500 mg peanut flour) at 7 months. Those patients again not tolerating challenge will continue up-dosing, and be re-challenged at 8 and/or 9 months. (After 9 months, the up-dosing amount per protocol ARC002 is ≥200 mg, so patients not tolerating challenge at that point would also not be tolerating up-dosing, and would be counted as treatment failures in any event). Once ≥80% of patients on active are able to tolerate challenge, the study subjects will have completed the protocol and will be eligible to participate in a follow-on open label treatment protocol (ARC002) to continue further up-dosing or to switch from placebo to active treatment.

Study Design Safety Considerations

The design considers important safety issues:

All dose escalations will be supervised in the clinic;

The peanut OIT will only escalate to a maximum 6 mg single dose during the initial escalation on day 1;

OFC can delineate individuals who can ingest peanut safely in a supervised setting;

Dosing symptoms and adverse events will be captured throughout the study;

All subjects will be provided with an epinephrine auto-injector and will be trained in its use;

Subjects will be cautioned against consuming any peanuts or peanut-containing foods other than Characterized Peanut Allergen while on study;

Subjects will be tested against a limited amount of additional allergen to assess the degree of actual protection afforded while consuming less than portion-size maintenance doses;

Subjects will be tested against placebo at or before inevitable un-blinding due peanut taste and smell;

Patients will be offered the option to continue up-dosing in an un-blinded manner;

While this study continues the CoFAR practice of sprinkling allergen over an age-appropriate food before consumption, the HPMC capsules in which the Characterized Peanut Allergen is provided are ingestible and pharmaceutical grade. Therefore, after the appropriate follow-on studies to compare sprinkling over food vs. direct ingestion of capsules, this approach may in future provide an easier route to compliance for continued allergen exposure in those desensitized subjects still averse to peanut taste or smell.

3.1 Primary Efficacy Outcome Measure

The primary clinical efficacy end-point is the proportion of subjects who achieve desensitization within 6-9 months as determined for active therapy subjects by tolerating at least 250 mg of peanut protein (measured as 500 mg of peanut flour) as a single dose with no more than mild symptoms or for placebo subjects as tolerating, without dose limiting symptoms, a cumulative OFC dose greater than or equal to 250 mg of peanut protein (measured as 475-500 mg of peanut flour).

3.2 Secondary Endpoints

The secondary outcome measures are as follows:

The safety of peanut OIT as measured through dosing symptoms, adverse events and serious adverse event.

Changes in peanut-specific IgE and IgG4, changes in SPT mean wheal diameters.

4. Selection and Withdrawal of Subjects 4.1 Inclusion Criteria

Subjects who meet all of the following criteria are eligible for enrollment as study subjects:

Age 4 through 26 years;

Serum IgE to peanut of >0.35 kUA/L [determined by UniCAP™ within the past 12 months] and/or a SPT to peanut >3 mm compared to control;

Experience dose-limiting symptoms at a cumulative dose of <125 mg of peanut protein (250 of peanut flour) on screening OFC;

Written informed consent from adult subjects;

Written informed consent from parent/guardian for minor subjects;

Written assent from minor subjects as appropriate (e.g., above the age of seven years); and Use of birth control by female subjects of child-bearing potential 4.2 Exclusion Criteria Subjects who meet any of these criteria are not eligible for enrollment as study subjects:

History of cardiovascular disease

History of other chronic disease (other than asthma, atopic dermatitis, or rhinitis) requiring therapy (e.g., heart disease, diabetes)

History of eosinophilic gastrointestinal disease

Current participation in any other interventional study

Subject is on 'build-up phase" of immunotherapy for another allergen (i.e., has not reached maintenance dosing)

Severe asthma (2007 NHLBI Criteria Steps 5 or 6, see Appendix 2)

Mild or moderate (2007 NHLBI Criteria Steps 1-4) asthma with any of the following criteria met:

(a) FEV1<80% of predicted, or FEV1/FVC<75%, with or without controller medications (only for age 6 or greater and able to do spirometry) or ICS dosing of >500 mcg daily fluticasone (or equivalent inhaled corticosteroids based on NHLBI dosing chart) or 1 hospitalization in the past year for asthma or ER visit within six months.

(b) Use of steroid medications (IV, IM or oral) in the following manners: history of daily oral steroid dosing for >1 month during the past year or burst or steroid course in the past 3 months or >2 burst oral steroid course in the past year.

(c) Inability to discontinue antihistamines for the initial day of escalation, skin testing or OFC.

(d) Use of omalizumab within the past six months, or current use of other non-traditional forms of allergen immunotherapy (e.g., oral or sublingual) or immunomodulator therapy (not including corticosteroids).

(e) Use of beta-blockers (oral), angiotensin-converting enzyme (ACE) inhibitors, angiotensin-receptor blockers (ARB) or calcium channel blockers.

(f) Pregnancy or lactation.

4.3 Premature Subject Termination from the Study 4.3.1 Criteria

Any subject may be prematurely terminated from additional allergen exposures for the following reasons: anaphylaxis resulting in hypotension, neurological compromise or mechanical ventilation secondary to peanut OIT dosing or any peanut food challenge Any subject deemed to have severe symptoms and receives aggressive therapy at any time should be discontinued from further therapy, including the following:

Poor control or persistent activation of secondary atopic disease (e.g., AD, asthma);

Started on ARBs, ACE, beta-blockers, or other prohibited medications, with no alternative medications available per the prescribing doctor;

Pregnancy;

Circumstances (e.g., concurrent illness, such as gastroenteritis) requiring missed peanut OIT maintenance dosing of >7 consecutive days; or Non-adherence with home peanut OIT dosing protocol (excessive missed days; i.e., >3 consecutive days missed on 3 or more occasions) would be a safety issue warranting discontinuation.

Any subject may be prematurely terminated from the study if: The subject elects to withdraw consent from all future study activities, including follow-up; The subject is "lost to follow-up" (i.e., no further follow-up is possible because attempts to reestablish contact with the subject have failed); The subject develops biopsy-documented eosinophilic esophagitis (EoE); or The subject dies.

4.3.2 Follow-Up of Subjects Who Discontinue Treatment Only

Subjects who prematurely discontinue treatment with peanut OIT will remain in the study until normal termination. All willing subjects will be followed for the duration of the study to monitor safety and efficacy parameters.

5. Study Medication 5.1 Formulation, Packaging and Labeling

The study product is characterized peanut allergen as peanut flour, formulated with a bulking agent and a flow agent in pre-measured graduated doses, comprising capsules containing 0.5 mg, 1 mg, 10 mg and 100 mg each of peanut protein with established ratios of key peanut allergens. The capsule or capsules will be opened, rolled gently and tapped lightly to ensure full delivery of the contents, and mixed with food prior to ingestion by the subject.

All study product will be packaged and labeled at the central manufacturer. Study drug will be shipped by the drug depot to the site pharmacist for distribution to the site study personnel. The site pharmacist will dispense study drug in a manner consistent with the current dose level and treatment assignment. The product will be labeled with the numbered dose level and package number.

5.2 Preparation, Administration and Dosage

The drug product will be provided pre-packaged from the site pharmacy in appropriate doses to deliver the specified dose. The contents may be added to apple juice, applesauce, yogurt, pudding or other age-appropriate food. The food may not be heated before consumption, and must also be one to which the subject is not additionally allergic. The capsules should be drawn apart, and gently rolled between finger and thumb, followed by a light tap to ensure full delivery of contents. The product must be consumed promptly after mixing. If there is a delay of more than 24 hours in consumption, the product will be discarded and a new product dose mixed and consumed. Every attempt will be made to administer the dose of study drug at the same time of day. A target interval of at least 12 hours should pass between doses.

5.3 Assessment of Compliance with Study Treatment and Monitoring

Families will document daily dosing and any reaction from at-home dosing by diary logs. Central monitoring of compliance will be performed.

5.4 Modification of Study Treatment

As described in the protocol, peanut OIT doses may be adjusted by the study physician if the subject is unable to tolerate the scheduled dose increase.

5.5 Concomitant Medications

All subjects may continue their usual medications, including those taken for asthma, allergic rhinitis and atopic dermatitis, during the study. However, they must be able to discontinue antihistamines prior to the initial day of escalation, skin testing and oral food challenges. Usual topical steroid use is permitted at the time of skin testing. Oral steroid use longer than three weeks at one time is not allowed, and no up-dosing should occur within 3 days of oral steroid use.

5.6 Rescue Medications

Treatment of individual allergic reactions during peanut OIT therapy should be with either an antihistamine and/or epinephrine, along with IV fluids, albuterol and steroids as indicated. Subjects and parents are likely to already have EpiPens®, but for those who do not, EpiPens® or an equivalent device will be provided. Subjects and parents will be trained in proper use and will be able to demonstrate proper technique with the EpiPens®.

5.7 Prohibited Medications

Prohibitied medications include: Omalizumab (Xolair); Systemic (oral) corticosteroids used for any greater than a total of 3 weeks duration throughout the study. If used, subjects must not be up-dosed until at least 3 days after ceasing the administration of oral steroids; beta-blockers (oral); Angiotensin-converting enzyme (ACE) inhibitors; Angiotensin-receptor blockers (ARB); and Calcium channel blockers.

6. Study Procedures 6.1 Enrollment and Randomization

Subjects will have an initial screening peanut OFC. Those reacting to ≤125 mg of peanut protein (250 mg of peanut flour) will be randomized in a 1:1 ratio to peanut OIT or placebo. Those able to successfully consume >250 mg of peanut flour during their OFC will not be eligible for the study and will be treated according to local standard of care. Randomization will be done via the project data system. If accrual capacity is adequate, each of the expected 8-10 sites should enroll approximately 5 subjects each. Entry slots will be reassigned if accrual completion would be delayed because of slow accrual at a given site. Because of the requirement for the peanut OFC, the screening and baseline visits may be conducted in more than 1 day.

6.2 Screening Visit

The screening visits which may occur over several days (Visit 00) will include the following procedures: Consent and assent; Diet and allergy questionnaire; Physical examination; Blood draw for peanut-specific IgE and IgG4 measurement; Physical examination; Skin prick test to peanut extract; and Pregnancy test, if applicable.

6.3 Baseline Visit

Subjects who meet eligibility criteria will return for a baseline visit (Visit 00A). This visit will include the following procedures and will take place over several days:

Targeted history and physical examination;

Pregnancy test, if applicable;

Peak Flow Rate (PFR);

Blood draw (pre-OFC) for mechanism analysis by ITN (the Immune Tolerance Network);

2 gm (cumulative) peanut flour (1 gm peanut protein) OFC; and

Spirometry*. * Spirometry is attempted in all subjects greater than 6 years of age. For subjects age 6-11, if valid spirometry results are not successfully obtained, the attempt is documented and peak flow measures will be accepted for the entry criteria with results >80% of predicted. For subjects 4 through 5 yrs, peak flow rate will be attempted but the results are not required to move forward if they are unable to perform reliably. The attempt must be documented. A clinical assessment is required.

6.4 Study Treatment Visits

Peanut OIT Treatment Overview:

Peanut OIT administration will include an initial escalation day (Visit 01) with peanut oral immunotherapy dosing beginning at 0.5 mg with graduated doses up to 6 mg (if tolerated) occurring in the Clinical Research Center or appropriate monitored clinic setting. Subjects at the end of day 1 tolerating less than 1.5 mg single dose will be considered an initial day escalation desensitization failure. Subjects return on day 2 for an observed dose and will continue dosing based on the symptoms experienced as described in later in this section. This initial dosing will be followed by peanut OIT escalation every 2 weeks in the Clinical Research Center or monitored clinic setting.

With each escalation, phone contact will occur after the first week on home dosing to assess symptoms and compliance. A targeted history and physical exam will be performed at each visit. Subjects will be assessed for exacerbation of atopic dermatitis or asthma (as determined by active wheezing) prior to each in clinic dosing.

In addition to dosing visits, subjects will return to the Clinical Research Center at 5-10 days after the entry OFC for post-OFC blood draw, at 3 months (Visit 02) for follow-up and at 6 months or later (Visit 03) for their assessment challenge or OFC. A medical and diet history, and physical exam will also be performed at these visits.

At 6 months either a single 250 mg peanut protein dose (measured as 500 mg of peanut flour) (active therapy) or a placebo challenge will be performed, within 3-8 hours of the subject's usual maintenance dose at least two weeks after their last up-dosing. A history, diet history, skin prick test and physical exam will be performed. For those patients on active not tolerating challenge, up-dosing will continue per protocol ARC 002 below, but they will be re-challenged with 250 mg peanut protein (measured as 500 mg peanut flour) at 7 months. Those not tolerating re-challenge at 7 months will continue up-dosing as tolerated and be challenged again at 8 and/or 9 months. At such time as ≥80% of the active treatment cohort is able to tolerate a 500 mg peanut flour challenge, the study will be un-blinded and a 2 gm cumulative flour OFC will be conducted in the placebo group, with blood draws pre-OFC and 5-10 days subsequently. The placebo group will then be switched over to active, and de-sensitized in similar manner as the active group in this protocol (detailed in protocol ARC002).

Peanut OIT:

Initial Dose Escalation—the initial day will be done at the Clinical Research Center (or equivalent monitored clinic setting) and consist of peanut OIT dosing, beginning at 0.5 mg with graduated doses every 30 minutes up to 6 mg (if tolerated) on day 1. Subjects will not have active wheezing or a current flare of atopic dermatitis. If symptoms occur which prevent escalation to 6 mg, the highest tolerated dose (at least 1.5 mg) will be accepted as the "desensitization" dose for further escalation (See FIG. 1). The maximum tolerated dose on day 1 (e.g. 1.5, 3 mg, or 6 mg) will be given on day 2 as a single dose under observation at the Clinical Research Center. If moderate symptoms occur on day 2, the subject will return to the Clinical Research Center on day 3 for the next lower dose (must be at least 1.5 mg) under direct observation. If moderate symptoms re-occur, consultation with the Medical Monitor is warranted to determine the next course of action. If symptoms prevent initial escalation desensitization dosing to 3 mg, the subject will be dropped from active treatment due to desensitization failure and followed longitudinally.

Subjects tolerating 1.5 mg, 3 mg, or 6 mg will go home to remain on that dose daily and then will return every 2 weeks to the Clinical Research Center for single dose escalation. Subjects will be called 1 week after each dose escalation visit to assess for dosing compliance and dose reactions. Subjects should withhold their daily home dose on the escalation day but should take all other scheduled medications. Note that the daily home dose should be taken as part of a meal. It is recommended that the dose be taken at a consistent time (within a 4-hour time period), and it is critical to take the dose every day. Doses should be separated by at least 12 hours. Subjects who require dosing reduction during the 2-week period will reset their 2-week escalation schedule to maintain the new dose for a 2-week period prior to attempting to escalate again. Any dose escalation attempts may be postponed for 1-2 extra weeks based on clinical judgment. An escalation attempt must be made by 4 weeks, unless escalation is delayed due to administration of epinephrine as defined below. Failure to successfully escalate for three consecutive attempts will result in the subject being withdrawn from further therapy. The subject will be followed for the remainder of the study for safety and immunologic monitoring. (See schedule for initial day dose escalation, FIG. 1) A physician will be available at all times during any of the Clinical Research Center peanut OIT dosing visits.

Subjects may have clear liquids or JELL-O during the day of the initial day escalation protocol while they are being given the desensitization doses.

Reactions to Peanut OIT During Initial Escalation

Process algorithm for symptoms during the initial escalation protocol. (See FIG. 1). Subjects may develop symptoms during the initial escalation protocol, similar to those seen during other desensitization protocols (e.g., venom immunotherapy, drug desensitization). The investigator's judgment will be required to determine the best course of action with possible actions being the following: extension of time interval between dosing (additional 30 minutes); Return to previously tolerated dose (i.e., repeat of last tolerated dose) then advance forward; or Discontinuation of desensitization protocol.

For oral/pharyngeal pruritus—the action should be to continue the normal dosing in 30 minutes.

For mild symptoms, defined as:

Skin—limited or localized hives/swelling, skin flushing or pruritus;

Respiratory—rhinorrhea/sneezing, nasal congestion, occasional cough, throat discomfort; or GI—mild abdominal discomfort/minor episode of vomiting.

Depending on the physician's discretion, the action should be either: repeat the last dose in 30-60 min or advance in 30-60 minutes.

If moderate symptoms occur, defined as:

Skin—systemic hives/swelling;

Respiratory—throat tightness without hoarseness, persistent cough, wheezing without dyspnea; or GI—persistent moderate abdominal pain/cramping/nausea, increased vomiting.

The action should be to implement a 30-60 minute observation period and then proceed with a reduced dose

[decrease by 1-2 dosing steps] only if prior symptoms resolve. If symptoms continue or worsen, the subject can be treated with antihistamines (see below). If symptoms resolve, repeat the same or reduced dose, and then continue. If symptoms require additional treatment, then consultation with the Medical Monitor as listed on the cover page of the protocol is warranted to determine the next course of action. The Medical Monitor will be available for questions and decision making for any questions related to the study protocol at all times.

If more severe symptoms occur, defined as:

Respiratory—laryngeal edema, throat tightness with hoarseness, wheezing with dyspnea;

GI—significant severe abdominal pain/cramping/repetitive vomiting;

Neurological—change in mental status;

Circulatory—hypotension;

The action should be: discontinue the initial day escalation and administer the appropriate rescue medications.

If the subject requires treatment for symptoms during the initial escalation protocol with antihistamines on one occasion, then the rest of the initial escalation may be followed. If the subject requires more than two medications (e.g., albuterol, diphenhydramine, epinephrine, or others) or multiple doses of antihistamines, the initial escalation should be terminated and the subject would not receive further OIT. For a completed initial escalation with no symptoms or only mild symptoms, subjects should have a 2-hour post-protocol observation period. For moderate to severe symptoms, the observation period should be at least 4 hours, and up to 24 hours, based on symptoms and treatment regimen needed to stabilize.

Day 2 after Initial Dose Escalation

All subjects will return for the next dose to the clinic after the initial day escalation. This dose will be the previous day's dose or the last tolerated dose from the initial day escalation. The maximum dose is 6 mg. The minimum dose for the second day is 1.5 mg.

Those subjects administered: 6 mg: if tolerated, return home on that dose for 2 weeks until the next escalation; or if not tolerated, return for day 3 dosing with a 1 or 2 step reduction Those subjects administered: 1.5-3 mg: if tolerated, return home on that dose for 2 weeks until next escalation; or if not tolerated, return the next day with a 1 or 2 step reduction (if at 1.5 mg and require a dose reduction, that subject is considered an escalation failure and followed as a longitudinal control).

Day 3 after Initial Dose Escalation

Those subjects with moderate symptoms on day 2 will return on day 3 for an observed dose. The maximum dose would be 6 mg, the minimum dose 1.5 mg.

Those subjects administered: 1.5-6 mg: if tolerated, return home on that dose for 2 weeks until next escalation; or if not tolerated, call the Medical Monitor for further management Build-Up Phase Subjects will begin the Clinical Research Center dosing scheme as outlined until 300 mg of peanut is reached. Subjects will return for a supervised dose escalation in the clinic every 2 weeks. Subjects are called 1 week after each dose escalation visit to assess for dosing compliance and dose reactions. Any dose escalation attempts may be postponed for 1-2 extra weeks based on clinical judgment. An escalation attempt must be made by 4 weeks. Subjects should withhold their daily home dose on the escalation day but should take all other prescribed medications. Note that the daily home dose should be taken as part of a meal. It is recommended that the dose be taken at a consistent time (within a 4-hour time period), and it is critical to take the dose every day. Doses should be separated by at least 12 hours. Subjects who require dosing reduction during the 2-week period will reset their 2-week escalation schedule to maintain the new dose for a 2-week period prior to attempting to escalate again.

Should significant systemic symptoms, which may include mild symptoms based on physician discretion or moderate or greater symptoms, be reported during the daily home dosing, the symptom/dosing algorithm is followed (See FIG. 2) to determine the best course of action. The appropriate treatment will depend on the type and number of symptoms. If significant symptoms occur consistently following three attempts to increase the daily oral dose in the Clinical Research Center or clinic with each attempt spaced 2-4 weeks apart, dosing escalation are halted at the last tolerated dose, the subject continued on that dose as their maintenance dose and at the 2 gm peanut flour OFC when performed.

Subjects are allowed to take their other daily medications during the build-up and maintenance phases of the study (i.e., antihistamines, albuterol).

Figure 2:
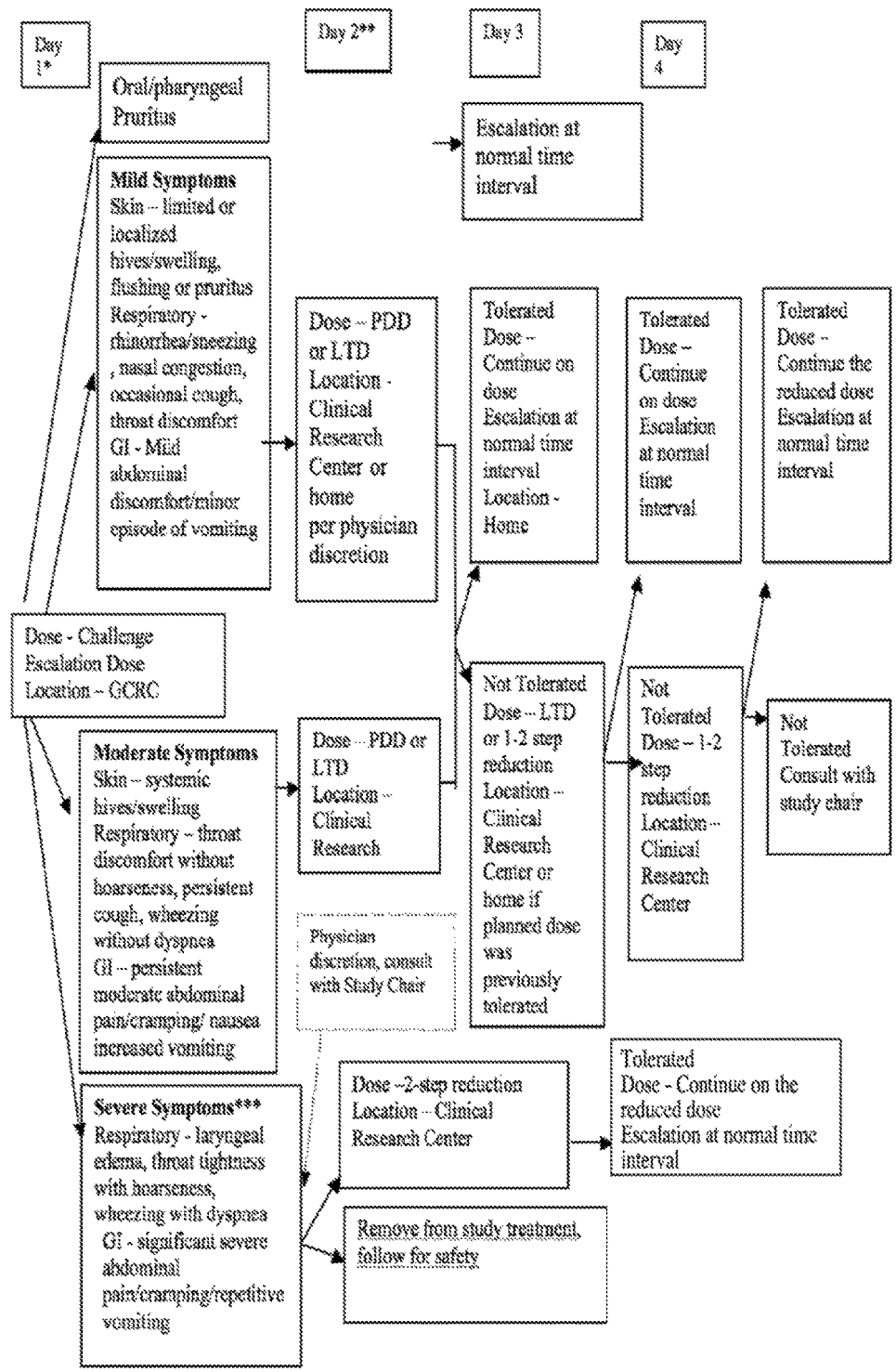
FIG. 2 Schematic for Build Up Phase Dose Escalation—Day of Symptom. Tolerated—Symptoms no greater than oral/pharyngeal pruritus; LTD—Last Tolerated Dose; PDD—Previous Days Dose; Clinical Research Center or monitored clinic setting; Failure of dose escalation in 3 consecutive attempts—maintain dose at LTD; * Day 1—Refers to the escalation dose day only (initial or build-up, symptoms observed in the clinic);  Day 2—After symptoms in the Clinical Research Center or at home; * Subjects in the initial day escalation with severe symptoms are considered an escalation failure and will be followed as a longitudinal control.
Figure 3:
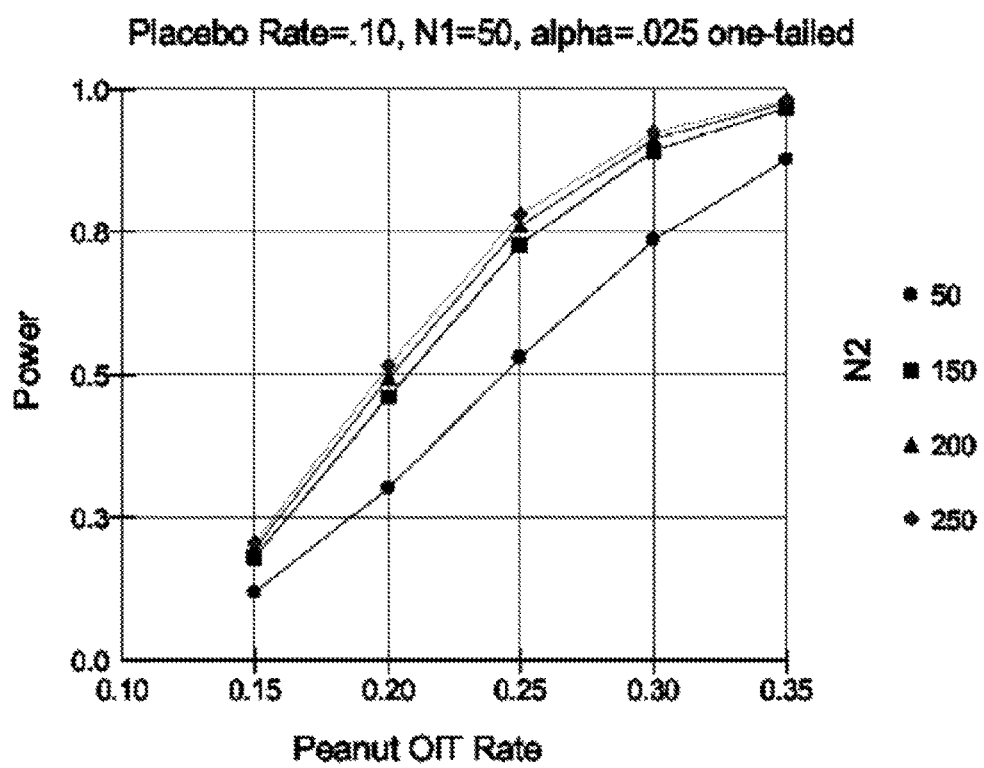
FIG. 3 illustrates s study size of 250 individuals randomly assigned at a 4:1 ratio of active:placebo has been selected for the study. The unbalanced ratio permits economical observation of both active arm therapy characteristics and safety events. As designed, power (y axis) exceeds 90% if the true peanut OIT response rate (x axis) exceed 30%.

Process algorithm for symptoms during build-up phase for Peanut OIT (pre 6 month assessment). (FIG. 2).

Subjects are free from active wheezing or a flare of atopic dermatitis prior to any dose escalation. Subjects are maintained on their current dose of study product until their flare of asthma or atopic dermatitis resolve. Subjects are cautioned against activities likely to increase reactivity (e.g., exercising or taking hot showers or baths within 4 hours after dosing). At the physician's discretion, temporary reduction to half of prior dose levels can be recommended while subjects are suffering from symptoms of an upper respiratory infection or influenza, or during menses. Subjects may develop symptoms during dosing for the build-up phase. The investigator's judgment will be required to determine the best course of action with possible actions being the following:

1. Continue with daily home dosing;
2. Continue the same daily dose for the rest of the 2-week interval, with 50% of the dose split between doses given 8-12 hours apart;
3. Return for repeat dosing in Clinical Research Center;
4. Return for dosing of previously tolerated dose (without escalation) in Clinical Research Center; or
5. Discontinuation of dosing If a subject has a dose escalation in the Clinical Research Center without symptoms, the action should be to continue per protocol with daily home dosing of the tolerated dose with the next escalation visit to the Clinical Research Center 2 weeks later.

If the subject only experiences oral/pharyngeal pruritus during the administration of the daily dose, then the same dose can be repeated the next day at home and continued throughout the interval unless other symptoms begin to develop (see below).

For mild symptoms, defined as:

Skin—limited or localized hives/swelling, skin flushing or pruritus;

Respiratory—rhinorrhea/sneezing, nasal congestion, occasional cough, throat discomfort; or GI—mild abdominal discomfort/minor episode of vomiting The action should be either to repeat the dose the next day (day 2) at home or to have the subject return to the Clinical Research Center the next day (day 2) for a repeat of the previous day's dose or the last tolerated dose (at the physician's discretion). If the dose is tolerated, then the subject will continue on that dose and return at the normal interval. If the dose causes mild symptoms again, then the subject may return to the Clinical Research Center (day 3) and be given the last tolerated dose or a 1-2 step dose reduction. If tolerated, the subject will continue on this dose for the normal time interval. If mild symptoms recur, a 1-2 step reduction should be administered the next day (day 4). If tolerated then that dose should be continued for 2 weeks. If not tolerated, consultation with the Medical Monitor should be indicated.

If moderate symptoms occur, defined as:

Skin—systemic hives/swelling;

Respiratory—throat tightness without hoarseness, persistent cough, wheezing without dyspnea; or GI—persistent moderate abdominal pain/cramping/nausea, increased vomiting The action should be to have the subject return to the Clinical Research Center the next day (day 2) for dosing with the previous days dose or the last tolerated dose under observation. If the dose is tolerated, the subject will continue on that daily home dose for the normal time interval per protocol. If the subject does not tolerate this dose, the subject should receive the last tolerated dose or a 1-2 step dose reduction (day 3) in the Clinical Research Center or at home if the planned dose was previously tolerated. If this dose is tolerated, it will be continued as the daily home dose for the normal time interval, then escalation attempted in the Clinical Research Center as noted below. If this dose is not tolerated, then the next dose will be a 1-2-step reduction in dosing, and the dose will be given on the Clinical Research Center (day 4). If this next dose is not tolerated, then a discussion with the Medical Monitor will ensue to make a decision about whether to continue the subject on active treatment in the study.

If more severe symptoms occur, defined as:

Respiratory—laryngeal edema, throat tightness with hoarseness, wheezing with dyspnea; or GI—significant severe abdominal pain/cramping/repetitive vomiting.

The action should be to treat the subject, and at the physicians discretion either 1) have them return to the Clinical Research Center the next day (day 2) for dosing with a 2-step reduction in dose under observation or 2) discontinue them from the active treatment. If the subject tolerates the dose reduction, then they will remain on that dose for 2 weeks and then return to the Clinical Research Center for the dose escalation. A discussion with the Medical Monitor may ensue to make a decision about whether to continue the subject on active treatment in the study.

If a subject fails dose escalation after three consecutive (with 2-4 weeks between) attempts, he/she will be considered a dose escalation failure and the last tolerated dose will be accepted as the maintenance dose. For a completed dose escalation with no symptoms, subjects should be observed for 30 minutes. For mild symptoms, subjects should have a 1-2 hours post-protocol observation period. For moderate to severe symptoms, the observation period should be at least 4 hours and up to 24 hours based on symptoms and treatment regimen needed to stabilize the subject.

Any subject deemed to have severe symptoms including hypoxia, hypotension or change in mental status (stage 3 defined in Appendix 3) and receives aggressive therapy at any time should be discussed with the Medical Monitor and discontinued from active therapy.

For specific questions related to dosing escalation or continuation of the same dose that are not answered in the above protocol, a Medical Monitor is available for questions and decision-making.

Any subject who discontinues build-up dosing due to repeated allergic reactions to the characterized peanut allergen will have his/her mechanistic blood drawn within approximately 1 week of discontinuation of therapy.

6.4.1 Treatment for Reactions During the Build-Up and Maintenance Phases

Treatment of individual reactions should be with either an antihistamine and/or epinephrine, along with IV fluids, albuterol, and steroids as indicated. Generally, for mild and moderate symptoms, the subject should receive antihistamines, and for more severe symptoms, the subjects should receive epinephrine, antihistamines, and then the other medications as indicated. If severe anaphylaxis (stage 3 defined in Appendix 3) occurs at any time, dose escalation will stop and the dose is reduced to the last tolerated dose and the subject continued on that dose as long-term maintenance without further escalation.

Antihistamines

If a subject receives antihistamines only, the dose escalation can be continued. If symptoms during a build-up day require antihistamines in multiple doses or in combination with other medications (except epinephrine), there should be a dose reduction by 1-2 doses with the next dose given in the CRC. If dose escalation fails or requires treatment after two more escalation attempts each spaced 2 to 4 weeks apart, the dose should be reduced to the last tolerated dose and continued long term without further escalation.

Epinephrine

Any reaction (in clinic or at home) that requires two or more doses of epinephrine will halt further dose escalation for this individual. Maintenance on the last tolerated dose would be continued.

Clinic

If a single administration of epinephrine is required during in clinic escalation, the dose should be reduced by two doses, and the subject continued on that dose for four weeks. After 4 weeks at the reduced dose, an escalation attempt may be tried in clinic.

If a single administration of epinephrine is required a second consecutive time during this escalation attempt, the dose should be reduced by two doses, and the subject continues on that dose for 6-8 weeks. After 6-8 weeks at the reduced dose, an escalation attempt may be tried in clinic.

If a single administration of epinephrine is required a third consecutive time during this escalation attempt, the dose should be reduced by two doses and the subject continued on that dose as long-term maintenance without further escalation.

Home

If a single administration of epinephrine use occurs during dosing at home, this epinephrine use is not counted as one of the uses described above, unless severe anaphylaxis occurs at home. The subject should return to clinic for an observed dose prior to resuming any dosing at home.

Maintenance Phase

This phase consists of the subject receiving the maximum achieved daily dose of peanut OIT. The subject will continue to follow a peanut-restricted diet for the duration of the study. For any noted symptoms during the maintenance phase, the same study dosing rules for the build-up phase are followed.

Updose Assessment:

At 6 months, either a single 250 mg peanut protein dose (measured as 500 mg peanut flour) (active therapy) or a placebo challenge (for placebo subjects) is performed while on therapy. For those subjects not tolerating challenge, up-dosing will continue as tolerated, and subjects are re-challenged at 7 months. For those subjects not tolerating challenge at 7 months, up-dosing will continue and subjects are challenged again at 8 and/or 9 months. After 8-9 months, up-dosing increments are ≥200 mg, and so 250 mg peanut protein challenges would be expected to be tolerated, or the subject could not be up-dosed.

Missed Peanut OIT Doses at any Phase of the Study:

Missed Peanut OIT doses at any phase of the study can pose a significant risk to the enrolled subjects. The algorithm for missed consecutive doses is as follows:

(1) Miss one dose—The next dose would be the current dose and could be given at home;

(2) Miss two doses in a row—The next dose would be the current dose and could be given at home;

(3) Miss three doses in a row—The next dose would be the current dose and would be given under observation (Clinical Research Center);

(4) Miss four doses in a row—The next dose would be the current dose and would be given under observation (Clinical Research Center);

(5) Miss five to seven doses in a row—For those subjects on peanut OIT, initiate the next dose as approximately 25% of the last tolerated dose. This would be done under observation (Clinical Research Center). Dose escalation would occur in the Clinical Research Center with an escalation no sooner than weekly and no longer than every 4 weeks with dose increases of 1-dose levels at each escalation. If symptoms occur, the dosing symptom rules in the build-up phase would apply;

(6) Missing more than seven consecutive days of therapy constitutes an individual stopping rule and the subject would no longer take active therapy but would be followed longitudinally; and (7) Additionally; excessive missed peanut OIT doses, i.e., >3 consecutive days missed on 3 occasions, constitutes an individual stopping rule and the subject would no longer take active therapy but would be followed longitudinally.

6.5 Oral Food Challenge, Double Blind Placebo Controlled

The subjects are off antihistamines for an appropriate length of time (5 half-lives of the antihistamine that is being used). Oral food challenges are undertaken under direct medical supervision in a Clinical Research Center or food challenge area with emergency medications and staff immediately available and will follow established study procedures. Prior to the OFC, subjects are assessed for an exacerbation of asthma as determined by active wheezing or a peak expiratory flow rate <80% of predicted. A uniform approach for food challenges is used. Frequent assessments are made for symptoms affecting the skin, gastrointestinal tract, and/or respiratory tract. Dose limiting symptoms, typically objective symptoms, indicate a positive reaction and termination of dosing.

6.6 Peanut OFC

All peanut OFCs conducted in the study are double blind placebo controlled food challenges. The OFC is performed by feeding gradually increasing amounts of the suspected food under physician observation. OFC is conducted as 2 challenges during a single day visit or over 2 days using placebo for one challenge and peanut for the other. If conducted in a single day, at least 2 hours must separate the first half of the challenge from the second half of the challenge. The challenge is performed so that neither the subject, nor the subject's caregiver nor the physician knows which challenge contains the peanut or the placebo.

The initial OFC for eligibility will consist of a cumulative dose of 2 gm of the peanut flour (1 gm of peanut protein) or placebo in gradually increasing doses at 15-30 minute intervals. If successfully passed the subject would not be eligible for the study. The doses for the cumulative 2 gm peanut flour OFC (1 gm peanut protein) are 1, 4, 20, 50, 75, 100, 250, 475, 500, and 1000 mg of peanut flour (containing 0.5, 2, 10, 50, 37.5, 50, 125, 250, 475 and 500 mg of peanut protein).

The exit 2 gm peanut flour (1 gm peanut protein) OFC for the placebo subjects will be done while on therapy and is not followed by a repeat OFC or open feeding. Although these minimum standards have been used safely in the past, the investigator may use clinical judgment to increase the intervals between doses; or repeat lower doses, if there is a concern that a reaction may be developing. The doses for the 2 gm peanut flour (1 gm peanut protein) OFC are 1, 4, 20, 50, 75, 100, 250, 475, 500, 1000 mg of peanut flour. Though many published challenges begin with 5 mg of peanut flour for an initial dose, the minimum dose for this study was chosen to be 1 mg of peanut flour (0.5 mg of peanut protein), according to additional recent recommendations and consensus.

Subjects are considered to have tolerated the OFC if they do not experience dose-limiting symptoms.

6.7 Skin Prick Test

Subjects will have skin prick tests performed using study approved procedures for food allergens. While the subject is off antihistamines for an appropriate length of time (5 half-lives of the antihistamine that is being used), a skin test probe is pressed through a commercial extract of an allergen into the epidermis. Positive (histamine) and negative (saline-glycerin) controls are placed to establish that the response is not blocked and to determine if there is dermatographism, respectively.

7.8 Visit Windows

Dosing schedule should be adhered to strictly. Two days before, or five days after a planned dosing visit, is an acceptable window with continued daily dosing of the current dose level. Study visits for scheduled blood draws or OFC should take place within 2 weeks of the scheduled visit.

6.9 Study Blinding Procedures

The study is double-blinded up to the exit OFC assessment. All oral food challenges are performed in a double-blind manner.

7. Safety Monitoring

This section defines the types of adverse events that should be reported and outlines the procedures for appropriately collecting, grading, recording and reporting them.

7.1 Definitions

All safety events observed under this protocol are reported through the data system for the duration of the study. Safety events related to accidental food exposure are recorded on a Food Allergy Episode form and are not reported on an adverse event form unless the event is considered a serious adverse event, as defined below. Any systemic allergic symptoms due to dosing will be recorded on a Study Product Administration form. If the event meets the definition of a serious adverse event, it will also be recorded on an adverse event (AE)/serious adverse event (SAE) form. Skin prick test and food challenge reactions that occur in the clinic are captured on study specific forms and are not reported on an adverse event form unless the event is considered a serious adverse event, as defined below. All serious adverse events are reported on the AE/SAE form set in addition to the Skin Prick form or an Oral Food Challenge form if the event occurred during one of these procedures. All other safety events that occur throughout the study are reported on the AE/SAE form set.

7.2 Food Allergy Episodes

In order to report the occurrence of a safety event associated with accidental food ingestion, subjects will be instructed to contact the site study coordinator or investigator for any adverse event. The subject may be asked to return to the site. A Food Allergy Episode form will be completed for each of these events in addition to events where consumption of peanut without a reaction occurs. If the accidental food ingestion safety event meets the definition of a serious adverse event, as defined below, the AE/SAE form will be completed as well.

7.3 Definitions 7.3.1 Adverse Event (AE) or Medical Event

An adverse event is any untoward medical occurrence in humans, whether or not considered drug related which occurs during the conduct of a clinical trial. Any change in clinical status, ECGs, routine labs, x-rays, physical examinations, etc., that is considered clinically significant by the study investigator is considered an AE.

Suspected adverse reaction is any adverse event for which there is a reasonable possibility that the drug caused the adverse event. A reasonable possibility implies that there is evidence that the drug caused the event.

Adverse reaction is any adverse event caused by the drug.

7.3.2 Serious Events (Serious Adverse Events, Serious Suspected Adverse Reactions or Serious Adverse Reactions)

A serious adverse event including a serious suspected adverse reaction or serious adverse reaction as determined by the Investigator or the sponsor is any event that results in any of the following outcomes: Death; Life-threatening AE information, such as safety information provided in the package insert, the investigational plan, the investigator's brochure or the protocol.

7.4 Data Monitoring

Although the safety of peanut is well established, a Committee will meet every 3 months to evaluate unblinded efficacy and safety data, and will be empowered to recommend termination in the event that unexpected safety issues arise. The DMC will also determine at what point ≥80% of active patients have tolerated a 250 mg peanut protein challenge, resulting in unblinding and the exit OFC for the placebo cohort.

7.5 Toxicity Grading

The study site assigns toxicity grades to indicate the severity of adverse experiences and toxicities. The CoFAR adopted usage of NCI-CTCAE v 4.0 for application in adverse event reporting and will likewise be used for this protocol. We define allergic reactions in this protocol beyond the NCI-CTCAE system, and further characterize anaphylaxis. Anaphylaxis is characterized as mild, moderate, or severe in Appendix 3, independent of the toxicity grade associated with the event. Toxicity grading for allergic reactions including anaphylaxis is modified from the NCI-CTCAE system to be more appropriate for this study population, and is displayed in Appendix 4. We reviewed the NCI-CTCAE v 4.0 specifically for this protocol and it is otherwise appropriate for this study population. The purpose of using the NCI-CTCAE system is to provide standard language to describe toxicities and to facilitate tabulation and analysis of the data and assessment of the clinical significance of treatment-related toxicities.

The NCI-CTCAE provides a term and a grade that closely describes the adverse event. Each participating site will receive copies of the grading scales and event descriptions.

Record adverse events not included in the NCI-CTCAE listing and grade them 1 to 5 according to the General Grade Definition provided below:

| | | |
|---|---|---|
| Grade 1 | Mild | Transient or mild discomforts (<48 hours), no or minimal medical intervention/therapy required, hospitalization not necessary (non-prescription or single-use prescription therapy may be employed to relieve symptoms, e.g., aspirin for simple headache, acetaminophen for post-surgical pain). |
| Grade 2 | Moderate | Mild to moderate limitation in activity, some assistance may be needed; no or minimal intervention/therapy required, hospitalization possible. |
| Grade 3 | Severe | Marked limitation in activity, some assistance usually required; medical intervention/therapy required, hospitalization possible. |
| Grade 4 | Life-threatening | Extreme limitation in activity, significant assistance required; significant medical/therapy intervention required, hospitalization, or hospice care probable. |
| Grade 5 | Death | Death |

(Life-threatening means that the study subject was, in the opinion of the investigator or sponsor, at immediate risk of death from the reaction as it occurred.); Inpatient hospitalization or prolongation of existing hospitalization; Persistent or significant incapacity or substantial disruption of the ability to conduct normal life functions; Congenital abnormality or birth defect; or Important medical event that may not result in one of the above outcomes, but may jeopardize the health of the study subject or require medical or surgical intervention to prevent one of the outcomes listed in the above definition of serious event.

7.3.3 Unexpected Adverse Event

An adverse event is "unexpected" when its nature (specificity) or severity is not consistent with applicable product For additional information and a printable version of the NCI-CTCAE v. 4.03 manual, consult the NCI-CTCAE website, http://ctep.cancer.gov/reporting/ctc.html.

7.6 Adverse Events Collection Procedures

Adverse events will be evaluated from the onset of the event until the time the event is resolved or medically stable, or until 30 days after the subject completes study treatment, whichever comes first.

AEs may be discovered through any of these methods: Observing the subject; Questioning the subject, which should be done in an objective manner; Receiving an unsolicited complaint from the subject; Review of medical records/source documents; and/or Review of home dosing symptom logs (provided to record symptoms between visits

7.6.1 Recording and Reporting Procedures

A multi-page adverse event form will be used allowing all adverse events to be submitted through a single reporting mechanism. Serious adverse events will require additional information reported on additional pages within the Internet data entry system. Source documents can be scanned and attached to the adverse event form as well. The investigator will treat subjects experiencing adverse events appropriately and observe them at suitable intervals until their symptoms resolve or their status stabilizes.

7.6.2 SAE Recording and Reporting Procedures

Serious adverse events will be recorded on the adverse event case report form (CRF). All centers are obligated to report SAEs within 24 hours of their occurrence and/or the sites knowledge of the event to the Coordinating Center. The following attributes will be assigned: description; date of onset and resolution (if known when reported); severity; assessment of relatedness to test article; and action taken.

The site investigator will apply his/her clinical judgment to determine whether an adverse event is of sufficient severity to require that the subject be removed from treatment. If necessary, an investigator will suspend any trial procedures and institute the necessary medical therapy to protect a subject from any immediate danger.

Subsequent review by FDA, the DMC, ethics review committee or IRB, or the sponsor(s) may suspend further trial treatment or procedures at a site. The study sponsor(s), FDA and DMC retain the authority to suspend additional enrollment and treatments for the entire study as applicable.

A subject may voluntarily withdraw from treatment due to what he/she perceives as an intolerable AE, or for any other reason. If voluntary withdrawal is requested, the subject should be asked to continue (at least limited) scheduled evaluations, complete a study termination form, and be given appropriate care under medical supervision until the symptoms of any AE resolve or their condition becomes stable.

8. Mechanistic Assays

Complementary studies will be performed to measure humoral immune responses at baseline and at 6 months: (a) measurement of antigen-specific IgE and IgG4 levels; and (2) SPT to peanut.

To perform these assays, blood specimens will be obtained before and 5-10 days after OFC at baseline (Visit 00) and the OFC exit (Visit 03). Further exploratory assays, including additional biomarker discovery, will be coordinated with the Immune Tolerance Network (ITN) of the NIH for protocols ARC001 and ARC002, and subject samples and clinical data will be supplied to them in conformity with HIPAA privacy restrictions and other relevant regulations.

8.1 Peanut-Specific Antibody

Antigen immunotherapy has been shown to induce antigen-specific humoral responses. The balance of isotypic response may play a role in allergen sensitivity (e.g., an increase of IgG/IgE).

At each of the mechanistic time points, a sample of plasma will be stored for assessment of peanut specific antibody levels.

We will measure total IgE and specific IgE and IgG4 by UniCAP™. Peanut specific IgE and IgG4 blood draws will be measured at baseline and the 6 months visit.

9. Statistical Considerations

This protocol is a randomized evaluation of peanut OIT versus placebo therapy and baseline for individuals with peanut allergy.

9.1 Study Endpoint Assessment

9.1.1 Primary Endpoint

The primary clinical efficacy end-point is the proportion of subjects who achieve desensitization at 6-9 months as determined for active therapy subjects by tolerating at least 250 mg of peanut protein (measured as 500 mg of peanut flour) as a single additional dose with no more than mild symptoms or for placebo subjects as tolerating, without dose limiting symptoms, at least 500 mg of flour (250 mg of peanut protein) at exit OFC. Those on active treatment that fail to achieve the target maintenance dose of 300 mg of peanut protein will be considered non-responders. An intent-to-treat analysis will be performed. All individuals failing to achieve the success definition described above will be considered failures. All individuals who drop out of the study or discontinue OIT will be considered failures, unless they have added ad libitum peanut consumption to their diet otherwise. Analysis will be via chi-square test at the 0.05 significance level.

9.1.2 Secondary Endpoints

The secondary endpoints are defined above.

9.2 Subject and Demographic Data

9.2.1 Baseline Characteristics and Demographics

Summary descriptive statistics for baseline and demographic characteristics will be provided for all enrolled subjects. Demographic data will include age, race, sex, body weight and height; these data will be presented in the following manner:

Continuous data (i.e., age, body weight and height) will be summarized descriptively by mean, standard deviation, median and range.

Categorical data (i.e., sex and race) will be presented as enumerations and percentages.

Statistical presentation for baseline and demographic characteristics may be further summarized by treatment group and baseline peanut-specific serum IgE.

9.2.2 Study Completion

The percent of subjects who complete the study, losses to follow-up, times to lost to follow-up and reasons for discontinuation (e.g., adverse events) will be presented. Statistical presentation of study completion will be further presented via analysis of the secondary endpoints summarized.

9.3 Sample Size and Power Calculations

While natural history of peanut allergy desensitization is not fully understood, short term improvements in consumption amounts that are at least double the baseline amount of 125 mg of peanut protein are believed to be uncommon. Here we assume a true placebo response rate of 25% or less. Prior assessments of the ability to consume a peanut challenge dose equivalent to the daily therapeutic dose have not been performed. We anticipate that most individuals who are successfully consuming the top therapeutic dose will be able to tolerate the challenge (i.e. a second daily dose). We will treat those individuals that fail to achieve the daily dose target as non-responders. A study size of 50 individuals randomly assigned at a 1:1 ratio of active:placebo has been selected for the study. With a 2-tailed 5% level test, we will have 76% power to detect a difference between 25% vs. 60% and 93% power if the true therapy arm response rate is 70%.

9.4 Mechanistic Studies

The mechanistic studies performed as part of the study explore: temporal changes in immune parameters and their association with peanut OIT.

The study sample size has been selected to examine the clinical endpoints of the primary and secondary objectives. The mechanistic assessments will be exploratory. Specific planned analysis strategies for the mechanistic objectives are discussed along with each objective in above.

Appendix 1. Schedule of Events

| Procedure | Visit 00 Screening | Visit 00A Baseline | Blood draw (5-10 days post-OFC) | Visit 01 Initial Escalation Days 1-3[1] | Study Product Build-up[2] | Visit 02 3 month (12 weeks) | Visit 03 6-8 months (active patients passing challenge) | Blood draw (5-10 days post OFC placebos) |
|---|---|---|---|---|---|---|---|---|
| Medical/Allergy History | X | | | | | X | X | |
| Spirometry | | X | | | | | | |
| Physical Exam | X | | | | | | | |
| Peak Flow Rate[3] | X | X | | | | | X | |
| Pregnancy Test[4] | X | X | | | | X | X | |
| Diet History | X | | | X | | X | X | |
| Targeted History/Physical Exam | | X | | X | X | X | X | |
| Blood draw for those ≥30 kg | | X | X | | | | | X |
| Peanut specific IgE, IgG4 | X | | | | | | X | |
| SPT | X | | | | | | X | |
| Clinical Research Center Peanut OIT Administration[5] | | | | X | X | X | | |
| Daily Home administration[6] | | | | X | X | X | X | |
| Oral food challenge-1 gm peanut protein (all subjects) | | X | | | | | | |
| Oral food challenge-1 gm peanut protein (placebo subjects) | | | | | | | X | |
| Passing challenge of 25 mg protein (500 mg of flour) administered as a single dose, 3-8 hours after the usual daily maintenance dose | | | | | | | X | |

[1] Peanut OIT subjects will have initial escalation to at least 1.5 mg on Day 1, return Day 2, return Day 3 if symptoms, return for dose escalation every 2 weeks.
[2] Peanut OIT subjects will have escalation visits every 2 weeks, unless epinephrine is administered as described above. Phone calls will occur 1 week after each escalation visit to assess dosing compliance and symptoms.
[3] Only prior to any OFC, at baseline, a peak flow rate may be performed if spirometry results cannot be obtained.
[4] For females of childbearing age.
[5] In Clinical Research Center or monitored clinic setting.
[6] Daily home dosing for peanut OIT with characterized peanut allergen Appendix 2. Evaluation of Asthma The evaluation of asthma severity will be assessed using the NHLBI classification published Aug. 18, 2007 as [40] described in the table below.

| Classification | Symptoms | Nighttime awakenings | Lung Function | Interference with normal activity | Short acting beta-agonist use |
|---|---|---|---|---|---|
| Intermittent (Step 1) | ≤2 days per week | ≤2x/month | Normal $FEV_1$ between exacerbations $FEV_1 > 80\%$ predicted $FEV_1/FVC$ normal* | None | ≤2 days/week |
| Mild Persistent (Step 2) | >2 days per week but not daily | 3-4x/month | $FEV_1 \geq 80\%$ predicted $FEV_1/FVC$ normal* | Minor limitation | >2 days/week but not >1x/day |
| Moderate Persistent (Step 3 or 4) | Daily | >1x/week but not nightly | $FEV_1 \geq 60\%$ but <80% predicted $FEV_1/FVC$ reduced 5%* | Some limitation | Daily |
| Severe Persistent (Step 5 or 6) | Throughout the day | Often 7x/week | $FEV_1 < 60\%$ predicted $FEV_1/FVC$ reduced >5%* | Extremely limited | Several times per day |

*Normal FEV1/FVC: 8-19 yr = 85%; 20-39 yrs = 80

Appendix 3. Anaphylaxis Staging System

| Staging System of Severity of Anaphylaxis | |
|---|---|
| Stage | Defined By |
| 1. Mild (skin & subcutaneous tissues, GI, &/or mild respiratory) | Flushing, urticaria, periorbital or facial angioedema; mild dyspnea, wheeze or upper respiratory symptoms; mild abdominal pain and/or emesis |
| 2. Moderate (mild symptoms + features suggesting moderate respiratory, cardiovascular or GI symptoms) | Marked dysphagia, hoarseness and/or stridor; shortness of breath, wheezing & retractions; crampy abdominal pain, recurrent vomiting and/or diarrhea; and/or mild dizziness |
| 3. Severe (hypoxia, hypotension, or neurological compromise) | Cyanosis or $SpO_2$ ≤92% at any stage, hypotension, confusion, collapse, loss of consciousness; or incontinence |

Criteria for Diagnosis

Anaphylaxis is likely when any one of the three following sets of criteria are fulfilled:

1. Acute onset of an illness (minutes to hours) with involvement of:

Skin/mucosal tissue (e.g., generalized hives, itch or flush, swollen lips/tongue/uvula); AND Airway compromise (e.g., dyspnea, stridor, wheeze/bronchospasm, hypoxia, reduced PEF); AND/OR Reduced BP or associated symptoms (e.g., hypotonia, syncope, incontinence).

2. Two or more of the following that occur rapidly after exposure to the allergen (minutes to hours):

Skin/mucosal tissue (e.g., generalized hives, itch/flush, swollen lips/tongue/uvula);

Airway compromise (e.g., dyspnea, stridor wheeze/bronchospasm, hypoxia, reduced PEF);

Reduced BP or associated symptoms (e.g., hypotonia, syncope, incontinence);

Persistent GI symptoms (e.g., nausea, vomiting, crampy abdominal pain).

3. Reduced BP after exposure to the allergen (minutes to hours):

Infants and Children: low systolic BP (age-specific) or >30% drop in systolic BP*;

Adults: systolic BP<90 mm Hg or >30% drop from their baseline.

* Low systolic BP for children is defined as <70 mmHg from 1 month to 1 year; less than (70 mmHg+[2×age]) from 1-10 years; and <90 mmHg from age 11-17 years.

** Isolated skin or mucosal lesions following the ingestion of a food constitute a "food-induced allergic reaction".

Appendix 4. Allergic Reaction Toxicity Grading

Current NCI-CTCAE v. 4.03 grading system for allergic reactions defined as a disorder characterized by an adverse local or general response from exposure to an allergen.

| Grade 1 - Mild | Grade 2 - Moderate | Grade 3 - Severe | Grade 4 - Life-threatening | Grade 5 - Death |
|---|---|---|---|---|
| Transient flushing or rash, drug fever <38 degrees C. (<100.4 degrees F.); intervention not indicated | Intervention or infusion interruption indicated; responds promptly to symptomatic treatment (e.g., antihistamines, NSAIDS, narcotics); prophylactic medications indicated for <=24 hrs | Prolonged (e.g., not rapidly responsive to symptomatic medication and/or brief interruption of infusion); recurrence of symptoms following initial improvement; hospitalization indicated for clinical sequelae (e.g., renal impairment, pulmonary infiltrates) | Life-threatening consequences; urgent intervention indicated | Death |

Current NCI-CTCAE v. 4.03 grading system for anaphylaxis reactions defined as a disorder characterized by an acute inflammatory reaction resulting from the release of histamine and histamine-like substances from mast cells, causing a hypersensitivity immune response. Clinically, it presents with breathing difficulty, dizziness, hypotension, cyanosis and loss of consciousness and may lead to death.

| Grade 1 - Mild | Grade 2 - Moderate | Grade 3 - Severe | Grade 4 - Life-threatening | Grade 5 - Death |
|---|---|---|---|---|
| — | — | Symptomatic bronchospasm, with or without urticaria; parenteral intervention indicated; allergy-related edema/angioedema; hypotension | Life-threatening consequences; urgent intervention indicated | Death |

These tables will be replaced with the CoFAR specific grading system for allergic reactions as displayed below.

| Grade 1 - Mild | Grade 2 - Moderate | Grade 3 - Severe | Grade 4 - Life threatening | Grade 5 - Death |
|---|---|---|---|---|
| Transient or mild discomforts (<48 hours), no or minimal medical intervention/therapy required. These symptoms may include pruritus, swelling or rash, abdominal discomfort or other transient symptoms. | Symptoms that produce mild to moderate limitation in activity some assistance may be needed; no or minimal intervention/therapy is required. Hospitalization is possible. These symptoms may include persistent hives, wheezing without dyspnea, abdominal discomfort/ increased vomiting or other symptoms | Marked limitation in activity, some assistance usually required; medical intervention/therapy required, hospitalization is possible Symptoms may include Bronchospasm with dyspnea, severe abdominal pain, throat tightness with hoarseness, transient hypotension among others. parenteral medication(s) are usually indicated. | Extreme limitation in activity, significant assistance required; significant medical/therapy. Intervention is required; hospitalization is probable. Symptoms may include persistent hypotension and/or hypoxia with resultant decreased level of consciousness associated with collapse and/or incontinence or other life threatening symptoms. | Death |

Example 2: Oral Desensitization to Peanut in Peanut-Allergic Children and Adults Using Characterized Peanut Allergen (CPNA) Peanut Oral Immunotherapy (OIT) Safety Follow-Up Study [ARC 002]

| | |
|---|---|
| Title | Oral Desensitization to Peanut in Peanut-Allergic Children and Adults using Characterized Peanut Allergen (CPNA) Peanut Oral Immunotherapy (OIT) Safety Follow-Up Study |
| Short Title | CPNA Peanut OIT: Follow-Up |
| Clinical Phase | 2 |
| Study Design | This is a multi-center, open-label follow-up study to gather additional safety information by continuing the 25 active therapy subjects from ARC001 for an additional 6 months of therapy with the ability to escalate to 2 gm of peanut protein and to cross over the 25 former placebo subjects to active treatment using the same dosing regimen used in ARC001 |
| Accrual Objective | Up to 50 peanut allergic subjects who completed ARC001 and consent to enroll in ARC002 will be enrolled |
| Primary Endpoint | The primary end-point is the safety of peanut OIT as measured by the incidence of serious adverse treatment related events |
| Secondary Endpoints | The secondary outcome measures are as follows:<br>    The primary efficacy end point is desensitization of the former placebo subjects from ARC001 to peanut flour challenge at 6-9 months. Changes in peanut-specific IgE and IgG4, changes in PST mean wheal diameters will also be assessed.<br>    Other safety measures including dosing symptom and adverse experiences while escalating to higher doses in the initial active treatment group from ARC001. |
| Study Product and Dose | Characterized Peanut Allergen. Doses characterized and normalized for total protein and ratios of specific peanut allergens will ascend per the protocol given below. Study product will be provided in break-apart capsules containing 0.5, 1.0, 10, 100 or 475 mg of peanut protein. |
| Inclusion Criteria |     Completion of study ARC001<br>    Written informed consent from subject and/or parent/guardian<br>    Written assent from all subjects as appropriate<br>    For females of child-bearing age, appropriate birth control |
| Exclusion Criteria |     Early termination from ARC001<br>    Pregnancy or lactation<br>    For Characterized Peanut Allergen Group<br>        More than 3 days from last dose in study ARC001<br>    For Placebo Group<br>        More than 2 weeks from completion of ARC001 |
| Treatment Description | Subjects will receive daily oral dosing of peanut OIT. Therapy details are found in Sections 3 and 6 of the protocol. The active treatment subjects from ARC001 will continue on peanut OIT therapy and will dose escalate as tolerated to a maximum dose of 2 gms of peanut protein. Subjects will be advised of available continuing treatment options after the completion of this study. |

| | -continued |
|---|---|
| Study Procedures | All escalation doses occur in a Clinical Research Center or monitored clinic setting.<br>After an additional 6 months of therapy, a 5 gm peanut protein OFC is performed to test for desensitization for the former active patients from ARC001, while a single challenge of 250 mg peanut protein will be performed for the former placebo patients from ARC001 (provided they have reached at least the 300 mg dosing level for at least two weeks).<br>The following procedures will be performed according to the schedules in Appendix 1:<br>    Medical and allergy history (including dietary history)<br>    Physical examination<br>    Peak flow rates<br>    Pregnancy tests<br>    Plasma analysis for IgE and IgG4 to peanut (UniCAP ™)<br>    Oral food challenge to peanut (active ARC001 patients)<br>    Peanut flour challenge (placebo ARC001 patients)<br>    Blood draws pre-OFC and 5-10 days afterward<br>    Prick skin test<br>    Study product administration<br>    Initial day escalation Oral Immune Therapy (OIT) (former placebo)<br>    Build up and maintenance OIT |

Schedule of Events

| Procedure | Visit 00A Baseline (former placebos) | Visit 01 Initial Escalation Days 1-3[1] (former placebos) | Study Product Build-up[2] (all patients) | Visit 02 3 month (12 weeks) | Visit 03 6 month (24 weeks) | Blood draw (5-10 days after OFC) |
|---|---|---|---|---|---|---|
| Medical/Allergy History | | | | X | X | |
| Peak Flow Rate[3] | X | | | | X | |
| Pregnancy Test[4] | X | | | X | X | |
| Diet History | X | X | | X | X | |
| Targeted History/Physical Exam | X | X | X | X | X | |
| Peanut specific IgE, IgG4 | | | | | X | |
| PST-food | | | | | X | |
| Clinical Research Center Peanut OIT Administration[5] | | X | X | X | | |
| Daily Home administration[6] | | X | X | X | X | |
| Blood draw | | | | | X | X |
| Oral food challenge - 5 gm peanut protein (10 gm peanut flour) (ARC001 actives) | | | | | X | |
| 250 mg protein (500 mg of flour) administered as a single dose in addition to the daily dose (repeated at 7 mo.s and potentially at 8 and/or 9 mo.s for those having moderate or worse reactions, until 80% of former placebo patients tolerate challenge) | | | | | X | |

[1]Former placebo subjects will have initial escalation to at least 1.5 mg on Day 1, return Day 2, return Day 3 if symptoms, return for dose escalation every 2 weeks.
[2]Subjects will have escalation visits every 2 weeks, unless epinephrine is administered as described in Section 6.4.1. Phone calls will occur 1 week after each escalation visit to assess dosing compliance and symptoms.
[3]Prior to any OFC, and at baseline,
[4]For females of childbearing age.
[5]In Clinical Research Center or monitored clinic setting.
[6]Daily home dosing for CPNA OIT.

1. Rationale

This current study will build on ARC001 and add additional and longer term safety information regarding the treatment of peanut allergy individuals with peanut OIT for an additional 6 months of therapy, and at higher doses Characterized Peanut Allergen.

1.1 Rationale for Selection of Study Population

Up to 50 subjects who participated in ARC001 will be enrolled into this study. The goal of this study is to collect further information on subjects who have already participated in ARC001.

In ARC001, the minimum age of 4 years was selected due to the fact that this age group would significantly benefit from desensitization during their school years and subjects at this age and older would be unlikely to "outgrow" their peanut allergy spontaneously, as well as being sufficiently developmentally advanced to comply with study procedures, given parental involvement. The upper age limit of 26 years was selected to limit the frequency of potential harmful medical conditions in subjects exposed to the risk of anaphylaxis and to have a population for study that is most reflective of the potential future utility of such a treatment. Subjects who were enrolled in ARC001 and turned 27 years of age by the time of initiation of this protocol will also be offered enrollment into this study 1.2 Rationale for Selection of Study Drug Regimen The rationale for dosing builds upon the work of the Consortium of Food Allergy Research (CoFAR) and its investigators. The dosing consists of a single-day initial escalation at very low doses, followed by a build-up phase of dose escalation, with a single escalation occurring every 2 weeks. This has been demonstrated to be well tolerated and efficacious in previous studies and was used in the registration trial.

1.3 Known and Potential Risks and Benefits to Human Participants 1.3.1 Risks

Peanut is a commonly-consumed food and as such has a well understood safety profile. Except for allergic reactions in patients with peanut allergy, it does not cause discernible side effects in humans.

In patients with peanut allergy, there have been many oral immunotherapy studies performed using procedures and dosing similar to those proposed in this Phase 2 study. In general, safety profile has been very good across the studies, and based on those studies approximately 80%, 15% and <1% of the subjects are expected to have a mild, moderate or severe reaction, respectively, during some point in their dosing of the peanut immunotherapy. It is important to note that essentially all adverse events have been allergy-related, predictable, and reversible. The only major atypical adverse event has been a single reported case of reversible eosinophilic esophagitis.

Specifically, the buildup and daily maintenance doses of peanut OIT may cause allergic symptoms including sneezing, rhinorrhea, urticaria, angioedema, flushing, flares of eczema, ocular, nasal, oral and/or throat pruritus, nausea, vomiting, abdominal discomfort, cough, wheezing and/or shortness of breath in addition to severe anaphylaxis. The likelihood of a subject experiencing any allergic symptoms is expected to be lessened by initiating dosing at extremely small amounts of characterized peanut allergen and by buildup dosing under observation in a clinical setting until the maintenance dose is achieved.

Oral food challenges may induce an allergic response. Allergic reactions can be severe including life-threatening allergic reactions; however, the risk of an allergic reaction is reduced by initiating the challenge with a very small amount of the food, gradually increasing the dose, and stopping the challenge at the first sign of a reaction. If subjects have an allergic reaction during the challenges, they may need oral, intramuscular, or intravenous medications (subjects will have an IV catheter placed before the OFCs). Trained personnel, including a physician, as well as medications and equipment, will be immediately available to treat any reaction. The anticipated rate of serious life threatening anaphylactic reactions would be <0.1%.

There may be a risk that during the participation in the trial the subjects may decrease their vigilance against accidental peanut ingestion because they believe they are protected from it. This phenomenon has been reported in previous trials, and subjects in the trial will be warned that they should continue to practice normal vigilance against accidental ingestion of peanuts or peanut-containing foods.

1.3.2 Benefits

The immediate benefits for the subject include the potential decrease in the subject's reactivity to peanuts after an accidental ingestion of peanut.

2. Objectives 2.1 Primary Objective

Demonstrate the safety of an additional 6 months of treatment using Characterized Peanut Allergen in peanut-allergic children and young adults (ages 4-27).

2.2 Secondary Objective(s)

Demonstrate the efficacy of treatment using Characterized Peanut Allergen in peanut-allergic children and young adults (ages 4-26) at 6-8 months that were initially in the ARC001 placebo group and crossed over to active therapy. Evaluate the immunological effects of peanut OIT therapy.

3. Study Design

To effectively address the Primary and Secondary Objectives of this interventional study, subjects, age 4 through 27 years, either sex, any race, any ethnicity that successfully completed ARC001 will be enrolled. All subjects will have documented consent and/or assent as is appropriate. Females of childbearing age will be using appropriate birth control. These subjects will be recruited from the ARC001 clinical sites.

Subjects from ARC001 in the former placebo group will be crossed over to active treatment and doses escalated in the same manner as in ARC001.

Those subjects from the active treatment group will be maintained on active therapy, and will be escalated to a maximum dose of 2 gm of peanut protein, which will constitute their long-term maintenance dose.

Subjects will escalate OIT dose biweekly for six months, which should achieve a maintenance dose of approximately 300 mg of peanut protein in subjects in the former placebo group and 2 gm of peanut protein (4000 mg of peanut flour) in the former active treatment group.

Clinical data and blood samples will be collected at specified intervals. If a subject is removed from therapy because of failing escalation or build-up the subject will continue to be followed per protocol for safety.

The Characterized Peanut Allergen OIT treatment for the former placebo group is comprised of an initial escalation day, an initial build-up phase to last a maximum of 24 weeks, and followed by a peanut flour challenge at 26 weeks, two weeks after the most recent up-dosing. If less than 80% of patients tolerate the challenge with only mild or no symptoms, those failing challenge will be re-tested after a month of further up-dosing; those failing after a month will be re-tested after another month of up-dosing (i.e., at 8 months). Patients failing a one-peanut challenge at 9 months will be considered study failures and maintained on the maximum dose previously tolerated (i.e., no further up-dosing).

The former active treatment group will have build-up to a maximum of 2 gm of peanut protein through 24 weeks, followed by an OFC at 26 weeks (i.e., after one year including ARC001 up-dosing).

Dosing Schedule for Peanut OIT for the Former Placebo Group

Initial Day Escalation Schedule

| Dose # | Peanut dose (mg) | Cumulative Peanut dose (mg)* |
|---|---|---|
| 1 | 0.5 mg | 0.5 mg |
| 2 | 1.0 mg | 1.5 mg |
| 3 | 1.5 mg' | 3.0 mg |
| 4 | 3.0 mg | 6.0 mg |
| 5 | 6.0 mg | 12 mg |

*If no de-escalation; frequency standard every 30 min.

Subjects at the end of the first day, tolerating less than 1.5 mg single dose, will be considered an initial day escalation desensitization failure.

Subjects tolerating only 1.5 or 3 mg single dose will go home on the greatest tolerated dose to be given daily (first dose given in Clinical Research Center under observation). All escalations will occur no sooner than 2 weeks and single dose increases in the Clinical Research Center from 1.5 to 3 to 6 mg will be attempted.

All subjects will return on Day 2 and receive their maximum tolerated dose under direct observation.

Subjects with moderate symptoms observed on Day 2 will return on Day 3 for the next lower dose under observation in the Clinical Research Center or monitored clinic setting.

Doses on day 2, 3 and 4 must be at least 1.5 mg or the subject will be considered an escalation failure.

Escalation Dosing

| Dose # | Dose | Interval (weeks) | % Increase |
|---|---|---|---|
| 6 | 12 mg | 2 | |
| 7 | 20 mg | 2 | 67% |
| 8 | 40 mg | 2 | 100% |
| 9 | 80 mg | 2 | 100% |
| 10 | 120 mg | 2 | 50% |
| 11 | 160 mg | 2 | 33% |
| 12 | 200 mg | 2 | 25% |
| 13 | 240 mg | 2 | 20% |
| 14 | 300 mg | 2 | 25% |

Capsules are opened and contents sprinkled over an age-appropriate, non-allergenic food.

Those subjects from the former ARC001 placebo group who achieve a dose of 300 mg during the initial build-up period will continue maintenance therapy until at least 6 months of total treatment. Subjects who fail to reach 300 mg within the initial period will continue up-dosing as tolerated until they have maintained a dose of at least 300 mg for at least two weeks. Those unable to achieve a dose of 300 mg of peanut protein by 36 weeks will be considered an endpoint failure.

Dosing Schedule for Peanut OIT for the Former Active Group

Dosing

| Dose # | Dose | Interval (weeks) | % Increase |
|---|---|---|---|
| 15 | 400 mg | 2 | 33% |
| 16 | 475 mg | 2 | 25% |
| 17 | 575 mg | 2 | 20% |
| 18 | 775 mg | 2 | 33% |
| 19 | 950 mg | 2 | 25% |
| 20 | 1250 mg | 2 | 20% |
| 21 | 1425 mg | 2 | 25% |
| 22 | 1625 mg | 2 | 22% |
| 23 | 2000 mg | 2 | 18% |

Capsules are opened and contents sprinkled over an age-appropriate non-allergenic food.

Those subjects from the active group who achieved less than 300 mg during the initial buildup phase in ARC001 will escalate in this study using the remaining doses described above starting at their maximum achieved dose to reach a dose of 300 mg with escalations every 2 weeks and then will follow the dosing table starting at dose 15.

Follow-Up Assessment

At 6 months, those from the ARC001 placebo group will take their usual daily home maintenance dose of peanut protein on the day of their assessment, which will be at least two weeks after the last up-dosing and before any further up-dosing (which may take place, for example, the next day). Within 3-8 hours afterwards, they will be given in clinic an extra 250 mg dose of peanut protein (measured as 500 mg of peanut flour) to mimic an accidental exposure and will be observed for reactions. Those that experience mild or less symptoms will be considered a success. All others will be considered a failure. Those considered failure will be re-challenged at 7 months; those failing that challenge will be re-challenged at 8 and/or 9 months. Failure to tolerate a one-peanut challenge at 9 months will be considered a study failure, and patients will be maintained at the highest dose previously well-tolerated (i.e., no further up-dosing).

For those that were the former active therapy subjects from ARC001, a 5 gm peanut protein OFC will be performed after this additional 6 months of therapy to a higher maintenance dose in order to measure their desensitization threshold at that point in time.

Study Design Safety Considerations

All dose escalations will be supervised in the clinic. The peanut OIT will only escalate to a maximum 6 mg single dose during the initial escalation on day 1. OFC will identify individuals who can ingest peanut safely in a supervised setting. Dosing symptoms and adverse events will be captured throughout the study. All subjects will be provided with an epinephrine auto-injector and will be trained in its use. Subjects will be cautioned against consuming any peanuts or peanut-containing foods other than Characterized Peanut Allergen while on study.

Former placebo subjects will be tested against a limited amount of additional allergen to assess the degree of actual protection afforded while consuming less than portion-size maintenance doses.

While this study continues the practice in previous studies of sprinkling allergen over an age-appropriate food before consumption, the HPMC capsules in which the Characterized Peanut Allergen is provided are ingestible and pharmaceutical grade. Therefore, after the appropriate follow-on studies to compare sprinkling over food vs. direct ingestion of capsules, this approach may in future provide an easier route to compliance for continued allergen exposure in those de-sensitized subjects averse to peanut taste or smell.

3.1 Primary Efficacy Outcome Measure

The primary end-point is the safety of peanut OIT for 6 and 12 months of treatment as measured by incidence of serious treatment related adverse events.

3.2 Secondary Endpoints

The secondary outcome measures are as follows:

The secondary clinical efficacy end-point is the proportion of subjects in the former ARC001 placebo group who achieve desensitization between 6 and 9 months as determined by tolerating at least 250 mg of peanut protein (measured as 500 mg of peanut flour) as a single dose with no more than mild symptoms;

Changes in peanut-specific IgE and IgG4, changes in PST mean wheal diameters;

Other safety measures including dosing symptom and adverse experiences as former active patients are titrated up to portion-sized dosing.

4. Selection and Withdrawal of Subjects 4.1 Inclusion Criteria

Subjects who meet all of the following criteria are eligible for enrollment as study subjects: completion of study ARC001; written informed consent from subject and/or parent/guardian; written assent from all subjects as appropriate; and for females of child bearing age, appropriate birth control;

4.2 Exclusion Criteria

Subjects who meet any of these criteria are not eligible for enrollment as study subjects: Early termination from ARC001; Pregnancy or lactation; For Characterized Peanut Allergen Group (More than 3 days from last dose in study ARC001); For Placebo Group (More than 14 days from completion of ARC001); or Premature subject termination from study dosing.

4.3 Premature Subject Termination from the Study 4.3.1 Criteria

No subject initiating therapy in this trial will be replaced. Any subject may be prematurely terminated from additional allergen exposures for the following reasons: Anaphylaxis resulting in hypotension, neurological compromise or mechanical ventilation secondary to peanut OIT dosing or any peanut food challenge; Any subject deemed to have severe symptoms and receives aggressive therapy at any time should be discontinued from further therapy, including the following: Poor control or persistent activation of secondary atopic disease (e.g., AD, asthma); Started on ARBs, ACE, beta-blockers, or other prohibited meds and there are no alternative meds available per the prescribing doctor, they will be removed from further treatment; Pregnancy; Circumstances (e.g., concurrent illness, such as gastroenteritis) requiring missed peanut OIT maintenance dosing of >7 consecutive days; or Non-adherence with home peanut OIT dosing protocol (excessive missed days; i.e., >3 consecutive days missed on 3 occasions), would be a safety issue warranting discontinuation.

Any subject may be prematurely terminated from the study if: the subject elects to withdraw consent from all future study activities, including follow-up; The subject is "lost to follow-up" (i.e., no further follow-up is possible because attempts to reestablish contact with the subject have failed); The subject has biopsy documented eosinophilic esophagitis (EoE); or The subject dies. The sponsor may terminate the study at any point for any reason.

4.3.2 Follow-Up of Subjects Who Discontinue Treatment Only

Subjects who prematurely discontinue treatment with peanut OIT will remain in the study until normal termination. All willing subjects will be followed for the duration of the study to monitor safety and efficacy parameters.

5. Study Medication 5.1 Formulation, Packaging and Labeling

The study product is characterized peanut allergen as peanut flour, formulated with a bulking agent and a flow agent in graduated doses, supplied in capsules containing 0.5 mg, 1 mg, 10 mg, 100 mg and 475 mg each of peanut protein with specified ratios of specific peanut allergens. The capsule or capsules will be opened and the entire contents mixed with food prior to ingestion by the subject.

5.2 Preparation, Administration and Dosage

The drug product will be provided pre-packaged from the site pharmacy in appropriate doses to deliver the specified dose as outlined above. The capsules constituting the dose will be opened, the contents delivered with a slight rolling motion, and tapped lightly to ensure full delivery of their contents. The powder may be added to apple juice, applesauce, yogurt, pudding or other age-appropriate food. The food must not be heated before consumption, and must be one to which the subject is not separately allergic. The product must be consumed promptly after mixing. If there is a delay of more than 24 hours in consumption, the product should be discarded and a new product dose mixed and consumed. Every attempt will be made to administer the dose of study drug at the same time of the day, each day. A target interval of at least 12 hours should pass between doses.

5.3 Modification of Study Treatment

As described in the protocol, peanut OIT doses may be adjusted by the study physician if the subject is unable to tolerate the scheduled dose increase.

5.4 Concomitant Medications

All subjects may continue their usual medications, including those taken for asthma, allergic rhinitis and atopic dermatitis, during the study. However, they must be able to discontinue antihistamines prior to the initial day of escalation, skin testing and oral food challenges. Usual topical steroids use is permitted at the time of skin testing.

5.5 Rescue Medications

Treatment of individual allergic reactions during peanut OIT therapy should be with either an antihistamine and/or epinephrine, along with IV fluids, albuterol and steroids as indicated. Subjects and parents are likely to have EpiPens®, but for those who do not, EpiPens® or an equivalent device will be provided. Subjects and parents will be trained in proper use and will be able to demonstrate proper technique with the EpiPens®.

5.6 Prohibited Medications

Prohibited medications include Omalizumab (Xolair); Systemic (oral) corticosteroids of longer than 3 weeks total duration throughout the study. If taking systemic corticosteroids, updosing should not be attempted until the subject has discontinued administration for at least 3 days; beta-blockers (oral); Angiotensin-converting enzyme (ACE) inhibitors; Angiotensin-receptor blockers (ARB); and Calcium channel blockers.

6. Study Procedures 6.1 Enrollment

Subjects will be eligible for this study once they complete ARC001. The baseline visit may be conducted in 1 or more than 1 day.

6.2 Baseline Visit

Subjects who meet eligibility criteria will return for a baseline visit (Visit 00A). This visit will include the following procedures and may take place over several days: (of note a prick skin test and IgE and IgG4 will have just been completed at the termination of ARC001 and will suffice as the baseline for ARC002, so will not need to be repeated.). Baseline assessment will include: consent and assent; targeted history and physical examination; pregnancy test, if applicable; and Peak Flow Rate (PFR).

6.3 Study Treatment Visits 6.3.1 Peanut OIT Treatment Overview for the ARC001 Former Placebo Group:

Peanut OIT administration will include an initial escalation day (Visit 01) with peanut oral immunotherapy dosing beginning at 0.5 mg with graduated doses up to 6 mg (if tolerated) occurring in the Clinical Research Center or appropriate monitored clinic setting.

Subjects who at the end of the initial escalation day tolerate less than 1.5 mg single dose will be considered an initial day escalation desensitization failure. Subjects will return on day 2 for an observed dose and will continue dosing based on the symptoms experienced as described in later in this section. This initial dosing will be followed by peanut OIT escalation every 2 weeks in the Clinical Research Center or monitored clinic setting.

With each escalation, phone contact will occur after the first week on home dosing to assess symptoms and compliance. A targeted history and physical exam will be performed at each visit. Subjects will be assessed for exacerbation of atopic dermatitis or asthma (as determined by active wheezing) prior to each in clinic dosing.

In addition to dosing visits, subjects will return to the Clinical Research Center at 3 months (Visit 02) for follow-up and at 6 months (Visit 03) for their assessment. A medical and diet history, and physical exam will also be performed at these visits.

At 6 months, a 5 gm (cumulative) peanut protein OFC will be performed on patients from the active arm of ARC001. A history, diet history and physical exam will be performed. In addition, a blood draw for IgE and IgG4 to peanut as well as mechanistic studies will be obtained prior to the peanut OFC, and then again 5-10 days afterwards, in children weighing ≥30 kg. A prick skin test will also be performed.

Peanut OIT

Initial Dose Escalation—the initial day will be done at the Clinical Research Center (or equivalent monitored clinic setting) and consist of peanut OIT dosing, beginning at 0.5 mg with graduated doses every 30 minutes up to 6 mg (if tolerated). Subjects who have active wheezing or a current flare of atopic dermatitis will be excluded. If symptoms occur preventing escalation to 6 mg, the highest tolerated dose (at least 1.5 mg) will be accepted as the "desensitization" dose for further escalation (See FIG. 1).

The maximum tolerated dose on day 1 (e.g., 1.5, 3 mg, or 6 mg) will be given on day 2 as a single dose under observation at the Clinical Research Center. If moderate symptoms occur on day 2, the subject will return to the Clinical Research Center on day 3 for the next lower dose (must be at least 1.5 mg) under direct observation. If moderate symptoms re-occur, consultation with the Medical Monitor is warranted to determine the next course of action.

If symptoms prevent initial escalation desensitization dosing to 3 mg, the subject will be dropped from active treatment due to desensitization failure and followed longitudinally.

Subjects tolerating 1.5 mg, 3 mg, or 6 mg will go home to remain on that dose daily and then will return every 2 weeks to the Clinical Research Center for single dose escalation. Subjects will be called 1 week after each dose escalation visit to assess for dosing compliance and dose reactions.

Subjects should withhold their daily home dose on the escalation day but should take all other scheduled medications. Note that the daily home dose should be taken as part of a meal. It is recommended that the dose be taken at a consistent time (within a 4-hour time period), and it is critical to take the dose every day. Doses should be separated by at least 12 hours.

Subjects who require dosing reduction during the 2-week period will reset their 2-week escalation schedule to maintain the new dose for a 2-week period prior to attempting to escalate again.

Any dose escalation attempts may be postponed for 1-2 extra weeks based on clinical judgment. An escalation attempt must be made by 4 weeks, unless escalation is delayed due to administration of epinephrine as defined herein.

Failure to successfully escalate for three consecutive attempts will result in the subject being withdrawn from further therapy. The subject will be followed for the remainder of the study for safety and immunologic monitoring. (See schedule for initial day dose escalation, FIG. 1)

A physician will be available at all times during any of the Clinical Research Center peanut OIT dosing visits.

Subjects may have clear liquids and JELL-O during the day of the initial day escalation protocol while they are being given the desensitization doses.

Reactions to Peanut OIT During Initial Escalation

Process algorithm for symptoms during the initial escalation protocol. (See FIG. 1). Subjects may develop symptoms during the initial escalation protocol, similar to those seen during other desensitization protocols (e.g., venom immunotherapy, drug desensitization). The investigator's judgment will be required to determine the best course of action with possible actions being the following: Extension of time interval between dosing (additional 30 minutes); Return to previously tolerated dose (i.e., repeat of last tolerated dose) then advance forward; or Discontinuation of desensitization protocol.

For oral/pharyngeal pruritus—the action should be to continue the normal dosing in 30 minutes.

For mild symptoms, defined as:

Skin—limited or localized hives/swelling, skin flushing or pruritus;

Respiratory—rhinorrhea/sneezing, nasal congestion, occasional cough, throat discomfort; or GI—mild abdominal discomfort/minor episode of vomiting.

Depending on the physician's discretion, the action should be either: repeat the last dose in 30-60 min or advance in 30-60 minutes.

If moderate symptoms occur, defined as:

Skin—systemic hives/swelling;

Respiratory—throat tightness without hoarseness, persistent cough, wheezing without dyspnea; or GI—persistent moderate abdominal pain/cramping/nausea, increased vomiting.

The action should be to implement a 30-60 minute observation period and then proceed with a reduced dose [decrease by 1-2 dosing steps] only if prior symptoms resolve. If symptoms continue or worsen, the subject can be treated with antihistamines (see below). If symptoms resolve, the same or reduced dose should be repeated, and then the dosing should be continued. If symptoms require additional treatment, then consultation with the Medical Monitor as listed on the cover page of the protocol is warranted to determine the next course of action. The Medical Monitor will be available for questions and decision making for any questions related to the study protocol at all times.

If more severe symptoms occur, defined as:

Respiratory—laryngeal edema, throat tightness with hoarseness, wheezing with dyspnea;

GI—significant severe abdominal pain/cramping/repetitive vomiting;

Neurological—change in mental status; or

Circulatory—hypotension.

The action should be: discontinue the initial day escalation and administer the appropriate rescue medications.

If the subject requires treatment for symptoms during the initial escalation protocol with antihistamines on one occasion, then the rest of the initial escalation may be followed. If the subject requires more than one medication (e.g., albuterol, diphenhydramine, epinephrine, or others) or multiple doses of antihistamines, the initial escalation should be terminated and the subject would not receive further OIT.

For a completed initial escalation with no symptoms or only mild symptoms, subjects should have a 2-hour post-protocol observation period. For moderate to severe symptoms, the observation period should be at least 4 hours, and up to 24 hours, based on symptoms and treatment regimen needed to stabilize.

Day 2 after Initial Dose Escalation

All subjects will return for the next dose to the clinic after the initial day escalation. This dose will be the previous day's dose or the last tolerated dose from the initial day escalation. The maximum dose is 6 mg. The minimum dose for the second day is 1.5 mg.

Those subjects administered: 6 mg: if tolerated, return home on that dose for 2 weeks until the next escalation; or if not tolerated, return for day 3 dosing with a 1 or 2 step reduction.

Those subjects administered: 1.5-3 mg: if tolerated, return home on that dose for 2 weeks until next escalation; or if not tolerated, return the next day with a 1 or 2 step reduction (if at 1.5 mg and require a dose reduction, that subject will be considered an escalation failure and followed as a longitudinal control).

Day 3 after Initial Dose Escalation

Those subjects with moderate symptoms on day 2 will return on day 3 for an observed dose. The maximum dose would be 6 mg, the minimum dose 1.5 mg.

Those subjects administered: 1.5-6 mg: if tolerated, return home on that dose for 2 weeks until next escalation; or if not tolerated, call the Medical Monitor for further management Build-Up Phase Pre 6 Month Assessment Subjects will begin the Clinical Research Center dosing scheme as outlined until 300 mg of peanut is reached. Subjects will return for a supervised dose escalation in the clinic every 2 weeks. Subjects will be called 1 week after each dose escalation visit to assess for dosing compliance and dose reactions. Any dose escalation attempts may be postponed for 1-2 extra weeks based on clinical judgment. An escalation attempt must be made by 4 weeks.

Subjects should withhold their daily home dose on the escalation day but should take all other prescribed medications. Note that the daily home dose should be taken as part of a meal. It is recommended that the dose be taken at a consistent time (within a 4-hour time period), and it is critical to take the dose every day. Doses should be separated by at least 12 hours.

Subjects who require dosing reduction during the 2-week period will reset their 2-week escalation schedule to maintain the new dose for a 2-week period prior to attempting to escalate again.

Should significant systemic symptoms, which may include mild symptoms based on physician discretion or moderate or greater symptoms, be reported during the daily home dosing, the symptom/dosing algorithm will be followed (See FIG. 2) to determine the best course of action. The appropriate treatment will depend on the type and number of symptoms. If significant symptoms occur consistently following three attempts to increase the daily oral dose in the Clinical Research Center or clinic with each attempt spaced 2-4 weeks apart, dosing escalation will be halted at the last tolerated dose, the subject continued on that dose as their maintenance dose and at the scheduled 5 gm peanut protein OFC performed at week 6 months.

Subjects will be allowed to take their other daily medications during the build-up and maintenance phases of the study (i.e., antihistamines, albuterol).

Process algorithm for symptoms during build-up phase for Peanut OIT (pre 6 month assessment). (See FIG. 2)

Subjects must be free from active wheezing or a flare of atopic dermatitis prior to any dose escalation. If not, subjects will be maintained on their current dose of study product until their flare of asthma or atopic dermatitis resolve.

Subjects will be cautioned against activities likely to increase reactivity (e.g., exercising or taking hot showers or baths within 4 hours after dosing).

At the physician's discretion, temporary reduction to half of prior dose levels can be recommended while subjects are suffering from symptoms of an upper respiratory infection or influenza, or during menses.

Subjects may develop symptoms during dosing for the build-up phase. The investigator's judgment will be required to determine the best course of action with possible actions being the following: continue with daily home dosing; continue the same daily dose for the rest of the 2-week interval, with 50% of the dose split between doses given 8-12 hours apart; return for repeat dosing in Clinical Research Center; return for dosing of previously tolerated dose (without escalation) in Clinical Research Center; or discontinuation of dosing.

If a subject has a dose escalation in the Clinical Research Center without symptoms, the action should be to continue per protocol with daily home dosing of the tolerated dose with the next escalation visit to the Clinical Research Center 2 weeks later.

If the subject only experiences oral/pharyngeal pruritus during the administration of the daily dose, then the same dose can be repeated the next day at home and continued throughout the interval unless other symptoms begin to develop (see below).

For mild symptoms, defined as:

Skin—limited or localized hives/swelling, skin flushing or pruritus;

Respiratory—rhinorrhea/sneezing, nasal congestion, occasional cough, throat discomfort; or GI—mild abdominal discomfort/minor episode of vomiting.

The action should be either to repeat the dose the next day (day 2) at home or to have the subject return to the Clinical Research Center the next day (day 2) for a repeat of the previous day's dose or the last tolerated dose (at the physician's discretion). If the dose is tolerated, then the subject will continue on that dose and return at the normal interval. If the dose causes mild symptoms again, then the subject may return to the Clinical Research Center (day 3) and be given the last tolerated dose or a 1-2 step dose reduction. If tolerated, the subject will continue on this dose for the normal time interval. If mild symptoms recur, a 1-2 step reduction should be administered the next day (day 4). If tolerated then that dose should be continued for 2 weeks. If not tolerated, consultation with the Medical Monitor should be indicated.

If moderate symptoms occur, defined as:

Skin—systemic hives/swelling;

Respiratory—throat tightness without hoarseness, persistent cough, wheezing without dyspnea; or GI—persistent moderate abdominal pain/cramping/nausea, increased vomiting.

The action should be to have the subject return to the Clinical Research Center the next day (day 2) for dosing with the previous days dose or the last tolerated dose under observation. If the dose is tolerated, the subject will continue on that daily home dose for the normal time interval per protocol. If the subject does not tolerate this dose, the subject should receive the last tolerated dose or a 1-2 step dose reduction (day 3) in the Clinical Research Center or at home if the planned dose was previously tolerated. If this dose is tolerated, it will be continued as the daily home dose for the normal time interval, then escalation attempted in the Clinical Research Center as noted below. If this dose is not tolerated, then the next dose will be a 1-2-step reduction in dosing, and the dose will be given on the Clinical Research Center (day 4). If this next dose is not tolerated, then a discussion with the Medical Monitor will ensue to make a decision about whether to continue the subject on active treatment in the study.

If more severe symptoms occur, defined as:

Respiratory—laryngeal edema, throat tightness with hoarseness, wheezing with dyspnea; or GI—significant severe abdominal pain/cramping/repetitive vomiting.

The action should be to treat the subject, and at the physicians discretion either 1) have them return to the Clinical Research Center the next day (day 2) for dosing with a 2-step reduction in dose under observation or 2) discontinue them from the active treatment. If the subject tolerates the dose reduction, then they will remain on that dose for 2 weeks and then return to the Clinical Research Center for the dose escalation. A discussion with the Study Chair or Co-Chair may ensue to make a decision about whether to continue the subject on active treatment in the study.

If a subject fails dose escalation after three consecutive (with 2-4 weeks between) attempts, he/she will be considered a dose escalation failure and the last tolerated dose will be accepted as the maintenance dose. For a completed dose escalation with no symptoms, subjects should be observed for 30 minutes. For mild symptoms, subjects should have a 1-2 hours post-protocol observation period. For moderate to severe symptoms, the observation period should be at least 4 hours and up to 24 hours based on symptoms and treatment regimen needed to stabilize the subject.

Any subject deemed to have severe symptoms including hypoxia, hypotension or change in mental status (stage 3 defined in Appendix 3) and receives aggressive therapy at any time should be discontinued from active therapy.

For specific questions related to dosing escalation or continuation of the same dose that are not answered in the above protocol, the medical monitor will be available for questions and decision-making.

Any subject who discontinues build-up dosing due to repeated allergic reactions to the peanut product will have his/her mechanistic blood drawn within approximately 1 week of discontinuation of therapy.

6.3.2 Peanut OIT Treatment Overview for ARC001 Active Treatment Group:

Treatment for this group will consist of continued dose escalations up to a maximum of 2 gm of peanut protein. This will occur every two weeks using the same build-up process as described above. The dosing table for this build up is found in section 3 of this protocol. Subjects will continue dosing until 2 gm of peanut protein is reached or until 24 weeks of dosing. They will maintain their highest tolerated dose for 2 weeks prior to the 26 week OFC. At 6 months, a 5 gm (cumulative) peanut protein OFC will be performed while on therapy. A history, diet history and physical exam will be performed. In addition, a blood draw for IgE and IgG4 to peanut, as well as mechanistic studies, will be obtained prior to the peanut OFC and 5-10 days afterwards. A prick skin test will also be performed. At the completion of that OFC, the study will be completed and treatment options will be provided by the study investigator.

6.3.3 Treatment for Reactions During the Build-Up and Maintenance Phases

Treatment of individual reactions should be with either an antihistamine and/or epinephrine, along with IV fluids, albuterol, and steroids as indicated. Generally, for mild and moderate symptoms, the subject should receive antihistamines, and for more severe symptoms, the subjects should receive epinephrine, antihistamines, and then the other medications as indicated. If severe anaphylaxis (stage 3 defined in Appendix 3) occurs at any time, dose escalation will stop and the dose will be reduced to the last tolerated dose and the subject continued on that dose as long-term maintenance without further escalation.

Antihistamines

If a subject receives antihistamines only, the dose escalation can be continued. If symptoms during a build up day require antihistamines in multiple doses or in combination with other medications (except epinephrine), there should be a dose reduction by 1-2 doses with the next dose given in the CRC. If dose escalation fails or requires treatment after two more escalation attempts each spaced 2 to 4 weeks apart, the dose should be reduced to the last tolerated dose and continued long term without further escalation.

Epinephrine

Any reaction (in clinic or at home) that requires two or more doses of epinephrine will halt further dose escalation for this individual. Maintenance on the last tolerated dose would be continued.

Clinic

If a single administration of epinephrine is required during in clinic escalation, the dose should be reduced by two doses, and the subject continued on that dose for four weeks. After 4 weeks at the reduced dose, an escalation attempt may be tried in clinic.

If a single administration of epinephrine is required a second consecutive time during this escalation attempt, the dose should be reduced by two doses, and the subject continues on that dose for 6-8 weeks. After 6-8 weeks at the reduced dose, an escalation attempt may be tried in clinic.

If a single administration of epinephrine is required a third consecutive time during this escalation attempt, the dose should be reduced by two doses and the subject continued on that dose as long-term maintenance without further escalation.

Home

If a single administration of epinephrine use occurs during dosing at home, this epinephrine use is not counted as one of the uses described above, unless severe anaphylaxis occurs at home. The subject should return to clinic for an observed dose prior to resuming any dosing at home.

Maintenance Phase (Pre 6 Month 5 gm Peanut Protein OFC Phase)

This phase consists of the subject receiving the maximum achieved daily dose of peanut OIT. The subject will continue to follow a peanut-restricted diet for the duration of the study.

For any noted symptoms during the maintenance phase, the same study dosing rules for the build-up phase will be followed.

6 Month OFC

All former ARC001 placebo subjects will receive an extra 250 mg protein (measured as 500 mg of peanut powder) dose to test for desensitization to a single peanut accidental exposure.

All former ARC001 active treatment subjects will undergo a 5 gm peanut protein OFC at 26 weeks.

Missed Peanut OIT Doses at any Phase of the Study

Missed Peanut OIT doses at any phase of the study can pose a significant risk to the enrolled subjects. The algorithm for missed consecutive doses is as follows:

1. Miss one dose—The next dose should be the current dose and could be given at home.

2. Miss two doses in a row—The next dose should be the current dose and could be given at home.

3. Miss three doses in a row—The next dose should be the current dose and should be given under observation (Clinical Research Center).

4. Miss four doses in a row—The next dose should be the current dose and should be given under observation (Clinical Research Center).

5. Miss five to seven doses in a row—For those subjects on peanut OIT, initiate the next dose as approximately 25% of the last tolerated dose. This would be done under observation (Clinical Research Center). Dose escalation would occur in the Clinical Research Center with an escalation no sooner than weekly and no longer than every 4 weeks with dose increases of 1-dose levels at each escalation. If symptoms occur, the dosing symptom rules in the build-up phase would apply.

6. Missing more than seven consecutive days of therapy constitutes an individual stopping rule and the subject would no longer take active therapy but would be followed longitudinally.

7. Additionally; excessive missed Peanut OIT doses, i.e., >3 consecutive days missed on 3 occasions, constitutes an individual stopping rule and the subject would no longer take active therapy but would be followed longitudinally.

6.4 Oral Food Challenge Double Blind Placebo Controlled

The subject will be off antihistamines for an appropriate length of time (5 half-lives of the antihistamine that is being used). Oral food challenges will be undertaken under direct medical supervision in a Clinical Research Center or food challenge area with emergency medications and staff immediately available and will follow established study procedures. Prior to the OFC, subjects will be assessed for an exacerbation of asthma as determined by active wheezing or a peak expiratory flow rate <80% of predicted. A uniform approach for food challenges will be used. Frequent assessments will be made for symptoms affecting the skin, gastrointestinal tract, and/or respiratory tract. Dose limiting symptoms, typically objective symptoms, indicate a positive reaction and termination of dosing.

6.5 Peanut OFC

All peanut OFCs conducted in the study are double blind placebo controlled food challenges. The OFC is performed by feeding gradually increasing amounts of the suspected food under physician observation. OFC is conducted as 2 challenges during a single day visit or over 2 days using placebo for one challenge and peanut for the other. If conducted in a single day, at least 2 hours must separate the first half of the challenge from the second half of the challenge. The challenge is performed so that neither the subject, nor the subject's caregiver nor the physician knows which challenge contains the peanut or the placebo.

The 6 month 10 gm peanut flour OFC (5 gm peanut protein) will be performed while the subject is on therapy and is not followed by a repeat OFC or open feeding. Although these minimum standards have been used safely in the past, the investigator may use clinical judgment to increase the intervals between doses; or repeat lower doses, if there is a concern that a reaction may be developing. The doses for the 10 gm peanut flour (5 gm peanut protein) are 1, 4, 20, 50, 75, 100, 250, 500, 1000, 1250, 1750, 2250 and 2750 mg of peanut flour. Though many published challenges begin with 5 mg of peanut flour for an initial dose, the minimum dose for this study was chosen to be 1 mg of peanut flour according to additional recent recommendations and consensus.

6.6 Prick Skin Test

Subjects will have prick skin tests performed using study approved procedures for allergens. While the subject is off antihistamines for an appropriate length of time (5 half-lives of the antihistamine that is being used), a skin test probe is pressed through a commercial extract of an allergen into the epidermis. Positive (histamine) and negative (saline-glycerin) controls are placed to establish that the response is not blocked and to determine if there is dermatographism, respectively.

6.7 Visit Windows

Dosing schedule should be adhered to strictly. Two days before, or five days after a planned dosing visit, is an acceptable window with continued daily dosing of the current dose level. Study visits for scheduled blood draws or OFC should take place within 2 weeks of the scheduled visit.

6.8 Study Blinding Procedures

Study treatment is open label. All oral food challenges are performed in a double-blind manner.

7. Safety Monitoring

This section defines the types of adverse events that should be reported and outlines the procedures for appropriately collecting, grading, recording and reporting them.

7.1 Definitions

All safety events observed under this protocol are reported through the data system for the duration of the study. Safety events related to accidental food exposure are recorded on a Food Allergy Episode form and are not reported on an adverse event form unless the event is considered a serious adverse event, as defined below. Any systemic allergic symptoms due to dosing will be recorded on a Study Product Administration form. If the event meets the definition of a serious adverse event, it will also be recorded on an adverse event (AE)/serious adverse event (SAE) form. Prick skin test and food challenge reactions that occur in the clinic are captured on study specific forms and are not reported on an adverse event form unless the event is considered a serious adverse event, as defined below. All serious adverse events are reported on the AE/SAE form set in addition to the Prick Skin form or an Oral Food Challenge form if the event occurred during one of these procedures. All other safety events that occur throughout the study are reported on the AE/SAE form set.

7.2 Food Allergy Episodes (FAE)

In order to report the occurrence of a safety event associated with accidental food ingestion, subjects will be instructed to contact the site study coordinator or investigator for any adverse event. The subject may be asked to return to the site. A Food Allergy Episode form will be completed for each of these events in addition to events where consumption of peanut without a reaction occurs. If the accidental food ingestion safety event meets the definition of a serious adverse event, as defined below, the AE/SAE form will be completed as well.

7.3 Definitions

7.3.1 Adverse Event (AE) or Medical Event

An adverse event is any untoward medical occurrence in humans, whether or not considered drug related which occurs during the conduct of a clinical trial. Any change in clinical status, ECGs, routine labs, x-rays, physical examinations, etc., that is considered clinically significant by the study investigator is considered an AE.

Suspected adverse reaction is any adverse event for which there is a reasonable possibility that the drug caused the adverse event. A reasonable possibility implies that there is evidence that the drug caused the event.

Adverse reaction is any adverse event caused by the drug.

7.3.2 Serious Events (Serious Adverse Events, Serious Suspected Adverse Reactions or Serious Adverse Reactions)

A serious adverse event including a serious suspected adverse reaction or serious adverse reaction as determined by the Investigator or the sponsor is any event that results in any of the following outcomes: death; Life-threatening AE (Life-threatening means that the study subject was, in the opinion of the investigator or sponsor, at immediate risk of death from the reaction as it occurred.); Inpatient hospitalization or prolongation of existing hospitalization; Persistent or significant incapacity or substantial disruption of the ability to conduct normal life functions; Congenital abnormality or birth defect; or Important medical event that may not result in one of the above outcomes, but may jeopardize the health of the study subject or require medical or surgical intervention to prevent one of the outcomes listed in the above definition of serious event.

7.3.3 Unexpected Adverse Event

An adverse event is "unexpected" when its nature (specificity) or severity is not consistent with applicable product information, such as safety information provided in the package insert, the investigational plan, the investigator's brochure or the protocol.

7.4 Data Monitoring Committee (DMC)

Although the safety of peanut is well established, a Data Monitoring Committee will meet every 3 months to evaluate unblinded efficacy and safety data, and will be empowered to recommend termination in the event that unexpected safety issues arise.

7.5 Toxicity Grading

The study site assigns toxicity grades to indicate the severity of adverse experiences and toxicities. The CoFAR adopted usage of NCI-CTCAE v 4.0 for application in adverse event reporting and will likewise be used for this protocol. We define allergic reactions in this protocol beyond the NCI-CTCAE system, and further characterize anaphylaxis. Anaphylaxis is characterized as mild, moderate, or severe in Appendix 3, independent of the toxicity grade associated with the event. Toxicity grading for allergic reactions including anaphylaxis is modified from the NCI-CTCAE system to be more appropriate for this study population, and is displayed in Appendix 4. We reviewed the NCI-CTCAE v 4.0 specifically for this protocol and it is otherwise appropriate for this study population. The purpose of using the NCI-CTCAE system is to provide standard language to describe toxicities and to facilitate tabulation and analysis of the data and assessment of the clinical significance of treatment-related toxicities.

The NCI-CTCAE provides a term and a grade that closely describes the adverse event. Each participating site will receive copies of the grading scales and event descriptions.

Record adverse events not included in the NCI-CTCAE listing and grade them 1 to 5 according to the General Grade Definition provided below:

| | | |
|---|---|---|
| Grade 1 | Mild | Transient or mild discomforts (<48 hours), no or minimal medical intervention/therapy required, hospitalization not necessary (non-prescription or single-use prescription therapy may be employed to relieve symptoms, e.g., aspirin for simple headache, acetaminophen for post-surgical pain). |
| Grade 2 | Moderate | Mild to moderate limitation in activity, some assistance may be needed; no or minimal intervention/therapy required, hospitalization possible. |
| Grade 3 | Severe | Marked limitation in activity, some assistance usually required; medical intervention/therapy required, hospitalization possible. |
| Grade 4 | Life-threatening | Extreme limitation in activity, significant assistance required; significant medical/therapy intervention required, hospitalization, or hospice care probable. |
| Grade 5 | Death | Death |

For additional information and a printable version of the NCI-CTCAE v. 4.03 manual, consult the NCI-CTCAE website, http://ctep.cancer.gov/reporting/ctc.html.

7.6 Adverse Events Collection Procedures

Adverse events will be evaluated from the onset of the event until the time the event is resolved or medically stable, or until 30 days after the subject completes study treatment, whichever comes first.

AEs may be discovered through any of these methods: Observing the subject; Questioning the subject, which should be done in an objective manner; Receiving an unsolicited complaint from the subject; Review of medical records/source documents; or Review of home dosing symptom logs (provided to record symptoms between visits.

Mechanistic Assays

Complementary studies will be performed to measure humoral immune responses at baseline and at 6 months: measurement of antigen-specific IgE and IgG4 levels; and PST to peanut. To perform these assays, blood specimens will be obtained at the 6 months (Visit 03). Further exploratory assays, including additional biomarker discovery, will be coordinated with the Immune Tolerance Network (ITN) of the NIH for protocols ARC001 and ARC002, and patient samples and clinical data will be supplied to them in conformity with HIPAA privacy restrictions and other relevant regulations.

Peanut-Specific Antibody

Antigen immunotherapy has been shown to induce antigen-specific humoral responses. The balance of isotypic response may play a role in allergen sensitivity (e.g., an increase of IgG/IgE).

At each of the mechanistic time points, a sample of plasma will be stored for assessment of peanut specific antibody levels.

We will measure total IgE and specific IgE and IgG4 by UniCAP™. Peanut specific IgE and IgG4 blood draws will be measured at the 6 months visit.

8. Statistical Considerations

This protocol is an observational assessment of therapy: in a cohort of placebo-crossover subjects using the same dosing regimen as in the ARC001 protocol, and in the original ARC001 active therapy cases with dose escalation 8.1 Study Endpoint Assessment The study endpoints are described above. Assessments will be descriptive with estimates of proportions and associated confidence intervals for the selected rate endpoints.

8.2 Subject and Demographic Data 8.2.1 Baseline Characteristics and Demographics Summary descriptive statistics for baseline and demographic characteristics will be provided for all enrolled subjects. Demographic data will include age, race, sex, body weight and height; these data will be presented in the following manner: continuous data (i.e., age, body weight and height) will be summarized descriptively by mean, standard deviation, median and range; and categorical data (i.e., sex and race) will be presented as enumerations and percentages.

Statistical presentation for baseline and demographic characteristics may be further summarized by treatment group and baseline peanut-specific serum IgE.

8.2.2 Use of Medications

All medications used will be coded using the World Health Organization (WHO) drug dictionary. The number and percentage of subjects receiving concomitant medications or therapies will be presented. Statistical presentation of concomitant medications or therapies may be further summarized by treatment group.

8.2.3 Study Completion

The percent of subjects who complete the study, losses to follow-up, times to lost to follow-up and reasons for discontinuation (e.g., adverse events) will be presented. Statistical presentation of study completion will be further presented via analysis of the secondary endpoints summarized.

Appendix 1 Schedule of Events

| Procedure | Visit 00A Baseline (former placebos) | Visit 01 Initial Escalation Days 1-3[1] (former placebos) | Study Product Build-up[2] (all patients) | Visit 02 3 month (12 weeks) | Visit 03 6 month (24 weeks) | Blood draw (5-10 days after OFC) |
|---|---|---|---|---|---|---|
| Medical/Allergy History | | | | X | X | |
| Peak Flow Rate[3] | X | | | | X | |
| Pregnancy Test[4] | X | | | X | X | |
| Diet History | X | X | | X | X | |
| Targeted History/Physical Exam | X | X | X | X | X | |
| Peanut specific IgE, IgG4 | | | | | X | |
| PST-food | | | | | X | |
| Clinical Research Center Peanut OIT Administration[5] | | X | X | X | | |
| Daily Home administration[6] | | X | X | X | X | |
| Blood draw | | | | | X | X |
| Oral food challenge - 5 gm peanut protein (10 gm peanut flour) (ARC001 actives) | | | | | X | |
| 250 mg protein (500 mg of flour) administered as a single dose in addition to the daily dose (repeated at 7 mo.s and potentially at 8 and 9 mo.s for those having moderate or worse reactions, until 80% of former placebo patients tolerate challenge) | | | | | X | |

[1]Former placebo subjects will have initial escalation to at least 1.5 mg on Day 1, return Day 2, return Day 3 if symptoms, return for dose escalation every 2 weeks.
[2]Subjects will have escalation visits every 2 weeks, unless epinephrine is administered as described in Section 6.4.1. Phone calls will occur 1 week after each escalation visit to assess dosing compliance and symptoms.
[3]Prior to any OFC, and at baseline,
[4]For females of childbearing age.
[5]In Clinical Research Center or monitored clinic setting.
[6]Daily home dosing for CPNA OIT.

Appendix 2. Evaluation of Asthma

The evaluation of asthma severity will be assessed using the NHLBI classification published Aug. 18, 2007 as described in the table below.

| Classification | Symptoms | Nighttime awakenings | Lung Function | Interference with normal activity | Short acting beta-agonist use |
|---|---|---|---|---|---|
| Intermittent (Step 1) | ≤2 days per week | ≤2x/month | Normal $FEV_1$ between exacerbations $FEV_1 >80\%$ predicted $FEV_1/FVC$ normal* | None | ≤2 days/week |
| Mild Persistent (Step 2) | >2 days per week but not daily | 3-4x/month | $FEV_1 \geq 80\%$ predicted $FEV_1/FVC$ normal* | Minor limitation | >2 days/week but not >1x/day |
| Moderate Persistent (Step 3 or 4) | Daily | >1x/week but not nightly | $FEV_1 \geq 60\%$ but <80% predicted $FEV_1/FVC$ reduced 5%* | Some limitation | Daily |
| Severe Persistent (Step 5 or 6) | Throughout the day | Often 7x/week | $FEV_1 <60\%$ predicted $FEV_1/FVC$ reduced >5%* | Extremely limited | Several times per day |

*Normal FEV1/FVC: 8-19 yr = 85%; 20-39 yrs = 80

Appendix 3. Anaphylaxis Staging System

| \multicolumn{2}{c}{Staging System of Severity of Anaphylaxis} | |
|---|---|
| Stage | Defined By |
| 1. Mild (skin & subcutaneous tissues, GI, &/or mild respiratory) | Flushing, urticaria, periorbital or facial angioedema; mild dyspnea, wheeze or upper respiratory symptoms; mild abdominal pain and/or emesis |
| 2. Moderate (mild symptoms + features suggesting moderate respiratory, cardiovascular or GI symptoms) | Marked dysphagia, hoarseness and/or stridor; shortness of breath, wheezing & retractions; crampy abdominal pain, recurrent vomiting and/or diarrhea; and/or mild dizziness |
| 3. Severe (hypoxia, hypotension, or neurological compromise) | Cyanosis or $SpO_2 \leq 92\%$ at any stage, hypotension, confusion, collapse, loss of consciousness; or incontinence |

Criteria for Diagnosis

Anaphylaxis is likely when any one of the three following sets of criteria are fulfilled:

1. Acute onset of an illness (minutes to hours) with involvement of:

Skin/mucosal tissue (e.g., generalized hives, itch or flush, swollen lips/tongue/uvula) AND Airway compromise (e.g., dyspnea, stridor, wheeze/bronchospasm, hypoxia, reduced PEF) AND/OR Reduced BP or associated symptoms (e.g., hypotonia, syncope, incontinence)

2. Two or more of the following that occur rapidly after exposure to the allergen (minutes to hours):

Skin/mucosal tissue (e.g., generalized hives, itch/flush, swollen lips/tongue/uvula)

Airway compromise (e.g., dyspnea, stridor wheeze/bronchospasm, hypoxia, reduced PEF)

Reduced BP or associated symptoms (e.g., hypotonia, syncope, incontinence)

Persistent GI symptoms (e.g., nausea, vomiting, crampy abdominal pain)

3. Reduced BP after exposure to the allergen (minutes to hours):

Infants and Children: low systolic BP (age-specific) or >30% drop in systolic BP*

Adults: systolic BP<90 mm Hg or >30% drop from their baseline

* Low systolic BP for children is defined as <70 mmHg from 1 month to 1 year; less than (70 mmHg+[2× age]) from 1-10 years; and <90 mmHg from age 11-17 years.

** Isolated skin or mucosal lesions following the ingestion of a food constitute a "food-induced allergic reaction".

Appendix Current NCI-CTCAE v. 4.03 grading system for allergic reactions defined as a disorder characterized by an adverse local or general response from exposure to an allergen.

| Grade 1 - Mild | Grade 2 - Moderate | Grade 3 - Severe | Grade 4 - Life-threatening | Grade 5 - Death |
|---|---|---|---|---|
| Transient flushing or rash, drug fever <38 degrees C. (<100.4 degrees F.); intervention not indicated | Intervention or infusion interruption indicated; responds promptly to symptomatic treatment (e.g., antihistamines, NSAIDS, narcotics); prophylactic medications indicated for <=24 hrs | Prolonged (e.g., not rapidly responsive to symptomatic medication and/or brief interruption of infusion); recurrence of symptoms following initial improvement; hospitalization indicated for clinicalsequelae (e.g., renal impairment, pulmonary infiltrates) | Life-threatening consequences; urgent intervention indicated | Death |

Current NCI-CTCAE v. 4.03 grading system for anaphylaxis reactions defined as a disorder characterized by an acute inflammatory reaction resulting from the release of histamine and histamine-like substances from mast cells, causing a hypersensitivity immune response. Clinically, it presents with breathing difficulty, dizziness, hypotension, cyanosis and loss of consciousness and may lead to death.

| Grade 1 - Mild | Grade 2 - Moderate | Grade 3 - Severe | Grade 4 - Life-threatening | Grade 5 - Death |
|---|---|---|---|---|
| — | — | Symptomatic bronchospasm, with or without urticaria; parenteral intervention indicated; allergy-related edema/angioedema; hypotension | Life-threatening consequences; urgent intervention indicated | Death |

4. Allergic Reaction Toxicity Grading

These tables will be replaced with the CoFAR specific grading system for allergic reactions as displayed below.

| Grade 1 - Mild | Grade 2 - Moderate | Grade 3 - Severe | Grade 4 - Life threatening | Grade 5 - Death |
|---|---|---|---|---|
| Transient or mild discomforts (<48 hours), no or minimal medical intervention/therapy required. These symptoms may include pruritus, swelling or rash, abdominal discomfort or other transient symptoms. | Symptoms that produce mild to moderate limitation in activity some assistance may be needed; no or minimal intervention/therapy is required. Hospitalization is possible. These symptoms may include persistent hives, wheezing without dyspnea, abdominal discomfort/ increased vomiting or other symptoms | Marked limitation in activity, some assistance usually required; medical intervention/therapy required, hospitalization is possible Symptoms may include Bronchospasm with dyspnea, severe abdominal pain, throat tightness with hoarseness, transient hypotension among others. parenteral medication(s) are usually indicated. | Extreme limitation in activity, significant assistance required; significant medical/therapy. Intervention is required; hospitalization is probable. Symptoms may include persistent hypotension and/or hypoxia with resultant decreased level of consciousness associated with collapse and/or incontinence or other life threatening symptoms. | Death |

Example 3: Exemplary Pharmaceutical-Grade Encapsulated Peanut Allergen and Use Thereof Peanut flour used in the present compositions contains characterized peanut protein and is formulated with hydroxyl-methylcelluose and a flow agent in graduated doses, comprising capsules containing 0.1 mg, 1 mg, 10 mg, 100 mg and 475 mg each of peanut flour.

Oral immunotherapy in a food-allergic individual is accomplished by initially exposing the subject to the food allergen at doses below those associated with a clinical reaction, and subsequently increasing the dose in a step-wise fashion over a number of months (or longer). Clinical de-sensitization refers to the loss of clinical reaction to a limited amount of allergen in cases where lack of constant exposure to the allergen will result in re-established reactivity. Clinical tolerance, on the other hand, is not associated with renewed reactivity on loss of constant exposure. De-sensitization to a moderate amount of peanut protein (e.g., about 125 mg, about 250 mg, about 300 mg, about 600 mg or about 1000 mg, or the amount of protein in 2-4 peanuts) can be accomplished by oral immunotherapy in approximately 70% of subjects within a six month time period. Clinical tolerance occurs in some subset of these subjects, but there is no existing serum or other biomarker recognized to predict the development of tolerance, and it is unknown whether increasing the dose or extending the time under treatment (or both) is effective in increasing the rate of tolerance.

Dosage and Administration

Initial Day Escalation

Subjects may be treated according to the following protocol, dispensing the contents of the capsules to the subject every 30 minutes until the schedule is completed or dose-limiting allergic symptoms (e.g., gastrointestinal pain, vomiting, diarrhea, significant urticaria, or shortness of breath) develop. Administration of the initial dosing protocol may be performed under observation with immediate access to equipment and skilled personnel able to manage symptoms of anaphylaxis. Subjects may be observed by medical personnel for at least 1 hour post dosing.

| Dose # | Amount (mg protein) | Increment | 0.1 mg capsules | 1 mg capsules |
|---|---|---|---|---|
| 1 | 0.5 | — | 1 | |
| 2 | 1.0 | 100% | | 1 |
| 3 | 1.5 | 50% | 1 | 1 |
| 4 | 3.0 | 100% | | 3 |
| 5 | 6.0 | 100% | | 6 |

Home Dosing

After the initial day, subjects are to be dosed for two weeks at home with the maximum tolerated dose reached on the initial day, once per day at the same time each day. The contents of the capsules should not be heated. Dosing should take place within 20 minutes after a full meal, and should be followed by fluid, ad libitum. Subjects should avoid physical activity, hot baths, showers or saunas for at least two (2) hours after dosing.

Build-Up Escalation

Dose escalation may be performed after two weeks of dosing. The intended schedule for further dose escalation is provided below, with the dose escalation to take place under direct observation with immediate access to equipment and skilled personnel able to manage the symptoms of anaphylaxis. Subjects should be observed by medical personnel for from about 30 minutes to about 1 hour post dosing.

Dose escalation should then followed by two weeks of daily therapy at home once per day at the same time per day with the newly increased dose.

In the case that dose escalation is not tolerated, the subject should return to the previously-tolerated dose for two weeks, and then attempt dose escalation again. If dose escalation is again not tolerated, the increased dose should be reduced by 50%, and maintenance dosing continued using a twice-daily administration schedule for each half-dose. If dose reduction is unsuccessful in accomplishing an increase in daily dose, consideration should be given to removing the subject from therapy.

| Dose # | Amount (mg protein) | Increment | 1 mg capsules | 10 mg capsules | 100 mg capsules |
|---|---|---|---|---|---|
| 7 | 6 | — | 6 | | |
| 8 | 12 | 100% | 2 | 1 | |
| 9 | 25 | 108% | 5 | 2 | |
| 10 | 50 | 100% | | 5 | |
| 11 | 75 | 50% | 5 | 7 | |
| 12 | 100 | 33% | | 1 | |
| 13 | 125 | 25% | 5 | 2 | 1 |
| 14 | 150 | 20% | | 5 | 1 |
| 15 | 200 | 33% | | | 2 |
| 16 | 250 | 25% | | 5 | 2 |
| 17 | 300 | 20% | | | 3 |

The recommended maintenance dose for adults and children (4 years or older) is at least 300 mg daily. Clinical experience on immunotherapy in children younger than 4 years and subjects over age 26 years is limited. Subjects may continue on therapy for an indefinite length of time, and may continue dose escalation at the discretion of the treating physician. Standardized peanut flour with diluent and flow agent in break-apart capsules, of 0.1 mg, 1 mg, 10 mgs, 100 mg, and 475 mg peanut protein each.

Example 4: Assay Method for the Determination of Ara h 1, 2 and 6 Proteins in Peanut Flour The objectives of these experiments were to develop a workable separation of the Ara h allergenic proteins Ara h 1, 2 and 6 in peanut flour, and to optimize sample preparation techniques. The methods were developed for support of product formulation development, and for use in quality control.

A variety of separation modes were evaluated, including strong cation exchange (SCX), size exclusion chromatography (SEC) and several different reversed phase columns and mobile phase systems.

An assay was developed for the determination of Ara h 1, 2 and 6 allergenic proteins in roasted peanut flour. A simple single stage extraction procedure was developed using Tris buffer at pH 8.2, followed by centrifugation and filtration. Samples were prepared at 100 mg/mL and extracted at 60° C. for 3 hours. The final neat filtrate was suitable for direct analysis by high performance liquid chromatography (HPLC).

The HPLC separation utilized a reversed phase separation using a wide pore 300 Å silica column with a bonded butyl stationary phase. A binary gradient was employed based upon 0.1% trifluoroacetic acid (TFA) and acetonitrile. The mobile phase was compatible with mass spectrometry. Detection was accomplished with a UV detector at 214 nm. Alternatively, although with greatly reduced sensitivity, 280 nm served as an alternate wavelength, if necessary. If 280 nm was used, injection volumes may be increased to improve detectability.

Quantitation was achieved using area percent of the total protein area of the chromatogram. Peaks eluting earlier than about 13 minutes were not included in the total area. Since well characterized Ara h reference standards are not readily available, absolute protein content was estimated using bovine serum albumin (BSA) as a proxy working standard.

BSA reference standard was prepared at 1 mg/mL in diluent, and was used to determine system suitability, in addition to calculation of the total protein found in the samples. Long term solution stability was not specifically determined, but was demonstrated to be stable for the duration of the analysis up to 24 hours.

Specificity of the method was estimated by comparison of the retention times and peak patterns as compared to standard Ara h proteins that were either commercially available, or were provided as gifts from research laboratories. The Ara h proteins were not discrete entities, but rather were complex ensembles of many similar proteins. Therefore, the Ara h 1, 2 and 6 allergens appear as clusters of peaks within a retention time region. The relative amount of a particular Ara h protein was then determined as the total area within an elution region. Chromatographic resolution of the various regions appeared to be sufficient, and the method is useful for comparison of subtle differences in these regional patterns for different lots and sources of peanut flour proteins. Mass spectrometry was compatible with the mobile phase.

Precision of five injections of BSA during system suitability ranged from 0.1% to 0.9% relative standard deviation (RSD). Method precision for triplicate independent preparations of a single lot of peanut flour ranged from 1.1% RSD for Ara h 6 to 18.3% for Ara h 1. The higher % RSD for Ara h 1 was largely due to the difficulty of integrating the Ara h 1 shoulder from a subsequent larger cluster. Comparison of the quantitative results obtained for three different peanut flour lots independently analyzed on different days with different analysts yielded Ara h values that agreed between 86% and 107%. Total protein content agreed within 95%-102%. One source of these differences was due to variable integration of the peak clusters.

The column selected is readily available from Phenomenex, and many other vendors offer similar wide pore columns. The recipient laboratory may want to adjust injection volumes as necessary to keep the highest peaks within the linear range of their detector, depending upon the detector flow cell configuration and sensitivity. Column ovens also vary considerably in their effective temperatures, although the separation was not particularly sensitive to column temperature. Finally, the precision of general accuracy of the method depends upon accurate integration of a fairly complex chromatogram, so the receiving laboratory should probably gain some experience with setting parameters for their particular chromatographic data system prior to initiating validation.

Equipment

The HPLC instruments and column used for the development are shown in Table 1.

TABLE 1

| Instrumentation and Columns | |
| --- | --- |
| HPLC System | Quaternary Pump, G1311A, SN US64401268 |
| | Autosampler, G1313A, SN DE33225034 |
| Agilent HP 1100 with | Column Oven, G1316A, SN US64401423 |
| ELS detector | Diode Array Detector, G1315B, SN DE43623474 |
| (PharmAssist ID: HPLC#4) | Agilent Chemstation, version A.09.03 |
| Columns | |
| Size Exclusion | Tosoh Bioscience G2000SWxl 4.6 × 300 mm SN: P0139-04G |
| Ion Exchange | Agilent 300-SCX 30 × 50 mm, 3 um SN: USQD002473 |
| | Imtakt Scherzo SM-C18 2 × 50 mm 3 um SN: JD13ACI |
| Reversed Phase | Phenomenex Jupiter C18 4.6 × 250 mm 5 um 300 Å SN: 348023-2 |
| | Phenomenex Jupiter C4 4.6 × 150 mm 5 um 300 Å SN: 275868 |

Reagents and Supplies

Indoor Biotechnologies. Ara h 1 product NA-AH1, lot 34080.

Indoor Biotechnologies. Ara h 2 product NA-AH2-1, lot 34034.

Indoor Biotechnologies. Ara h 6 product NA-AH6-1, lot 34073.

Alternative standards from USDA New Orleans: Ara h 1, S080410 A1, 5.4 mg/mL H2O; Ara h 2, A-Q100610, A2 in PBS, 0.62 mg/mL; Ara h 6, 0.67 mg/mL in milliQ H2O.

Peanut flour, Light Roast, Golden Peanut Company; Partially defatted peanut flour 12% fat, Product code 521271, lot #111FA36211.

Peanut flour, Light Roast, Golden Peanut Company; Partially defatted peanut flour 12% fat, Product code 521271, lot #111FA36111.

Peanut flour, Light Roast, Golden Peanut Company; Partially defatted peanut flour 12% fat, Product code 521271, lot #112FA02411.

Peanut flour, Light Roast, Golden Peanut Company; Partially defatted peanut flour 12% fat, Product code 521271, lot #112FA02411.

Bovine Serum Albumin, Sigma Aldrich product number A2153, lot 100M1900V. Potency 100%.

Sigma Aldrich Total Protein Kit, Micro Lowry, Peterson's Modification. Product code TP0300, lot # SLBB0890.

Sigma Aldrich Trizma HCl, lot #081M5450V.

Purified Water, in-house, USP Grade

Acetonitrile, EMD, HPLC Grade cat. no. AX0145-1.

TFA, HPLC grade, EMD Cat. TX1276-0004.

MicroSolv Titan 0.45 μm membrane filters, Regenerated Cellulose 25 mm, Cat. 58045-R25C Class A Volumetric Glassware—Various Sizes.

HPLC 2 mL autosampler injection vials.

Method Development

Properties and Current Methodology for Characterization of Ara h Proteins in Peanuts:

Ara h protein species differ widely in their properties. Ara h 1 comes from the vicilin seed storage protein family while Ara h 2 belongs to the congluten family. Many of these Ara proteins undergo post-translational modifications.

Ara h 1 and Ara h 2 have been the most intensively studied. Ara h 1 is the dominant species comprising 13-16% of the total protein content in peanut flour, which itself contains about 50% total protein.

Peanut flour contains about 50% protein, with the remainder consisting of various lipids and carbohydrates. Table 2 is a partial summary of the expected molecular weights of the major allergenic proteins targeted by this method development. Ara h 3 properties are included, even though this protein was not included as part of the method development.

TABLE 2

Summary Table of molecular weights and properties of some of the Ara h proteins of interest.

| Allergen Protein | Monomer MW/pI | Higher Order Structures | Comments |
|---|---|---|---|
| Ara h 1 | 64 kDa<br>pI = 4.55 | Trimer | Trimer formed by non-covalent hydrophobic association - dissociates in SDS.<br>Oligmeric aggregates can form with 600-700 kDa |
| Ara h 2 | Doublet at ~20 kDa<br>pI = 5.2 | Unknown | More resistant to hydrolysis than Ara h 1 |
| Ara h 3 | Proteolytically processed triplet at 42-45 kDa, with band at 25 kDa, plus less abundant chains at 12-18 kDa. | Unknown | Rapidly hydrolysed |
| Ara h 6 | 15 kDa<br>pI = 5.2 | Unknown | More resistant to hydrolysis than Ara h 1 |

The most widely employed current method of semi-quantitative analysis is ELISA. ELISA colorimetric kits are based on the antigenic reactions of the Ara h proteins with IgE. However, commercially available kits are not highly specific because they use polyclonal antibodies that are not allergen-specific. These kits can produce both false positives and false negatives, due to cross-reactivity with other proteins and with variations of the epitopes on the Ara h proteins. Confirmatory testing with LC-MS/MS is required. As a result, such commercially available ELISA based tests are not suitable for quantitative analytical testing.

SDS PAGE gel may be used as an analytical tool supporting research on the Ara h proteins.

Absolute confirmation of the presence of the Ara h 1 allergens may be accomplished with reduction of the disulfides with DTT, followed by tryptic digestion. The peptides are then analyzed by LC-MS/MS, where the instrument is tuned to detect only known peptide fragments. This approach is used for highly selective and sensitive detection of Ara h proteins in complex foodstuffs.

The present inventors developed new HPLC methods that may be employed for the determination of Ara h proteins in peanuts.

The primary goal of this work was to develop a simple chromatographic tool that may be used to support a range product development activities (e.g., selection of peanut flour lots, insure the consistency of protein allergen composition in CPNA lots) with the analysis of selected Ara h proteins in peanut flour, possibly mixed with various excipients.

Evaluation of Separation Modes for HPLC

Size Exclusion Chromatography

Based upon the molecular weight differences of the Ara h 1, 2 and 6 proteins (approximately 64, 20 and 15 kD respectively), size exclusion chromatography (SEC) appeared to be feasible. Based on prior experience with similar sized proteins in our laboratory, the Tosoh Bioscience silica-based G2000SW×1 columns were evaluated. These columns have a 125 Å pore size, with a nominal MW range of 5-150 kD. They are non-adsorptive and robust, and can withstand the higher pressures of HPLC as compared to their soft gel counterparts.

Figure 7:
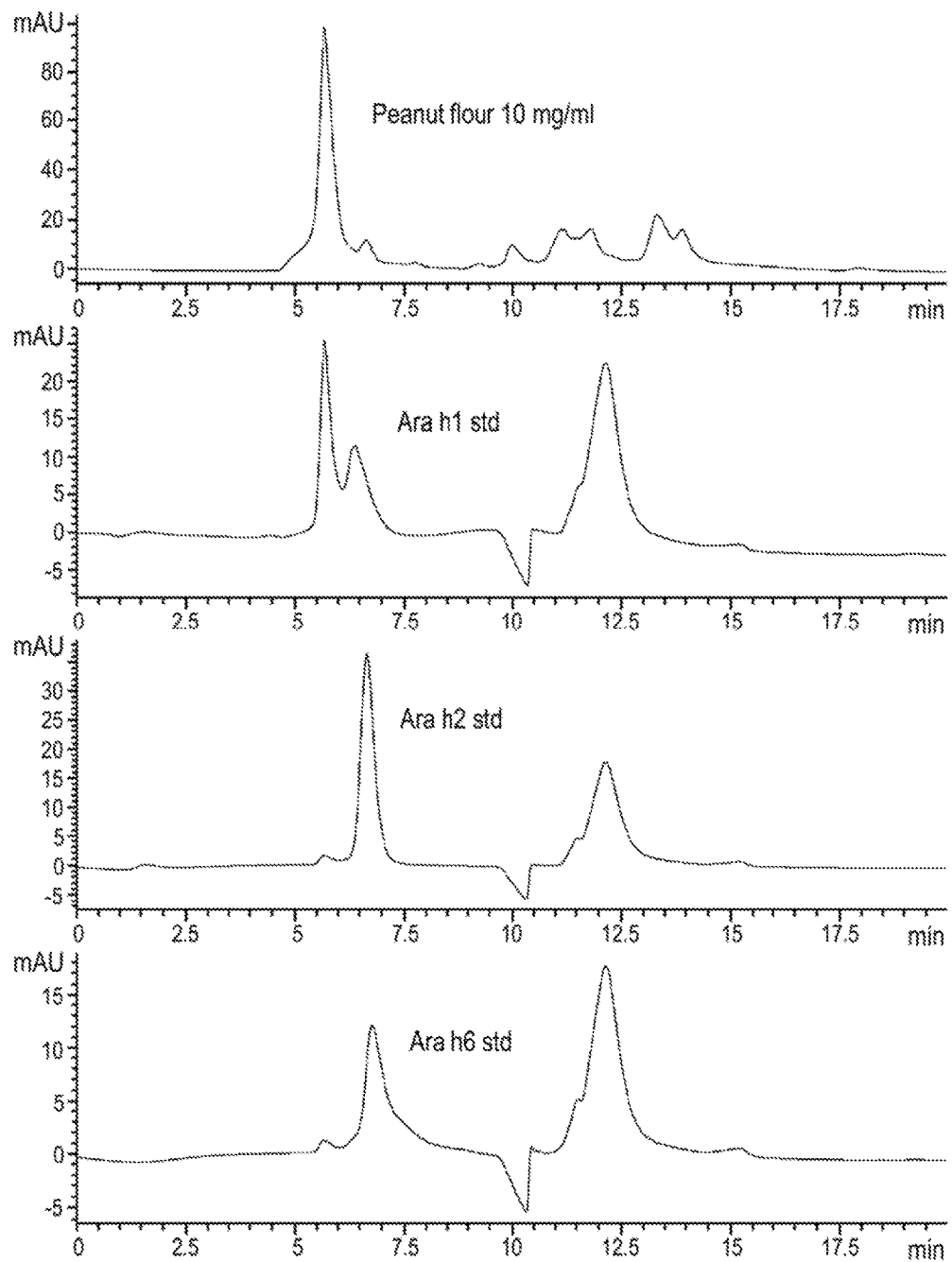
FIG. 7. SEC separation of peanut flour extract with Ara h standards; detection at 280 nm. Top panel: Peanut flour at 10 mg/mL; second panel: Ara h1 standard; third panel: Ara h2 standard; and bottom panel: Ara h6 standard.

An initial mobile phase of 0.1% TFA with 10% acetonitrile was prepared. A trial extraction of peanut flour at 10 mg/mL was performed using 0.1% TFA. FIG. 7 shows typical chromatograms obtained with this SEC column and mobile phase. Ara h standards obtained from Indoor Biotechnologies are included. The peanut flour extract shows a major group of peaks eluting at about 6 minutes, and generally matching the retention time of the Ara h 1 standard. The elution order of the standards shows their increasing retention time with decreasing molecular weight as expected. The peanut flour extract also produces a cluster of peaks from about 9-15 minutes that were assumed to be due to lower molecular weight components. Detection was at 280 nm, since the Ara h proteins are known to contain tryptophan. However, detection at 214 nm using the peptide bond was also suitable with the mobile phase chosen, and offered higher sensitivity if needed.

FIG. 7 illustrates SEC separation of peanut flour extract, with Ara h standards from Indoor Biotechnology (detection at 280 nm). The SEC mode may be useful in characterization of the peanut flour proteins. It was determined that multiple columns with excessive separation times could be used in order to further separate the target proteins and to improve specificity for distinguishing the Ara h 1, 2 and 6 proteins.

Reversed Phase

Reversed phase may be used for protein separations. Wide pore 300 Å pore sizes are generally preferred in order to allow full access of the proteins to the bonded stationary phase. Both C18 and C4 phases may be used. A mobile phase system of gradients of 0.1% TFA and acetonitrile was selected to provide compatibility with mass spectrometry if needed, as well as UV transparency.

Figure 8:
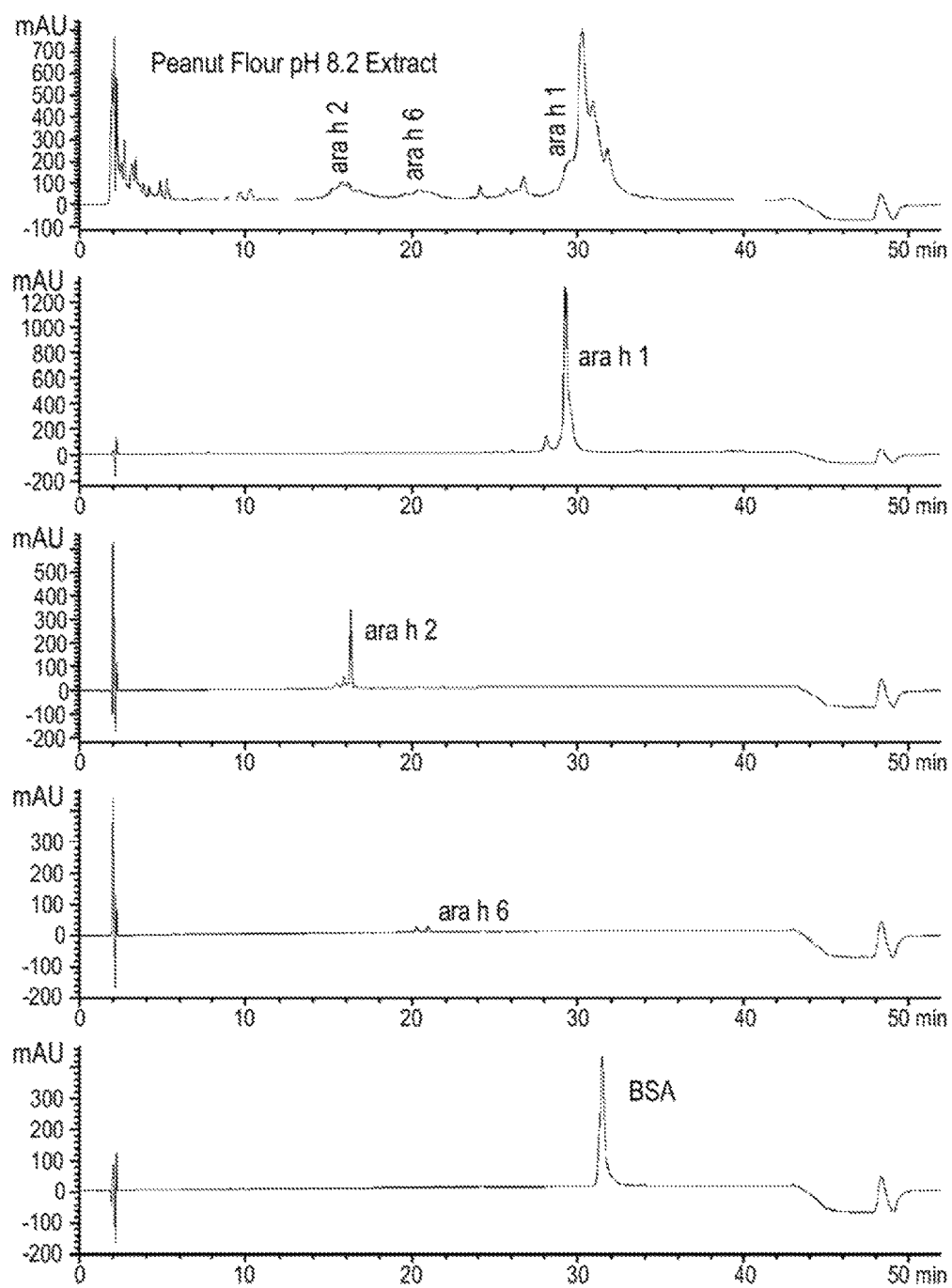
FIG. 8. Peanut flour extract at 214 nm under final Reversed Phase High Performance Liquid Chromatography (RP-HPLC) method conditions. USDA Ara h standards, along with a 1 mg/ml BSA solution are also shown. The extracts are as follows: Top panel: Peanut flour, pH 8.2 extract; second panel: Ara h1 peak; third panel: Ara h2 peak; fourth panel: Ara h6 peak; bottom panel: 1 mg/ml BSA solution.

Initial trial separations of both the peanut flour extracts and the available Ara h protein standards were successful, and confirmed the suitability of this mode as the basis for further development. The C4 and C18 phases produced similar separations. The C4 phase reduced the retention of several peaks in the early portion of the chromatogram. Detection can be at either 214 nm or 280 nm; however, 214 nm provides greater sensitivity. The gradient conditions were able to be rapidly optimized to produce a separation of the various Ara h proteins. Injection volume was set at 10 μL, but can be adjusted to achieve full scale detection of the largest peaks. Column temperature was eventually set at 50° C. to minimize column pressure while improving overall resolution. FIG. 8 presents an overlay of a typical peanut flour extract, along with reference standards provided by the USDA under the final proposed method conditions. Bovine serum albumin (BSA) at 1 mg/mL is recommended as a suitable working standard and is also shown. Table 3 summarizes the final recommended conditions for the reversed phase separation of the peanut flour extracts.

TABLE 3

Final proposed method conditions for reversed phase separation of peanut flour extract.

| | |
|---|---|
| Standard and Sample Diluent | 20 mM Tris buffer, pH 8.2 |
| Column | Phenomenex Jupiter C4, 300 Å 5 µm, 4.6 × 150 mm. Cat. No. 00F-4167-E0, or equivalent. |
| Mobile Phase | A: 0.1% TFA in water<br>B: 0.1% TFA in 90% acetonitrile |
| Flow Rate | 1.0 mL/min |
| Column Temperature | 50° C. |
| Standard Concentration | 1 mg/mL BSA |
| Injection Volume | 10 µL |
| Detection | 214 nm |

| | Time: | % B: |
|---|---|---|
| Gradient Profile | 0 min | 15% |
| | 40 min | 55% |
| | 42 min | 100% |
| | 45 min | 100% |
| | 46 min | 15% |
| Ara h Retention Times | Ara h 2 ~13-19 min | |
| | Ara h 6 ~19-23 min | |
| | Ara h 1 ~28-30 min (front shoulder on peak cluster) | |
| Total Run Time | about 52 min | |

FIG. 8 illustrates peanut flour extract at 214 nm under final proposed reversed phase method conditions. USDA Ara h standards, along with a 1 mg/mL BSA solution are also shown.

Figure 9:
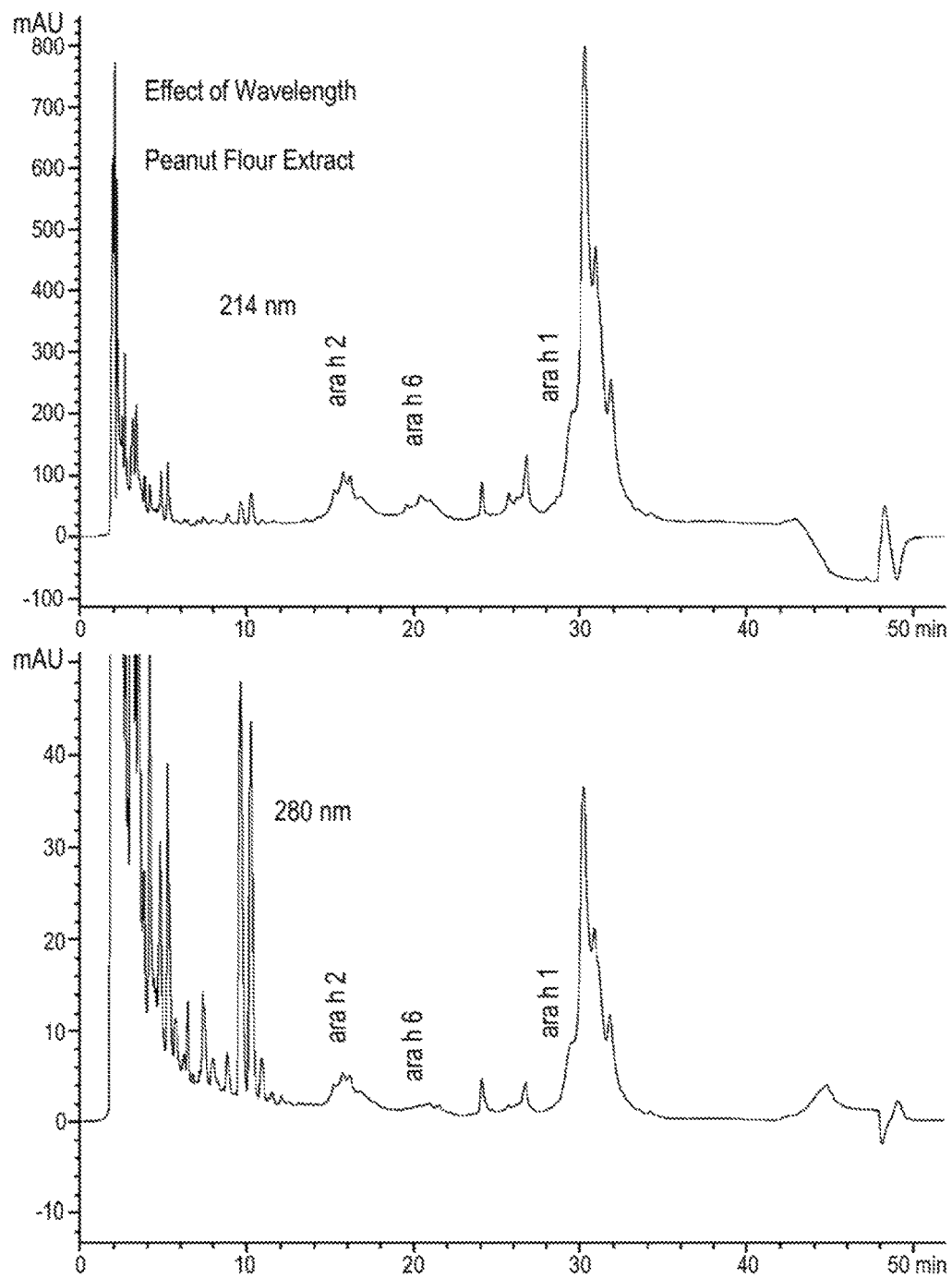
FIG. 9. Comparison of 214 nm (top panel) and 280 nm (bottom panel) for RP-HPLC separation of a typical peanut flour extract.

FIG. 9 compares a typical peanut flour extract at 214 nm and 280 nm. The Ara h proteins are still identifiable at 280 nm with the same general patterns. However, their sensitivity is much lower as noted in their peak heights on the absorbance axis. Sensitivity is reduced about 20 fold at 280 nm vs. 214 nm. Interestingly, the earlier peaks in the chromatogram prior to about 13 minutes appear to have higher relative absorbances at 280 nm.

If it is desired to perform the method at 280 nm, method injection volume could be increased, typically up to 100 µL, to help compensate for the reduced extinction coefficients, without severe losses in chromatographic efficiency and to minimize interference in the final product formulation. The injection volume of 10 µL at 214 nm may also have to be adjusted, such as to place the maximum height of the Ara h 1 peak cluster at about 32 minutes at about 1 AU, or within the linear range of the particular detector used.

The gradient profile was chosen to elute many of the smaller peaks early in the chromatogram by starting the composition at 15% acetonitrile. After about 36 minutes, no peaks were observed so the remainder of the gradient profile is essentially a column wash step, including a brief excursion to 100% B (90% acetonitrile). No late eluting peaks were observed despite long sequences of 24 hours or more; thus, the gradient was effective in keeping the column free of late eluting peaks.

In any gradient separation at low wavelengths, good solvent and instrument cleanliness was determined to be important in separating peaks. TFA is a common source of contamination peaks, thus, it should be of the highest HPLC grade and be kept refrigerated during storage. Mobile phases were stable in use for at least 48 hours with no new peaks appearing in blank runs. Note that the diluent is a buffer at pH 8.2, which is being injected into the TFA mobile phase at about pH 2. No peak shape problems were observed with this combination. If adapting the method to 280 nm with a large injection volume, good peak shapes should be confirmed.

Overall, the separation proved to be very robust, with different analysts on different days being able to reproduce retention times and peak patterns without problems. FIG. 9 is a graph illustrating the comparison of 214 nm and 280 nm for reversed phase separation of a typical peanut flour extract.

Figure 10:
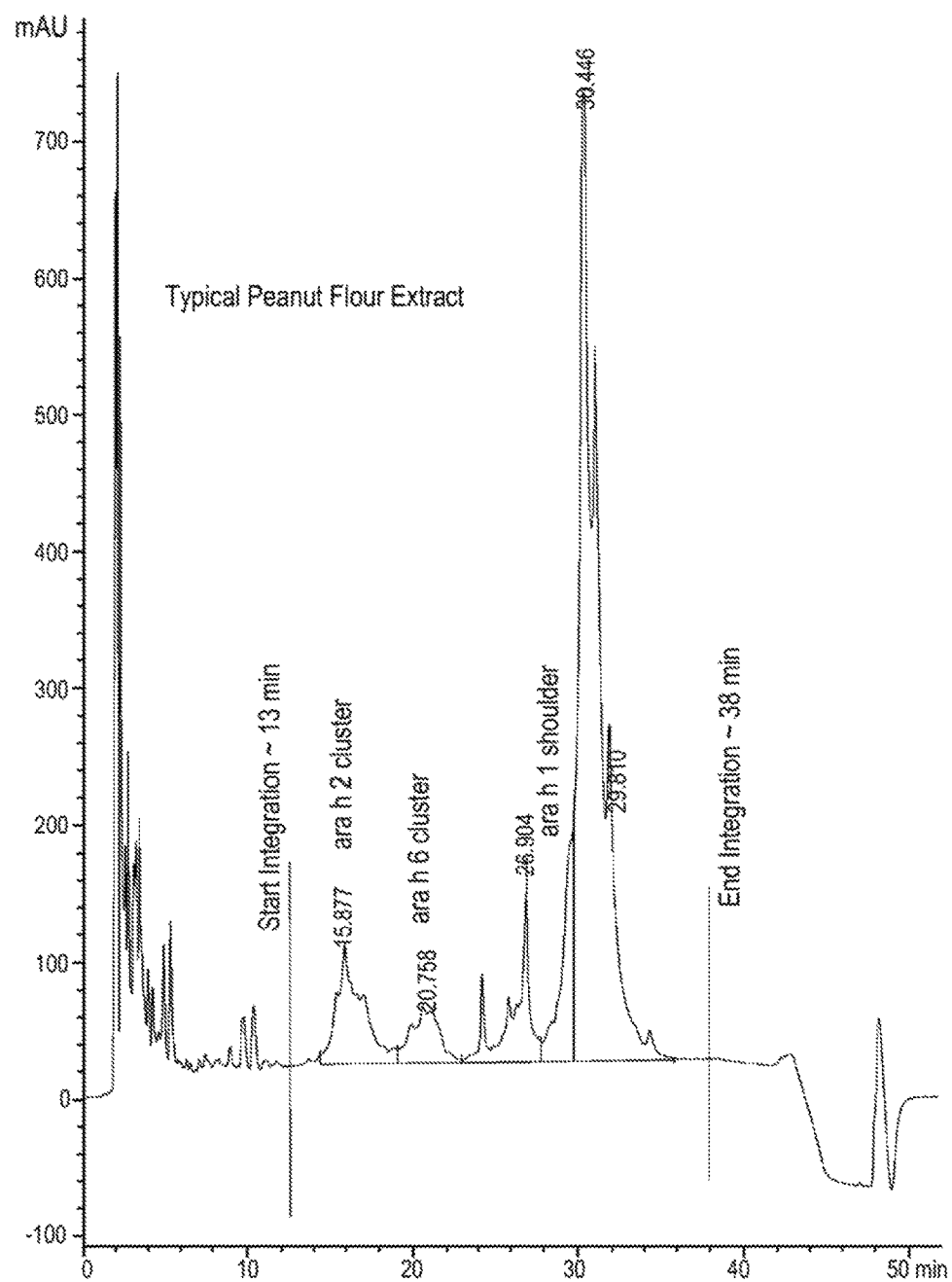
FIG. 10. Peak identification and example integration of the Ara h 2, 6 and 1 regions of the chromatogram. The total peak area from 13-38 minutes represents the total extracted protein content of the samples.

Integration of the peanut flour extracts assumes that the proteins elute after about 13 minutes, and end at about 40 minutes. The total peak area within that region is assumed to represent the total extracted protein content of the sample. Furthermore, the relative percentages of the Ara h 2, 6 and 1 proteins are taken as the sum of the area of each of the clusters as shown in FIG. 10. Exact integration points will have to be modified, depending upon the exact elution times with different columns and HPLC instruments.

FIG. 10 is a graph illustrating peak identification and example integration of the Ara h 2, 6 and 1 regions of the chromatogram. The total peak area from 13-38 minutes represents the total extracted protein content of the samples.

Sample Extraction Procedures

The initial trial extraction procedures of the peanut flour utilized 0.1% TFA at about pH 2, sonicated for 30 minutes. This simple procedure produced similar qualitative peak patterns as compared to the final recommended procedure at pH 8.2. General procedures outlined by (Heick et al., J. Chromatography A, 1218 (2011) 938-943) may be used for sophisticated LC-MS testing for peanut allergens. Briefly, the procedure is as follows: 1. Extract peanut flour at 100 mg/mL in pH 8.2 20 mM Tris HCl for 3 hrs at 60° C.; 2. Centrifuge; 3. Concentrate sample 10:1 with a 3 kD or a 5 kD centrifugal filter; and 4. Analyze interior, retain filter solution.

The interior solution, while concentrated about 10 fold, is semi-quantitative, since the retained volume is only approximate.

Figure 11:
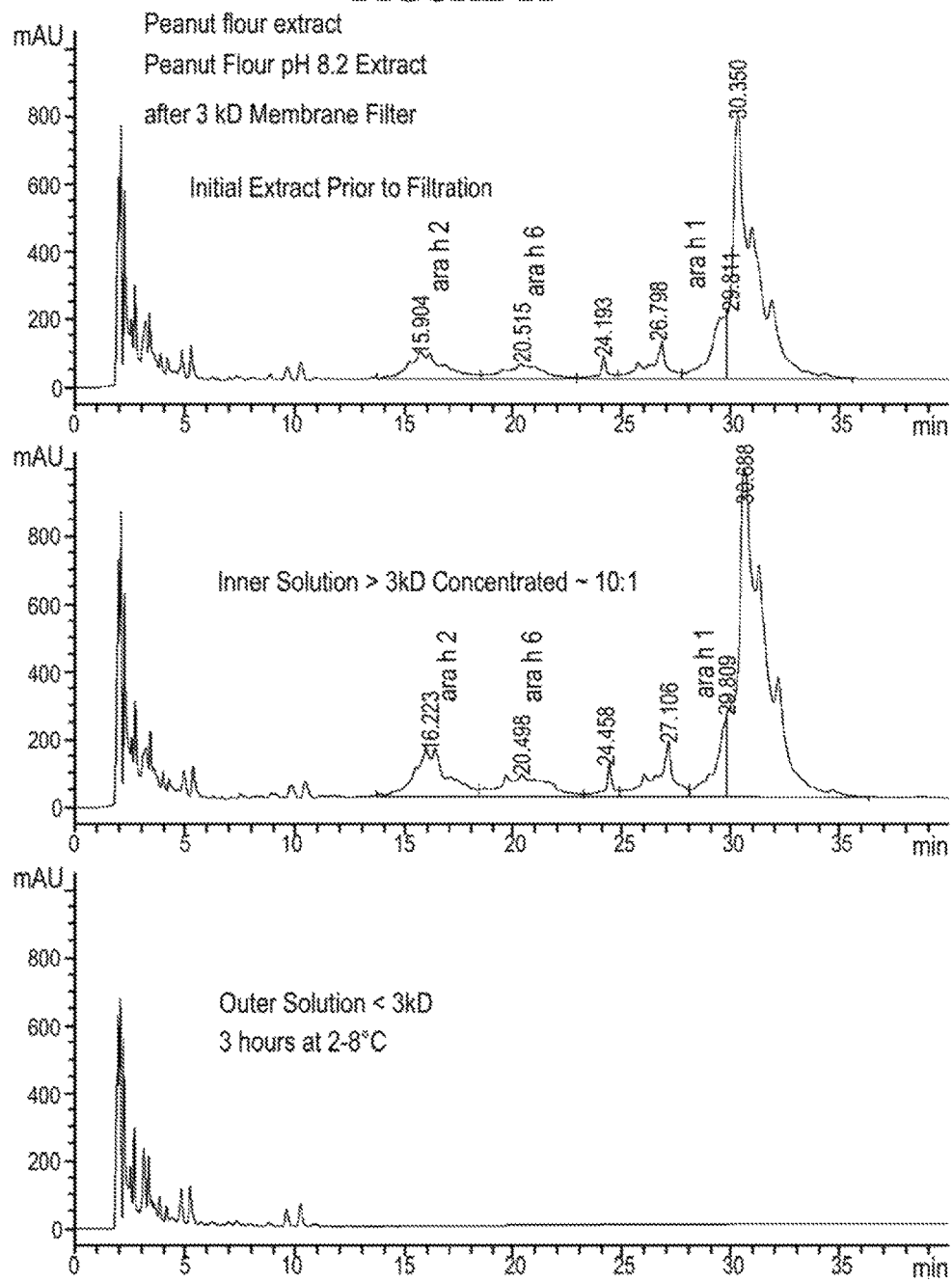
FIG. 11. Comparison of the original pH 8.2 extract (top chromatogram), and the inner solution from a 3 kD centrifugal filter (center) and outer solution (lower).

FIG. 11 shows typical chromatograms of the original PF extract of 100 mg/mL after 3 hours. When using the centrifugal ultrafilters, a sample volume is placed in the inner portion of the device. Centrifugation pushes the solution through the membrane from the inner compartment to the outer centrifuge tube. The middle and lower chromatograms show the inner and outer solutions respectively. The inner solution was reduced from about 10 mL to about 1 mL, and the increase in the maximum peak heights compared to the original solution was evident. More significantly though, the peak pattern is qualitatively quite similar to that of the unfiltered sample. Meanwhile, the outer solution contains only peaks eluting earlier than about 12 minutes, which presumably are all less than 3 kD.

After further consideration, the ultrafiltration step was eliminated. Therefore, the final recommended sample preparation procedure extracted a 100 mg/mL PF sample at 60° C. for 3 hours, then centrifuged and filtered the liquid through a conventional 25 mm 0.45 µm membrane filter of regenerated cellulose, which is non-adsorptive towards proteins. FIG. 11 is a graph illustrating the comparison of the original pH 8.2 extract (top chromatogram), the inner solution from a 3 kD centrifugal filter (center) and outer solution (lower).

Figure 12:
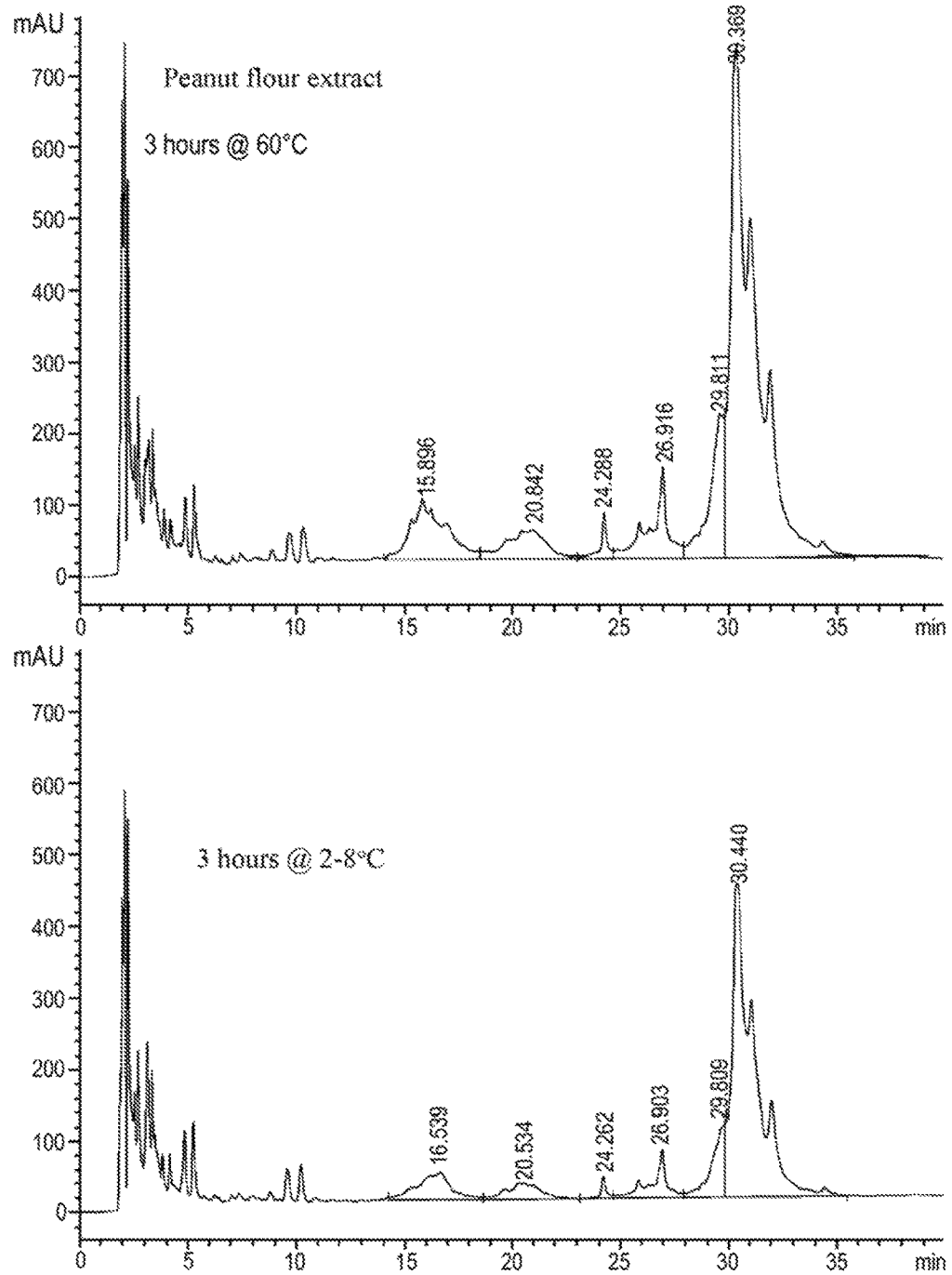
FIG. 12. Comparison of extraction of 100 mg/ml peanut flour sample at pH 8.2 under the proposed medical conditions. Upper panel is for 60° C./3 hours, lower panel is 2-8° C./3 hours.

The inventors next examined how susceptible the peanut flour (PF) proteins were towards hydrolysis at the elevated extraction temperature. A semi-quantitative experiment was designed to compare PF extracted under refrigerated conditions for 3 hours compared to the 60° C. extraction. The relative area percent values of each of the Ara h regions are compared. If extensive hydrolysis of the proteins were occurring, it seemed likely that the relative peak patterns should also shift as the proteins were destroyed. On the other hand, the total protein content might be expected to shift up or down as the extraction efficiency changed with temperature. FIG. 12 compares these results. The qualitative peak pattern is very similar under the hot and cold extraction conditions. However, based upon the chromatograms, the overall protein content is lower for the cold extraction, as may be expected. Table 4 presents the relative peak areas under both conditions.

FIG. 12 is a graph illustrating the comparison of extraction of 100 mg/mL peanut flour sample at pH 8.2 under the proposed method conditions. Upper figure is for 60° C./3 hours, lower is 2-8° C./3 hours.

TABLE 4

Comparison of the area percent of the Ara h proteins in the same lot of peanut flour extracted at 60° for 3 hours, compared to one of the same lots extracted under refrigerated conditions for 3 hours. Values represent the average of two injections.

| Sample ID: | Ara h 2 | Ara h 6 | Ara h 1 |
|---|---|---|---|
| 111FA36111 HOT | 10.37% | 5.64% | 9.69% |
| 111FA36111 Cold | 9.11% | 5.28% | 7.64% |

BSA as a Standard Protein

The overall protein extraction efficiency was difficult to measure, because if the extraction were extended to much longer times, it would be difficult to determine if some limiting value represented total extraction of the proteins or not. The inventors determined that the most effective way to estimate extraction efficiency and the true Ara h concentrations was to determine absolute protein. While relative amounts of each of the Ara h proteins could be determined using area percent values, peanut flour with higher or lower overall protein might yield higher or lower antigen content. Therefore, the absolute protein was determined using a of standard. Pure Ara h standards are not readily available in high purity. The only commercially available standards were from Indoor Biotechnologies. These standards were purchased, but were both impure, and exorbitantly expensive for any type of routine use.

Bovine Serum Albumin is widely available in high purity, and with a molecular weight of 65 kD, is similar to the Ara h 1 antigenic protein. FIG. 8 shows its elution under the proposed method conditions, at a concentration of 1 mg/mL. It also absorbs at 280 nm, and could be used as a standard at that wavelength if necessary.

The suitability of BSA as a proxy standard for the determination of protein content was evaluated by comparison to protein values obtained using the modified Lowry Method, using a kit purchased from Sigm-Aldrich (see Reagents and Supplies). The total protein contents found agreed remarkably well between the HPLC and Lowry methods, as shown in Table 5. Given this agreement, it was concluded that the 60° C./3 hour extraction procedure was quantitative, both fully extracting the protein, and not hydrolyzing it during the extraction. The validity of using BSA as a secondary standard for the determination of absolute protein levels in the sample extracts was also confirmed.

TABLE 5

Comparison of the total percent protein found in a peanut flour sample extracted according to the proposed method, as determined by the Lowry method and by the proposed RP-HPLC method using BSA as a reference standard.

| PF Lot #: | Lowry UV: | | HPLC with BSA Std | |
|---|---|---|---|---|
| 111FA36111 | 10.17% | Avg = 9.60% | 9.54% | Avg = 9.56% |
| | 9.03% | | 9.57% | |
| | | % Protein from PF CoA: 51% | | |

The peanut flour CoA for this lot is listed by the manufacturer as 51% (using N×5.46). Thus, the total protein found in the sample extract by either the Lowry or RP-HPLC method represents only about 19% of the total protein in the peanut flour (but that the amount of extracted protein is consistent among peanut flour lots). It is not known whether this low protein recovery represents only a partial extraction of the Ara h proteins, or whether the Ara h proteins are being extracted at a much higher relative efficiency, however, other proteins present in the flour are not extracted with this procedure. The Lowry method does show however, that whatever proteins are being extracted, are being counted as part of the total area in the RP-HPLC separation.

The final proposed method calculates the area percent of each of the Ara h regions as compared to the total area of the chromatogram over the 13-38 minutes time window. The total protein content is determined against the BSA standard, which establishes system suitability. The absolute concentrations of each of the Ara h proteins can then be calculated as needed by simply multiplying their area percent values times the total protein.

Method Precision

The final method precision was estimated by performing the extraction of a single sample in triplicate, and analyzing the results according to the proposed method. Integration of the samples was performed by using forced integration events on the data system (ChemStation), rather than manual integration.

The overall method precision was determined to have excellent results, as demonstrated by the 0.46% RSD value of the total protein; and the Ara h 1 areas produced a much higher RSD value of 18.29%. This is due to the difficulty of integration of the shoulder peak of Ara h 1 from the neighboring cluster (see FIG. 10). Manual integration or other data systems can be expected to improve the precision.

TABLE 6

Method Precision for triplicate extractions and determinations of a single lot of peanut flour according to the proposed method. Reported values are area percent of each Ara h species.

| | Area %: | | | |
|---|---|---|---|---|
| Lot #: | Ara h 2 | Ara h 6 | Ara h 1 (shoulder) | % found total protein |
| 112FA02411 | 12.20% | 6.36% | 7.41% | 18.64% |
| | 11.95% | 6.30% | 9.68% | 18.48% |
| | 12.30% | 6.22% | 10.72% | 18.61% |
| Avg: | 12.15% | 6.30% | 9.27% | 18.57% |
| Std Dev: | 0.1762 | 0.0718 | 1.6955 | 0.0859 |
| % RSD: | 1.45% | 1.14% | 18.29% | 0.46% |

Method Pre-Qualification

This section summarizes both this data, and miscellaneous results obtained during the final stages of the method development. Each value presented represents the average of duplicate injections.

TABLE 7

Comparison of the area percent values and total protein content of various lots of peanut flour, by two different analysts on two different days. These values represent the average of two injections.

| Peanut Flour Lot | Ara h 2 | | Ara h 6 | | Ara h 1 (shoulder) | | % Total Protein HPLC | |
|---|---|---|---|---|---|---|---|---|
| | Test 1 | Test 2 | Test 1 | Test 2 | Test 1 | Test 2 | Test 1 | Test 2 |
| 111FA36111 | 10.60% | 12.29% | 5.59% | 5.77% | 8.82% | 9.73% | 9.57% | 10.08% |
| | % Match | 86.31% | % Match | 96.76% | % Match | 90.70% | % Match | 94.94% |
| 111FA36211 | 10.65% | 12.02% | 5.48% | 5.67% | 11.14% | 9.36% | 9.93% | 10.02% |
| | % Match | 88.58% | % Match | 96.63% | % Match | 118.97% | % Match | 99.17% |
| 112FA02411 | 10.62% | 12.15% | 5.93% | 6.30% | 9.91% | 9.27% | 9.38% | 9.24% |
| | % Match | 87.40% | % Match | 94.12% | % Match | 106.92% | % Match | 101.58% |
| 112FA02411 | NA | 12.18% | NA | 6.28% | NA | 10.58% | NA | 9.92% |

Overall, the agreement between the two independent determinations ranged from about 86%-107%. Based on these data, a reasonable acceptance criteria for method accuracy would appears to be about 85%-115%.

Conclusions

The separation conditions presented in the method proved to be robust over the course of the method development. The extraction procedures are capable of producing Ara h proteins in a simple, robust and reproducible manner. Method sensitivity is accurate at 214 nm. If interferences are found from excipients during formulation development, the use of 280 nm may be feasible, but with an increased injection volume to maintain adequate sensitivity.

Proposed Method

Summary

This method is designed to assist in the characterization of Ara h 2, Ara h 6 and Ara h 1 allergenic proteins found in peanut flour. Extraction of the target proteins from the flour is accomplished using a 20 mM Tris buffer at pH 8.2. Peanut flour is suspended in the buffer at a concentration of about 100 mg/mL for 3 hours at 60° C. The sample is then centrifuged and clarified using a 0.45 µm regenerated cellulose membrane filter, and is ready for direct injection into the HPLC.

Separation is accomplished using a reversed-phase column with a C4 stationary phase, designed specifically for protein separations. The mobile phase is a gradient using 0.1% trifluoroacetic acid (TFA) and acetonitrile, and is compatible with mass spectrometry. Detection is at 214 nm. Bovine serum albumin (BSA) is used as a quantitative reference standard. The Ara h proteins are not single molecular entities, but elute as a cluster of peaks within a retention time region. Quantitation is performed by summing the total peak area of each region assigned to a given Ara h protein type. Results are presented in terms of the percentage of each Ara h type against the total proteins found. Lower molecular weight fragments are eluted early in the chromatogram, and are not included in the total protein determination.

Equipment and Materials

Binary gradient HPLC with a UV detector at 214 nm, capable of injecting 10 µL, and generating a flow rate of 1.0 ml/min, with a temperature controlled column compartment at 50° C.; Column (Phenomenex Jupiter C4, 300 Å 5 µm, 4.6×150 mm. Cat. No. 00F-4167-E0, or equivalent); Analytical balance capable of weighing 2 g±0.1 mg; pH meter and electrode; Centrifuge; and Water bath with shaking table, capable of maintaining 60° C., or equivalent; Purified Water suitable for HPLC; Acetonitrile (HPLC grade); Trifluoroacetic Acid (HPLC grade); Tris HCl buffer reagent (Sigma Trizma HCl, cat. No. T3253); regenerated Cellulose Membrane 25 mm filters, 0.45 µm (MicroSolv cat. No. 58045-R25-C); Bovine Serum Albumin (Sigma cat no A2153).

Mobile Phase Preparation

Mobile PHASE A (0.1% V/V TFA in water): for the preparation of 1 L, separately add to a suitable sized glass container 1000 mL of purified water and 1 mL of TFA. Mix thoroughly, and degas with light vacuum for about 1 minute.

Mobile Phase B (0.11% v/v TFA in 90% acetonitrile): for the preparation of 1000 mL, separately add to a suitably sized glass container 900 mL of acetonitrile, 100 mL of purified water, and 1 mL of TFA. Mix thoroughly, and degas with light vacuum for about 1 minute.

Diluent Preparation 20 mM Tris HCl Buffer: For the preparation of 1000 mL, separately add to a suitably sized glass container: 1000 mL of purified water and 3.15±0.3 g of Tris HCl reagent. Dissolve. The initial pH will be about 4.8-5.0. Adjust with 1 N NaOH to a final pH of 8.2±0.1.

Standard Solution Preparation

BSA Working Standard (1.0 mg/mL in diluent): accurately weigh a target of 50±5 mg of BSA into a 50 mL volumetric flask. Dissolve and bring to volume with diluent and mix well.

Sample Preparation

Prepare a suspension of peanut flour at 100 mg/mL as follows: weigh about 2 g±0.2 g of peanut flour; transfer to a centrifuge tube or other suitable vessel; pipet 20.0 mL of diluent; seal the vessel and suspend the peanut flour using moderate shaking; and place the sample into a bath held at 60° C. for 3 hours, with shaking for frequent agitation.

Upon completion of the extraction, centrifuge the sample about 30 minutes, or until the supernatant is relatively clear. Filter a portion of the supernatant through a 0.45 µm regenerated cellulose membrane filter, discarding the first 3 mL. Transfer sample solution to injection vials for analysis.

Analysis Procedure

Operating Conditions

The HPLC conditions are summarized in the table below.

| | |
|---|---|
| Standard and Sample Diluent | 20 mM Tris buffer, pH 8.2 |
| Column | Phenomenex Jupiter C4, 300 Å 5 µm, 4.6 × 150 mm. Cat. No. 00F-4167-E0, or equivalent. |
| Mobile Phase | A: 0.1% TFA in water |
| | B: 0.1% TFA in 90% acetonitrile |
| Flow Rate | 1.0 mL/min |
| Column Temperature | 50° C. |
| Standard Concentration | 1 mg/mL BSA |

-continued

| | | |
|---|---|---|
| Injection Volume | 10 μL | |
| Detection | 214 nm | |
| | Time: | % B: |
| Gradient Profile | 0 min | 15% |
| | 40 min | 55% |
| | 42 min | 100% |
| | 45 min | 100% |
| | 46 min | 15% |
| Ara h Retention Times | Ara h 2 ~13-19 min | |
| | Ara h 6 ~19-23 min | |
| | Ara h 1 ~28-30 min (front shoulder on peak cluster) | |
| Total Run Time | about 52 min | |

Injection Sequence

| Sample | Number of Injections Each |
|---|---|
| Diluent Blank | 1 or until clean, stable baseline |
| Working Standard | 5 |
| Samples 1-10 | 1 |
| Bracketing Standard | 1 |

Repeat the bracketing standard after every 10 samples, and always as the final injection.

System Suitability Requirements

No interfering peaks were detected in the blank injection over a time period from about 13-38 minutes. The peak pattern for the peanut flour samples generally was similar to that shown in FIG. 14. The precision of the areas of the 5 standard injections is ≤2% RSD. The area of the bracketing standard matches the average area of the initial 5 injections within 2%.

Integration Settings

Start integration at about 13 minutes, and end at about 38 minutes. The early region of the chromatogram from 0-13 minutes, and the late region after about 38 minutes, should not be included as part of the total area.

Figure 13:
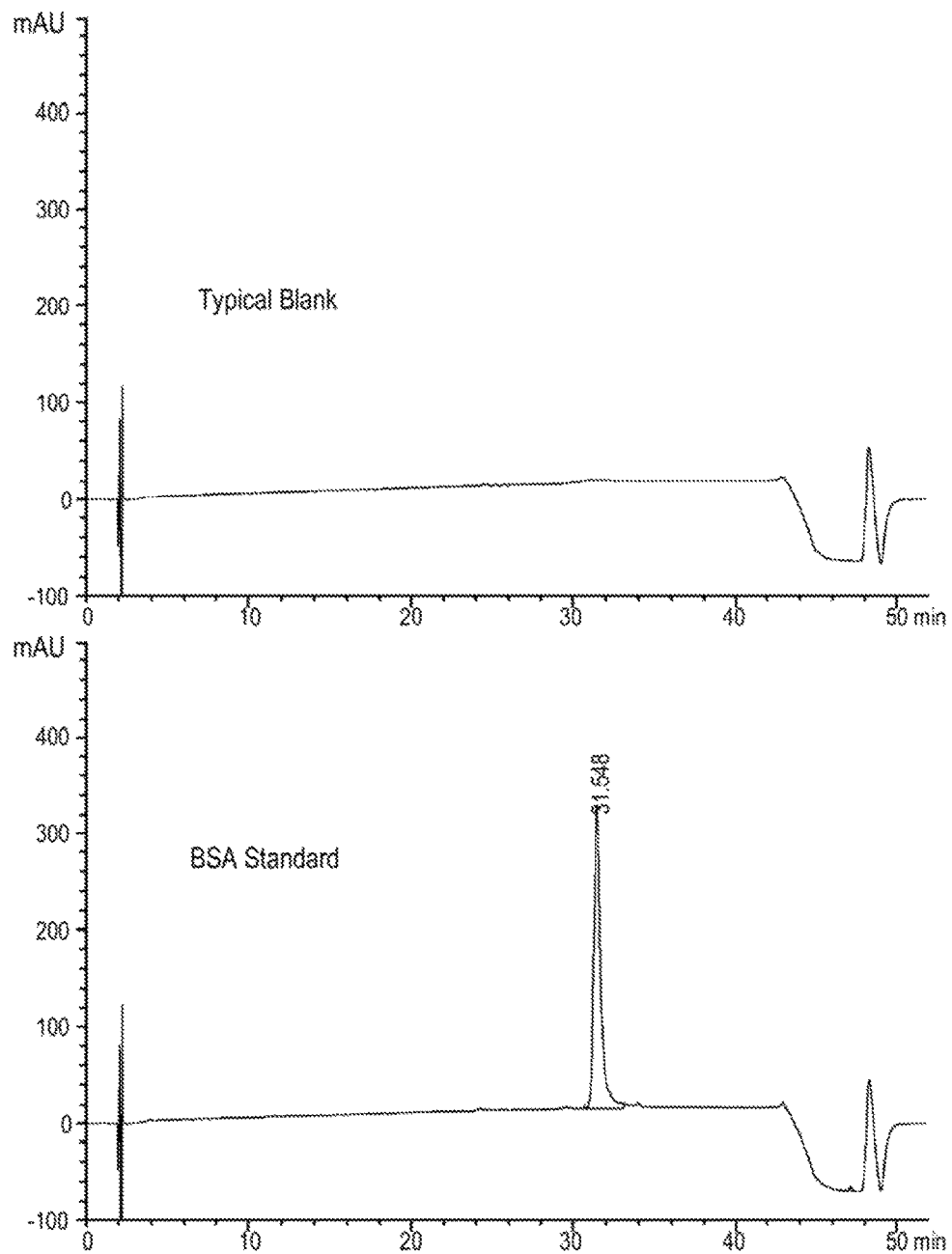
FIG. 13. Typical chromatograms of a diluent blank and the BSA working standard.

FIG. 13 is a graph illustrating typical chromatograms of a diluent blank and the BSA working standard.

Figure 14:
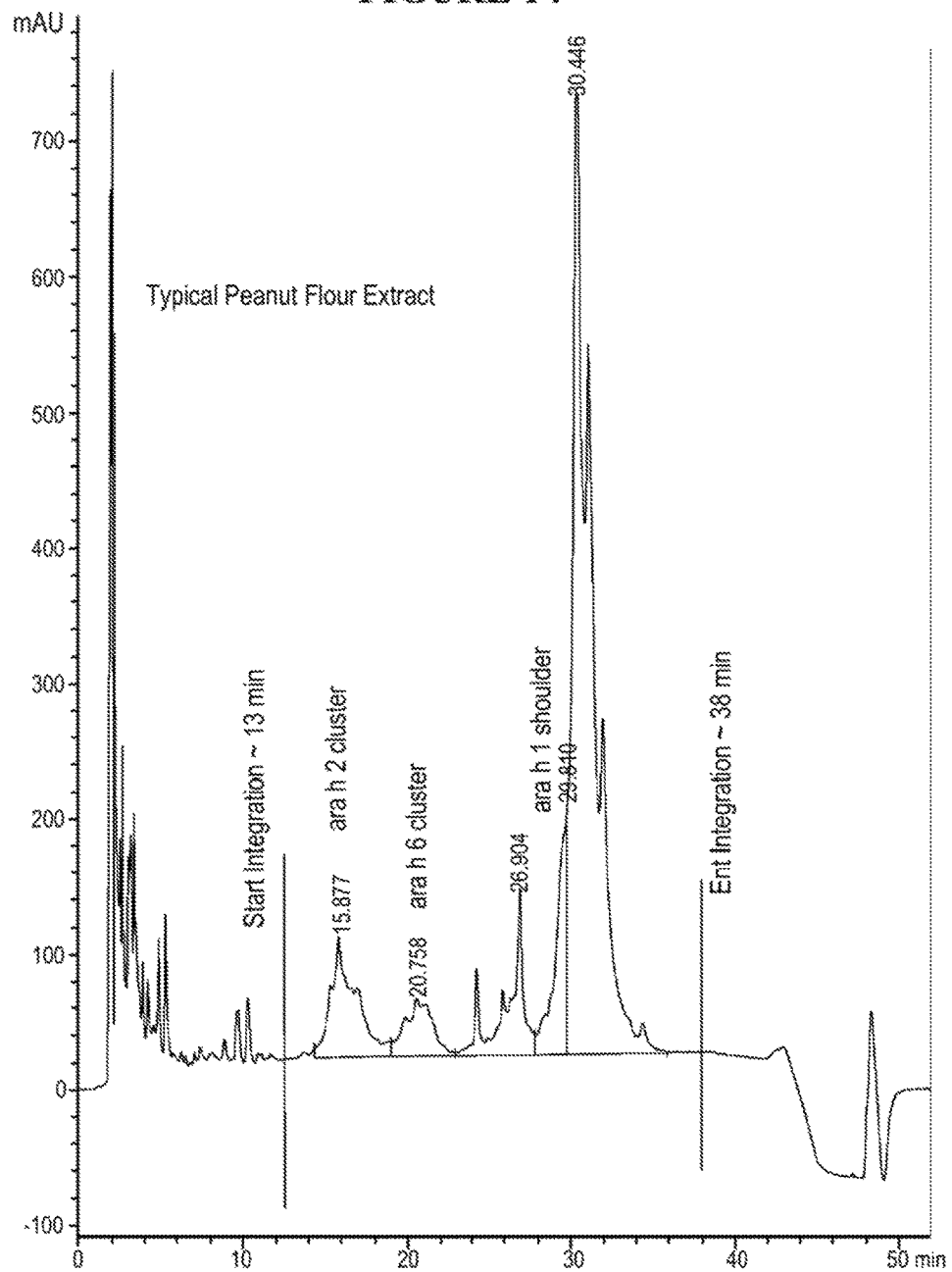
FIG. 14. Typical chromatogram of peanut flour extract, showing integration for each of the Ara h regions. Integration parameters may be adjusted as needed.

Set integration parameters to integrate the entire retention time region of each of the Ara h species, as shown in FIG. 14. FIG. 14 is a graph illustrating a typical chromatogram of a peanut flour extract, showing integration for each of the Ara h regions. Integration parameters may be adjusted as necessary. Some data systems may integrate individual peaks. If so, include the individual peaks so as to represent the total of the Ara h 2, 6 and 1 species, respectively.

Confirm that, in addition to the Ara h regions, that all other peaks within the start and stop of integration are properly integrated. The total area of the sample chromatograms will be sum total of all peak area within the start and stop of integration.

Calculations

1. Calculate the agreement between the area of each of the bracketing standards and the average area of the first 5 standard injections as:

$$\% \text{ Difference} = \frac{(\text{Area Bracketing Std} - \text{Avg. Area Initial 5 Stds})}{\text{Avg. Area Initial 5 Stds}} \times 100$$

2. Calculate the mg/g of the total protein in each sample as follows:

$$\text{mg/g } ara\ h = \frac{\text{Conc. } BSA \text{ Std mg/mL} \times \text{Total Area}}{\text{Avg. Area } BSA \text{ Std.}} \times \frac{\text{Sample Diluent Volume}}{SampleWt \cdot g}$$

Where:

| | |
|---|---|
| Avg. Area of BSA Std. | = Average area of all BSA std injections, including bracketing injections |
| Total Area or Ara h Region | = Total area of sample chromatogram from start to end of integration |
| Sample Diluent Volume | = 20 mL (or sample diluent volume used) |
| Sample weight | = Weight of each peanut flour sample, in g |

3. Calculate the area % of each of the Ara h regions according to:

$$Ara\ h\ \% = \frac{\text{Area } Ara\ h \text{ region}}{\text{Total Area}} \times 100$$

Report the results in area % of the total area for each of the Ara h allergens and, optionally, calculate the total protein found in the extract.

HPLC Method Results

Figure 15:
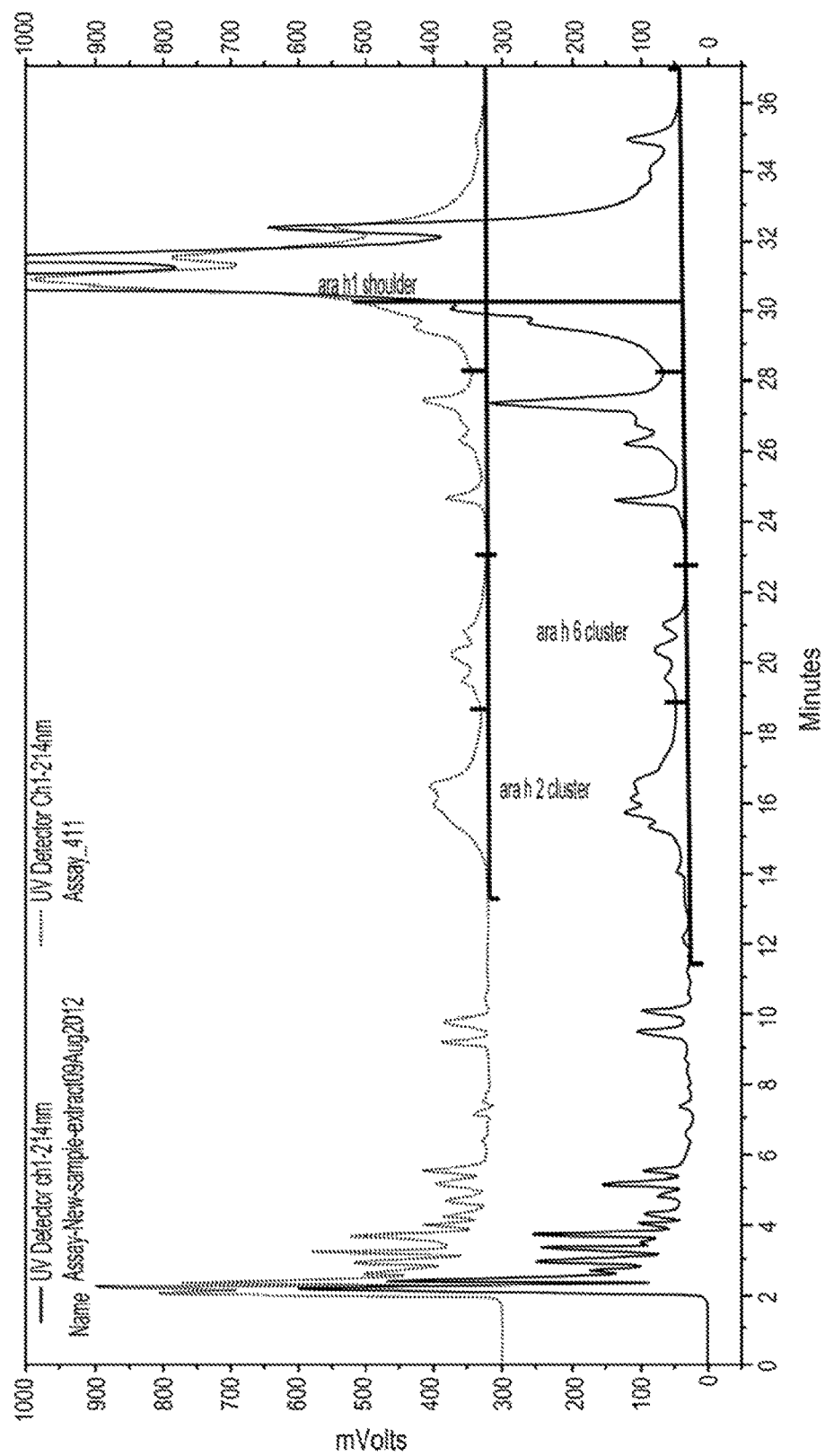
FIG. 15. Results from RP-HPLC extraction showing Ara h1, Ara h2 and Ara h 6 shoulders.

Assay results for the new sample:% Ara h proteins, and % total extractable protein are provided in Table 8 and FIG. 15.

TABLE 8

% Ara h proteins from the sample analysis.

| | | |
|---|---|---|
| Second Manufacturer Sample Extraction | Ara h 2 cluster | 6.94% |
| | Ara h 6 cluster | 2.51% |
| | Ara h 1 shoulder | 10.06% |
| | total protein | 18.55% |
| Peanut Flour 112FA02411 (Golden Peanut Company) | Ara h 2 cluster | 11.31% |
| | Ara h 6 cluster | 5.68% |
| | Ara h 1 shoulder | 10.40% |
| | total protein | 10.23% |

Importantly, this assessment demonstrated that the present methods may be used to characterize peanut allergens in peanut flour lot obtained from a second manufacturer other than the Golden Peanut Company. The data shows that Ara h2 and h6 are almost 50% less by percentage in the second manufacturer and would be rejected by the present inventors for inclusion in a composition described herein as having an Ara h protein content that is deemed too low. Thus, RP-HPLC as described by the present inventors may be used to select lots of peanut flour most likely to demonstrate "efficacy" within a method described herein.

Example 5: HPLC

This protocol establishes the validation parameters and associated acceptance criteria for HPLC Method to Determine ID, and Ara h Protein Integrity in Peanut Flour and Characterized Peanut Antigen Capsules (0.5 mg, 1.0 mg, 10 mg, and 100 mg strengths)." The qualification will determine precision, stability of analytical solutions and specificity (forced degradation and absence of interfering peaks from placebo preparations). This validation represents a method to establish the suitability of the HPLC method for use in determining the amount of peanut protein extracted from raw Peanut Flour samples, and the determination of the integrity of the extracted Peanut Flour proteins in formulated product samples.

HPLC Method

Materials

| | |
|---|---|
| Standard | Quantitation Standard: Bovine Serum Albumin (BSA). Peanut Flour Standard: Golden Peanut. |
| Sample | Peanut Flour API. Placebo Samples: Placebo Blends will be provided from Formulation Development. |
| Column | Zorbax Eclipse Plus C18 4.6 mm × 50 mm, 1.8 pm (P/N: 959941-902) |
| Equipment: | Shimadzu HPLC System equipped with a pump, an autosampler, a column heater and a UV-Vis detector. The system is equipped with Shimadzu Class VP Chromatography Data System Version 7.2. |

Validation Parameters.

Precision

Precision of the assay method will be determined by preparing six samples of placebo blend spiked with Peanut Flour for each of the different product strengths and the raw Peanut Flour sample (1 gram Peanut Flour extracted with 10 mL Tris Buffer—details of the preparation are provided in the method). This reflects a total of 5 sets of 6 samples (4 strengths and the. Peanut Flour). Aliquots of the sample solutions will be injected once each into the HPLC for the determination of Ara h2, Ara h6, and Ara hi shoulder area % values, total % protein extracted and Ara h2/h6% area ratios.

Acceptance Criteria

Report the Ara h2, Ara h6, and Ara hi shoulder area % values, total % protein extracted, Ara h2/h6% area ratios and associated % RSDs. The % RSD of the six Ara h2/h6 ratios determinations is less than or equal to 10% for each sample type.

Stability of Analytical Solutions

Stability of Peanut Flour in standard and sample preparations will be evaluated at the target analytical concentrations). Fresh standard and samples will be prepared and injected once into the HPLC system. The same solutions will be allowed to age refrigerated (5° C.) for up to 3 days. The stability storage time may be extended. Stability will be evaluated at periodic time points by comparing the initial results with the results of the aged solutions. The aged standard and samples will be quantified at each time point with freshly prepared standards. The peak area of BSA will be compared for the standard stability. The peak area of Peanut Flour (Ara h2, h6, and hi shoulder) will be compared for the samples.

Acceptance Criteria

The aged BSA standard preparation is considered stable if the area of BSA is within ±2.0% of the original area. The aged Peanut Flour preparation is considered stable if the area of Ara H2, Ara h6, and the Ara h1 shoulder are within ±5% of the original areas. The sample preparations are considered stable if the area of Ara h2, Ara h6, and the Ara hi shoulder are within ±5% of the original area, and the ratio of Ara h2/h6 is within than ±10% of the original calculated ratio.

Specificity

According to the ICH, specificity "should involve demonstration of the discrimination of the analyte in the presence of impurities/degradation products and/or excipients). This can be accomplished through two approaches: 1) by spiking the drug product with appropriate levels of impurities/degradation products and demonstrating the separation of these impurities/degradation products individually and/or from other components in the sample matrix; and 2) through forced degradation studies.

Forced degradation specificity should include samples stored under relevant stress conditions such as: light, heat, humidity, acid/base hydrolysis and oxidation.

For the purposes of this validation the second approach will be used for demonstration of specificity, as known degradation products are not available. Forced degradation studies will not include light exposure samples as the drug product will be filled into a HDPE or Amber Glass bottle that is subsequently stored in a fiberboard carton. Heat will not be included as the peanut flour has undergone a roasting process.

Excipient Interference

Analyze a placebo preparation for all product strengths. Separately calculate the total peak area of any peaks eluting with the retention time of the Ara h proteins. Compare the total peak area to the respective peak area the Ara h proteins at about 100% concentration.

Acceptance Criteria

Total relative interference: Ara h proteins (Ara h2, h6 and h1 shoulder) is ≤0.5% of 100% level Forced Degradation Acid, base and peroxide will be used to stress peanut flour. A placebo preparation representative of the 0.5 mg peanut flour formulation will be used since this sample contains the most excipient. The placebo preparation will be used to demonstrate absence of active as well as absence of any interfering peaks. A change in the Ara h2/h6 ratio of less than 1.8 or greater than 2.1 will be targeted. The stress conditions described in the following sections may be changed to accommodate particular situations. The sample will be prepared in ample quantity to supply enough material for conducting stress studies. The base stressed samples will be quantitatively neutralized prior to analysis using appropriate volume and strength of 0.1 N HCl.

Degradation will be based on the assay of Peanut Flour in the stressed sample against an unstressed sample. Each sample will be injected once. Aliquots of all forced degradation samples will be sent to the USDA for further characterization and analysis.

Acid Stressed Sample

To a 1 gram sample of Peanut Flour 1.0 mL of 0.1 N HCl will be added and the sample is allowed to stand for up to 24 hours. At the end of the time period the solution will be neutralized with 1.0 mL of 0.1 N NaOH and extracted as described in the test method. A placebo control in the same manner replacing the peanut flour with placebo blend will be prepared.

Base Stressed Sample

To a 1 gram sample of Peanut Flour 1.0 mL of 0.1 N NaOH will be added and the sample allowed to stand for up to 24 hours. At the end of the time period the solution will be neutralized with 1.0 mL of 0.1 N HCl and extracted as described in the test method. A placebo control in the same manner replacing the Peanut Flour with placebo blend will be prepared.

Peroxide Stressed Sample

To a 1 gram sample of peanut flour 1.0 mL of 3% peroxide will be added and allowed to stand for up to 24 hours. A placebo control in the same manner replacing the Peanut Flour with placebo will be prepared.

Acceptance Criteria

Report the results from the USDA. No interfering peaks are observed in the placebo preparation. The Ara h2/h6 ratios of the degraded samples are outside the range of 1.8 to 2.1. The Ara h2/h6 ratio for the non-degraded sample is within the range of 1.8 to 2.1.

Conclusion

The qualification parameters presented in this protocol are intended to demonstrate that CoreRx, Inc. test method TM-074 version: Draft "HPLC Method to Determine ID, and Ara h Protein Integrity in Characterized Peanut Flour and Characterized Peanut Antigen Capsules (0.5 mg, 1.0 mg, 10 mg, and 100 mg strengths)" is suitable for the intended use of determining the integrity of the extracted Peanut Flour proteins in formulated product and raw Peanut Flour samples.

Example 6

This test method provides instructions for the identification of Ara h 2, 6, and 1 proteins in peanut flour by HPLC and the determination of the Peak Area Ratio between Ara h1 and h2.

Equipment
HPLC System
Phenomenex Jupiter C-4, 5 pm, 4.6×150 mm, P/N 00E-4167-E0 or equivalent
Syringe filters, 0.45 pm regenerated cellulose membrane
Centrifugal filters, 10,000 MWCO regenerated cellulose membrane Reagents
Water, E-Pure system or equivalent 2.2. Acetonitrile, HPLC grade; Trifluoroacetic acid (TFA), HPLC grade 2.4. Tris HCl; and 1 N sodium hydroxide.

Reference Standard
Bovine serum albumin (BSA) and Peanut Flour Standard

Reagent Preparation
Mobile Phase A (0.1% v/v TFA in water): Combine 1000 mL water and 1 mL TFA in a 1 L reagent bottle or suitable container and mix well. Scale quantities as needed.

Mobile Phase B (0.1% v/v TFA in 90% Acetonitrile (CAN)): Combine 900 mL ACN and 100 mL water and 1 mL TFA in a 1 L reagent bottle or suitable container and mix well. Scale quantities as needed.

Diluent (20 mM Tris HCl Buffer): Accurately weigh and dissolve approximately 3.15 g Tris HCl in 1 Liter of water. Adjust pH to 8.2±0.1 with 1 N sodium hydroxide.

Standard and Sample Preparation
BSA Working Standard (about 1.0 mg/mL): Accurately weigh approximately 50 mg of BSA Reference Standard into a 50.0 mL volumetric flask. Dissolve and dilute to volume with diluent and mix well. Scale as necessary.

Identification Standard (about 1.0 mg/mL): Accurately weigh 1 gram of peanut flour standard into a 15 mL conical tube. Pipet 10.0 mL of diluent, cap tube and suspend the sample using moderate shaking. Place the sample into a water bath at 60° C. for 3 hours, shaking tube intermittently. Upon completion of the extraction, centrifuge the sample about 15 minutes, or until the supernatant is relatively clear. Filter the supernatant through a 0.45 pm regenerated cellulose membrane filter, discarding the first 1-2 mL. Transfer an aliquot of the sample to an HPLC vial for analysis.

Working Sample Solution
Select no less than ten (10) capsules and empty contents. Accurately weigh 1 gram of composite sample into a 15 mL conical tube. Pipet 10.0 mL of diluent, cap tube and suspend the sample using moderate shaking. Place the sample into a water bath at 60° C. for 3 hours, shaking tube intermittently. Upon completion of the extraction, centrifuge the sample about 15 minutes, or until the supernatant is relatively clear. Filter the supernatant through a 0.45 pm regenerated cellulose membrane filter, discarding the first 1-2 mL. For the 100 mg dosage strength, transfer an aliquot of the sample to an HPLC vial for analysis. For the 0.5 mg, 1 mg and 10 mg dosage strength concentrate the sample 10× with a centrifugal filter. Transfer an aliquot of the sample to an HPLC vial for analysis.

HPLC Conditions

| Column | Phenomenex Jupiter C4, 5 pm, 4.6 × 150 mm |
|---|---|
| Flow Rate | 1.0 mL/min |
| Injection Volume | 10 4 for standard injections, 20 1 1 L for 10 mg and 100 mg samples, 100 !L for 0.5 mg and 1 mg samples |
| Run time | about 52 min |
| Column Temperature | 50° C. |
| UV Detection Wavelength | 214 nm |
| Mobile Phase A (MPA) | 0.1% vb./TFA in water |
| Mobile Phase B (MPB) | 0.1% NO/TFA in 90% ACN |

| | Time (min) | % MPA | % MPB |
|---|---|---|---|
| Gradient Program | 0 | 85 | 15 |
| | 40 | 45 | 55 |
| | 42 | 0 | 100 |
| | 45 | 0 | 100 |
| | 46 | 85 | 15 |
| | 52 | 85 | 15 |

Sequence

Condition the column and system to obtain stable baseline signal and gradient profile. This may include 1 or more runs of zero volume injection, diluent, and BSA standard; BSA Working Standard (5injections); Identification standard, Diluent (1 injection), Sample preparations (1 injection per sample), not to exceed 5 sample injections without injection of a bracketing Working Standard; and Bracketing BSA Working Standard (1 injection).

System Suitability

The Relative Standard Deviation (RSD) for the BSA peak area in the first five Working Standard injections is not more than (NMT) 2.0%.

The area of the bracketing standard matches the average area of the initial 5 injections within 2%.

Integration Settings

Exclude any detected peaks observed before about 13 min and after about 38 min from integration and calculations. The run time from 38 min to end is designed as a column wash out.

Figure 16:
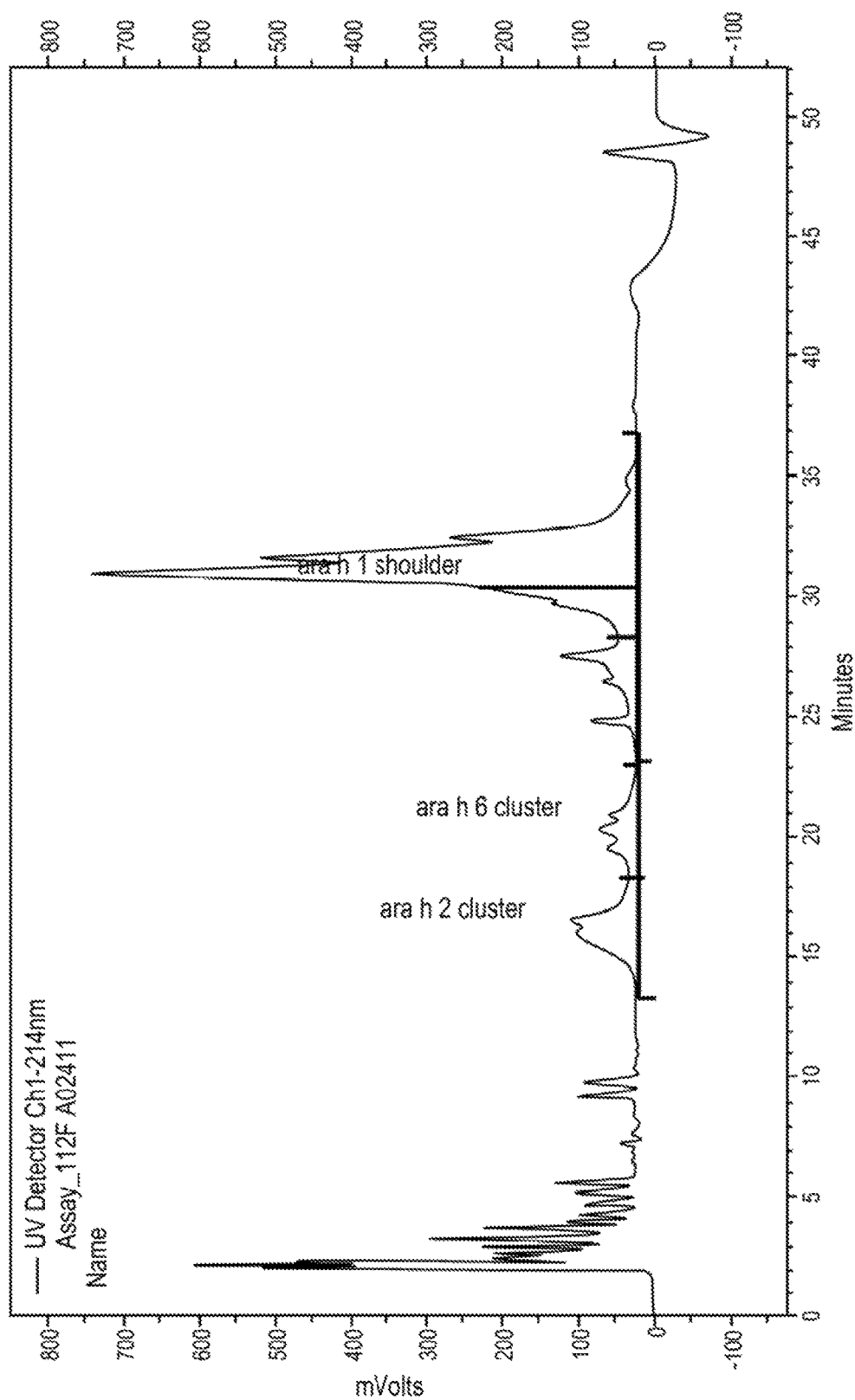
FIG. 16. Full Scale Chromatogram Ara h proteins 2, 6 and 1.

Set integration parameters to integrate the entire retention time region of each of the Ara h species, as shown in FIG. 16.

Confirm that in addition to the Ara h regions, that all other peaks within the start and stop of integration are properly integration. The total area of the sample chromatogram will be the sum total of all peak area within the start and stop of integration.

Calculations

A) Protein Recovered from Peanut Flour (Extractable Protein) Calculate the mg/g of Ara h total protein, and of each Ara h region:

$$\text{mg/g } ara \; h = \frac{R_u}{R_s} \times C_{STD} \times \frac{V_{Sample}}{Wt_{sample}}$$

where:

| | |
|---|---|
| Ru | Total Ara h Protein Peak Area or Ara h Species Peak Area in the Working Sample |
| Rs | Average BSA Peak Area in all Working Standards |
| $C_{STD}$ | BSA Working Standard Concentration (mg/mL) |
| $V_{sample}$ | Total Diluent Volume of the Working Sample (10.0 mL) |
| $Wt_{sample}$ | Weight of peanut flour sample (g) |

B) Calculate the % of each Ara h region (See FIG. 16):

$$Ara\ h\ \% = \frac{Ara\ h\ mg/g}{Total\ Protein\ mg/g} \times 100$$

Ratio of Ara h2 to 6:

$$Ara\ h2/Arah6\ Ratio = \frac{AreaArah2}{AreaArah6}$$

where:
AreaArah2=Ara h2 Protein Peak Area
AreaArah6=Ara h6 Protein Peak Area
Identification.

Compare the sample chromatogram (see, e.g., FIG. 16) to the Identification Standard. The Ara h2, Ara h6, and Ara h1 shoulder regions elute are present and their respective retention times windows are similar.

Example 7: Stability Studies and Peanut Flour Protein Evaluation

Presented herein are the HPLC results from the T=0 stability study. Results are reported as Area % for the different formulations and are presented in Table 9. In addition to presenting only the Area % values, h2/h6 ratios are provided. This value is typically between 1.8 and 2.1 for all formulations evaluated. Given the formulation and sample preparation variations, results for this value remain consistent for all sample preparations. There is a high degree of variability with the h1 shoulder. In addition, some variations are observed for variations in total peak area (sample concentration variability). Supporting data is provided in Table 10.

TABLE 9

Initial testing results for peanut flour capsules (100 mg and 0.5 mg)

| | Acquisition | Dosage | Area % | | | h2/h6 |
|---|---|---|---|---|---|---|
| Sample ID | Date | size mg | h2 | h6 | h1 shoulder | ratio |
| Lot 054-12022D | Nov. 30, 2012 | 100 mg | 10.11 | 5.29 | 11.63 | 1.91 |
| Lot 054-12023D | Nov. 30, 2012 | 100 mg | 9.92 | 5.14 | 11.19 | 1.93 |
| Lot 054-12024A | Nov. 30, 2012 | 0.5 mg | 11.22 | 6.05 | 9.49 | 1.85 |
| Lot 054-12025A | Nov. 30, 2012 | 0.5 mg | — | — | — | N/A |
| Lot 054-12024A - Prep 2 | Dec. 4, 2012 | 0.5 mg | 10.91 | 5.45 | 13.77 | 2.00 |
| *Lot 054-12025A - Prep 2 | Dec. 4, 2012 | 0.5 mg | 21.27 | 11.30 | 10.70 | 1.88 |

*Peaks were about 30% of the peak area of the 024A Sample

TABLE 10

Forced Degradation Stability Results Demonstrating Changes in h1/h2 Peak Area Ratios

| Base (0.1N NaOH, 24 hours) | ara h 2 cluster | 16.24% | 1.40 |
|---|---|---|---|
| | ara h 6 cluster | 11.62% | |
| | ara h 1 shoulder | 12.60% | |
| | total protein | 3.99% | |
| Acid (0.1N HCl, 24 hours) | ara h 2 cluster | 18.52% | 1.63 |
| | ara h 6 cluster | 11.37% | |
| | ara h 1 shoulder | 10.75% | |
| | total protein | 3.86% | |
| Peanut Flour 112FA02411 (Control) | ara h 2 cluster | 11.30% | 1.99 |
| | ara h 6 cluster | 5.68% | |
| | ara h 1 shoulder | 10.40% | |
| | total protein | 10.23% | |

FIG. 20 shows the effects of treating the peanut flour for 24 hours with 3% peroxide. The HPLC method was able to detect significant changes to the Ara h6 and h2 peaks. Thus, the method is appropriate as a method to determine long term stability of the peanut flour containing proteins.

Companies develop methods to determine the effects of long term storage of products, however, a method has not been described for peanut flour. The methods described herein represent a new method which may be used for stability determination of a composition described herein or a comparable formulation.

Figure 17:
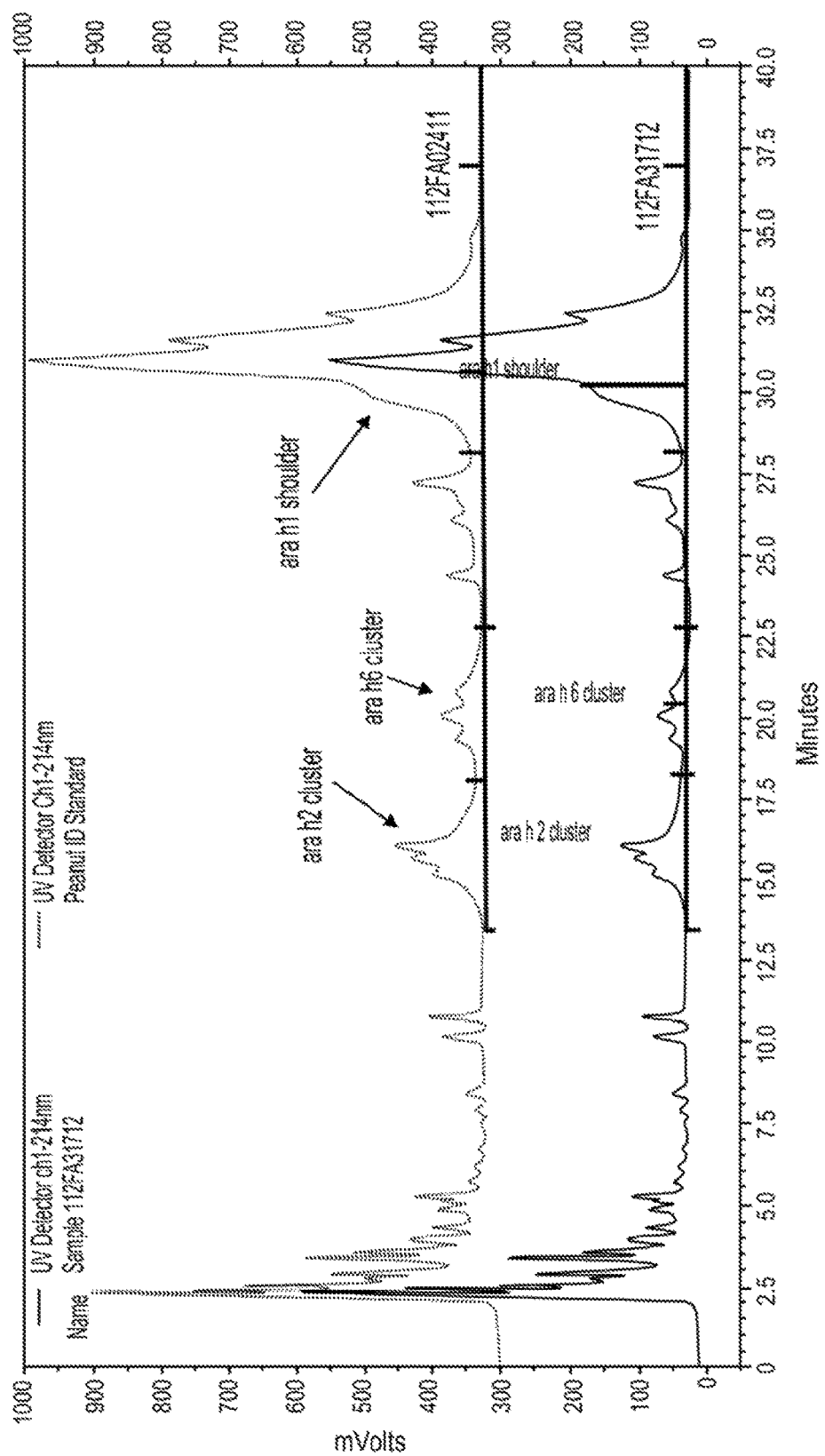
FIG. 17: Chromatogram results from RP-HPLC analysis of 112FA31712 RP-HPLC.
Figure 18:
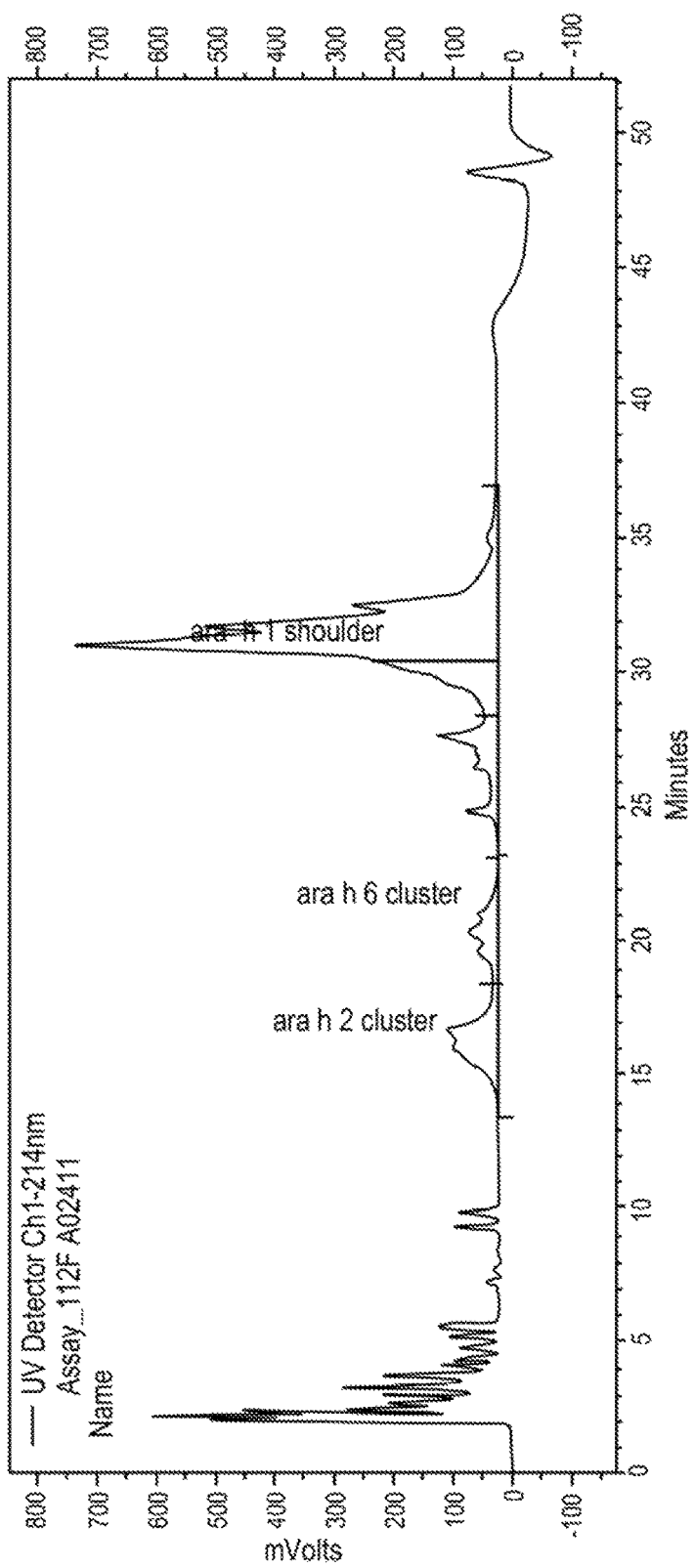
FIG. 18: Chromatogram results from RP-HPLC analysis of 112FA02411 (GMP).
Figure 19:
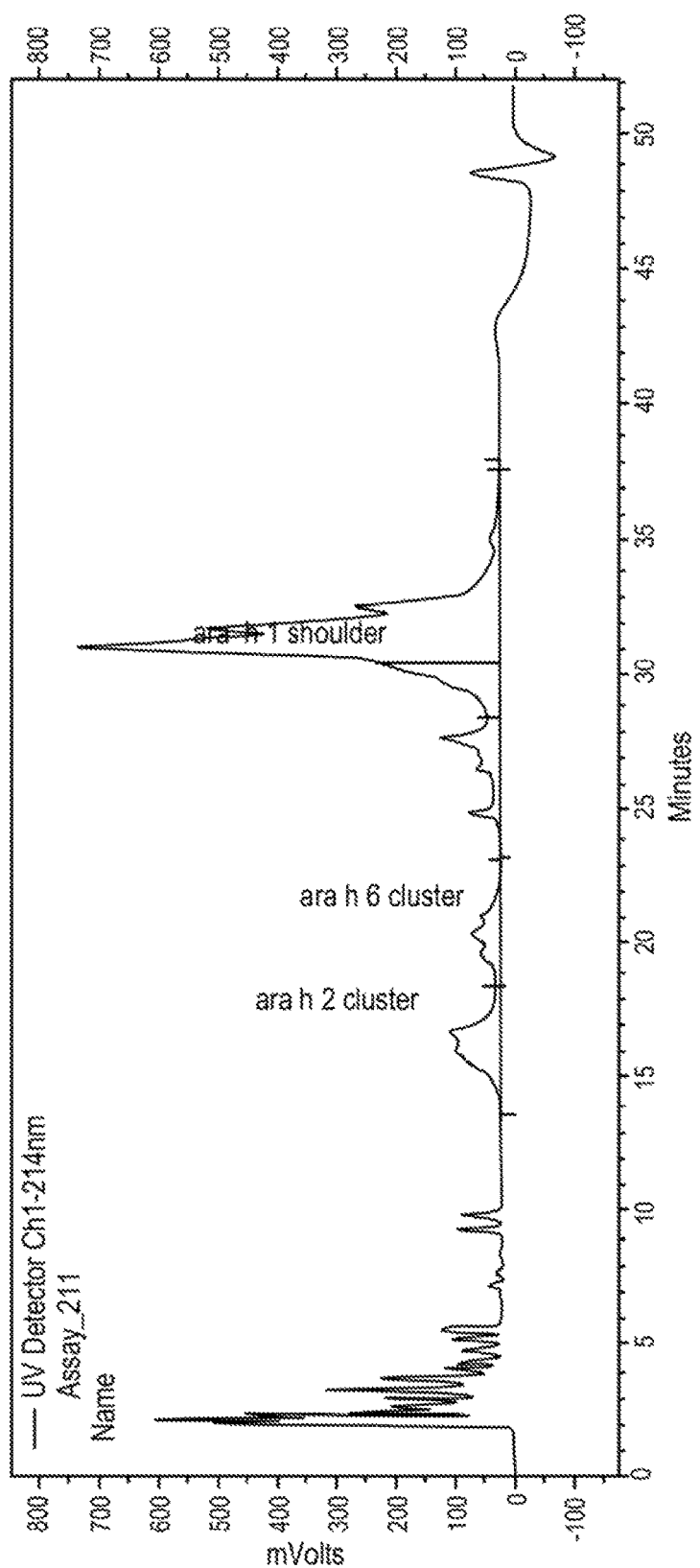
FIG. 19: Chromatogram results from RP-HPLC analysis of 111FA36211 (Non-GMP).

Ara Assay results for Batch 112FA31712: % Ara h proteins, % total extractable protein and h2/h6 ratios are provided in Table 11 and FIG. 17.

TABLE 11

% Ara h proteins from the sample analysis.

| Peanut Flour Batch | Peak Name | Ara h % | h2/h6 ratio |
|---|---|---|---|
| Peanut Flour ID Standard (Batch # 112FA02411) | Ara h 2 cluster | 11.26% | 1.91 |
| | Ara h 6 cluster | 5.90% | |
| | Ara h 1 shoulder | 10.34% | |
| | total protein | 10.89% | |
| Peanut Flour 112FA31712 | Ara h 2 cluster | 10.69% | 2.14 |
| | Ara h 6 cluster | 5.00% | |
| | Ara h 1 shoulder | 9.73% | |
| | total protein | 8.44% | |

Provided herein are the results from the RP-HPLC method evaluation of peanut flour protein method. Samples were prepared according to the method provided herein. A total of five samples were tested. Percent (%) Ara h proteins, and % total extractable protein are provided in Table 12. Results are provided in Table 14 and chromatograms are provided in FIGS. 18-21.

Samples placed at 40° C./75% RH and 60° C. will be analyzed.

TABLE 12

% Ara h proteins from test 1.

| Peanut Flour Lot | Ara h 2 | Ara h 6 | Ara h 1 (shoulder) | % Protein |
|---|---|---|---|---|
| 111FA36111 | 11.40 | 5.29 | 9.79 | 11.26 |
| 111FA36211 | 11.20 | 5.67 | 9.85 | 11.03 |
| 112FA02411 (Non GMP) | 11.31 | 5.68 | 10.41 | 10.23 |
| 112FA02411 (GMP) | 10.58 | 5.79 | 10.16 | 10.25 |

TABLE 13

% Ara h proteins from test 2:

| Peanut Flour Lot | Ara h 2 Analyst 1 | Ara h 2 Analyst 2 | Ara h 6 Analyst 1 | Ara h 6 Analyst 2 | Ara h 1 (shoulder) Analyst 1 | Ara h 1 (shoulder) Analyst 2 | % Protein Analyst 1 | % Protein Analyst 2 |
|---|---|---|---|---|---|---|---|---|
| 111FA36111 | 10.60% | 12.29% | 5.59% | 5.77% | 8.82% | 9.73% | 9.57% | 10.08% |
|  | % Match: 86.31% | | % Match: 96.76% | | % Match: 90.70% | | % Match: 94.94% | |
| 111FA36211 | 10.65% | 12.02% | 5.48% | 5.67% | 11.14% | 9.36% | 9.93% | 10.02% |
|  | % Match: 88.58% | | % Match: 96.63% | | % Match: 118.97% | | % Match: 99.17% | |
| 112FA02411 | 10.62% | 11.95% | 5.93% | 6.30% | 9.91% | 9.68% | 9.38% | 9.24% |
|  | % Match: 88.83% | | % Match: 94.02% | | % Match: 102.42% | | % Match: 101.58% | |
| 112FA02411 | NA | 12.18% | NA | 6.28% | NA | 10.58% | NA | 9.92% |

A two-month accelerated study was conducted in which HPLC was utilized to assess changes in Ara h proteins over time and to determine the percent loss on drying (% LOD). LOD is a measure of moisture update and is minimized using the present formautions. Briefly, the bottles were placed in a heat and humidity controlled stability chamber at 60° C./75% RH for up to two months. Sample capsules were assayed by HPLC and for % LOD. The data show that after two months at accelerated stability conditions there were no significant changes in the proportion of the Ara h proteins compared to control values as demonstrated in the following table. In addition, the % LOD, or moisture content, did not change over time without dessicant, but was somewhat improved, particularly at the two month time point, when dessicant was included in the bottles.

| | | Lot Number | |
|---|---|---|---|
| | | 054-120220 (100 mg capsule) | 054-12024A (0.5 mg capsule) |
| T = 0 | h2 | 10.11 | 11.22 |
| | h6 | 5.29 | 6.05 |
| | h1 shoulder | 11.63 | 9.49 |
| | % LOD | 6.09 | 5.92 |

| | | With desiccant | Without desiccant | With desiccant | Without desiccant |
|---|---|---|---|---|---|
| T = 1 mo | h2 | 9.46 | 9.62 | 11.98 | 12.35 |
| | h6 | 4.86 | 4.90 | 5.91 | 6.21 |
| | h1 shoulder | 14.82 | 14.95 | 13.27 | 12.72 |
| | % LOD | 5.35 | 5.96 | 5.67 | 6.74 |
| T = 2 mo | h2 | 9.06 | 9.36 | 12.29 | 12.02 |
| | h6 | 4.83 | 4.99 | 6.14 | 6.01 |
| | h1 shoulder | 11.6 | 10.6 | 9.7 | 10.2 |
| | % LOD | 4.93 | 5.62 | 3.75 | 5.77 |

Based on these data, compositions were established for the five dosage levels. A dessicant pouch may be included in each bottle containing capsules.

Example 8: Sodium Dodecyl Sulfate-Polyacrylamide Gel Electrophoresis (SDS-PAGE)

Supernatant fractions of each sample were mixed with 3× sample loading buffer, then incubated for 10 minutes at 65° C. and subjected to sodium dodecyl polyacrylamide gel electrophoresis (SDS-PAGE) on a 4-20% Novex Tris-HCl pre cast gel (Invitrogen Corporation, Carlsbad, Calif.), where individual proteins were separated according to size (a MW marker contained 10, 15, 20, 25, 37, 50, 75, 100, 150, 250 size control bands) and stained with Gel-Code Blue stain (Pierce, Rockford, Ill.) for 1 hour, destained according to the manufacturer's instructions and photographed. Differences are visually assessed.

Example 9: Western Blot Analysis

Samples were submitted to SDS-PAGE, and transferred to a PVDF membrane. The membrane was then blocked for 1 hour using 5% Blotto (5% dry milk dissolved into PBS containing 0.5% TWEEN (PBST)). After blocking the membrane, the primary antibody was diluted in 5% blotto, added to the membrane, and incubated for 1 hour. The primary antibodies used were chicken anti-Ara h 1, Ara h 2 and Ara h 3 antibodies at 1:5000 or human serum at 1:10 dilution.

For IgE Western blots, membranes were blocked in 2% Blocker® BLOTTO in Tris Buffered Saline (TBS; Thermo Scientific) for 15 minutes and incubated overnight with 1:10 dilution in PBST of patient sera from allergic or non-allergic individuals (identified from positive or negative skin prick test results, respectively). After incubation with primary antibodies, the membranes were washed 3 times with PBST and incubated with the either anti-chicken IgY at 1:100,000 or anti-human IgE at 1:10,000 horseradish peroxidase (HRP)-labeled secondary antibody diluted in 2% BLOTTO for 30 minutes. The membranes were then washed 3 times with PBST and 2 times with PBS and incubated with ECL-Plus Western substrate (Amersham Bioscience Corp., Piscataway, N.J.). The signal was then visualized using a CCD camera system (Fuji Photo Film Co., Ltd., Duluth, Ga.).

Antibodies Used in the Western Blotting

The anti-Ara h 1, Ara h 2 and Ara h 3 antibodies used in the Western blot analysis were custom manufactured by Sigma Immunosys (The Woodlands, Tex.). IgE from peanut allergic individuals was collected at Tulane Health Science Center (New Orleans, La.) and approved in accordance with the rules and regulation of the institutional review board of this institution. Horseradish peroxidase (HRP)-conjugated goat anti-chicken IgG and anti-human IgE are commercially available from Sigma Chemical Company (St. Louis, Mo.). The ECL Western Substrate kit is commercially available from Amersham Bioscience Corp. (Piscataway, N.J.).

Example 10: Indirect ELISA with Chicken-Anti-Ara h 1

An Ara h1 ELISA as been developed to demonstrate that three isolated lots are entirely consistent with each other. The extracted samples were normalized against each other for total protein content as determined by Å 280. The amount of Ara h1 may be from about 16-25% of total extracted protein in TRIS extracted peanut flour.

Figure 4:
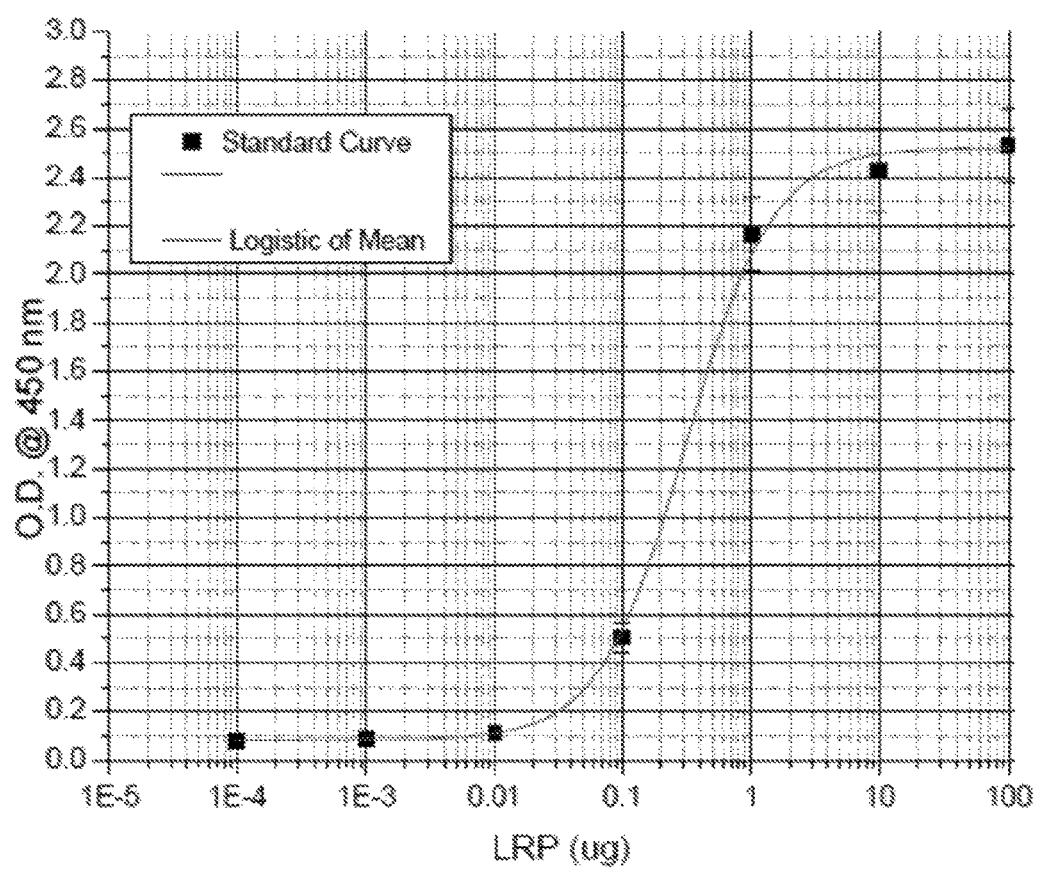
FIG. 4 provides a standard curve for the indirect ELISA with chicken anti-Ara h1.
Figure 5:
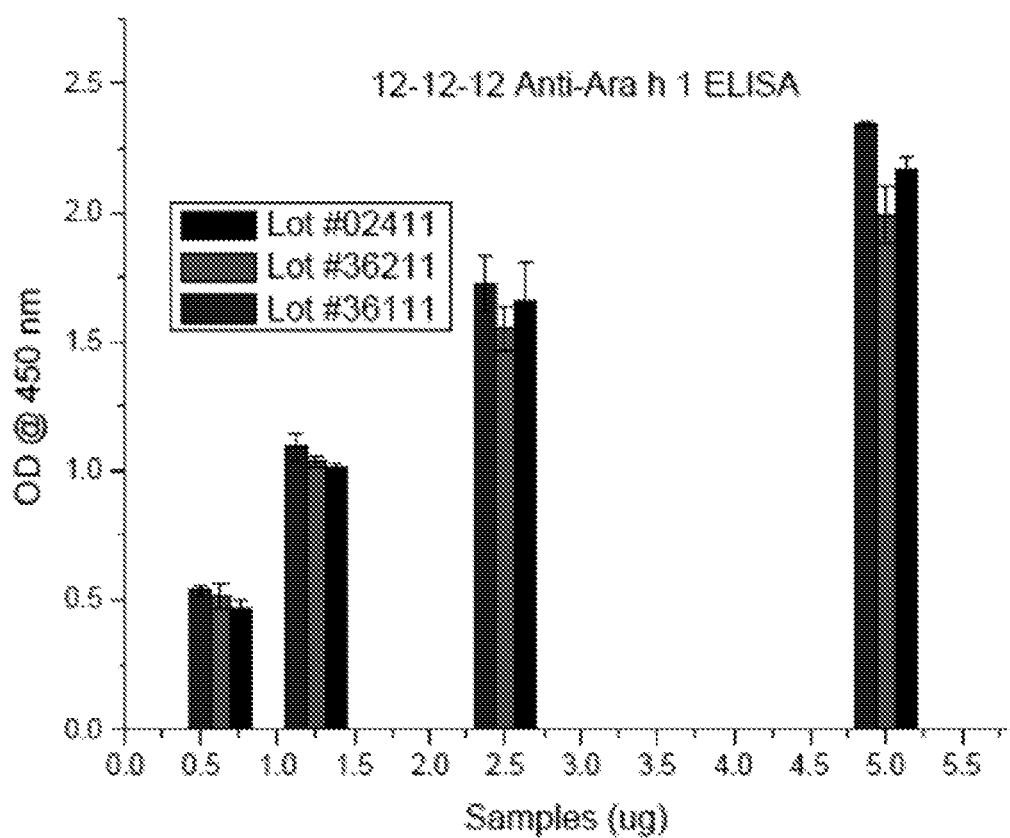
FIG. 5 illustrates a graph of anti-Ara h1 ELISA results. Columns are from left to right for each data set: Lot #36111 (left), Lot #36211 (middle), and Lot #02411 (right).
Figure 6:
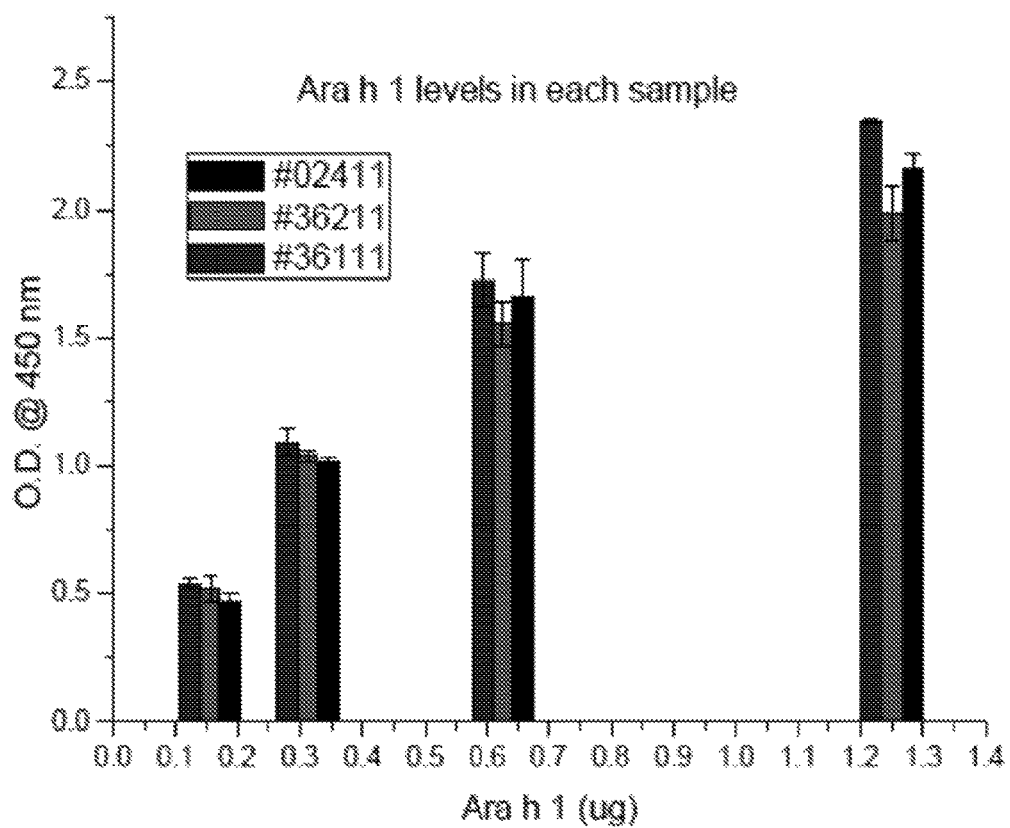
FIG. 6 illustrates another graph demonstrating Ara h1 levels in each sample as determined by the anti-Ara h1 ELISA. Columns are from left to right for each data set: Lot #36111 (left), Lot #36211 (middle), and Lot #02411 (right).

A. FIG. 4 illustrates a standard curve of our control roasted peanut sample

B. Detection of Ara h 1 in the three peanut Lot numbers (each in triplicate).

C. Levels (μgs) of Ara h 1 in each lot number. This is done by assuming that Ara h 1 is 25% of total peanut protein, we multiply the concentration of total peanut protein used/well (from Panel B) by 0.25 to get these values.

D. The most reliable information comes from the lower protein concentrations and the 1.25 μg sample per well is the ideal amount of sample to use for each ELISA to show consistency because the resultant O.D. is in the middle of the standard curve (most sensitive to change in concentration).

E. In conclusion, the levels of Ara h 1 are statistically identical from lot-to-lot.

Protocol for Indirect ELISA:

1. Coat 96-well plate (Thermo Scientific Immulon 4HBX) with protein samples suspended in 50 μl of 0.1 M NaHCO$_3$, pH 9.5. Incubate at 37° C. for 1 hour.

2. Wash 3× with 300 μl/well PBST (0.05% Tween® 20).

3. Block with 5% milk in PBS (250 μl/well) for 1 hour at 37° C.

4. Wash 3× with 300 μl/well PBST (0.05% Tween® 20).

5. Add 1:1000 chicken anti-Ara h 1 antibody in PBS (50 μl/well) and incubate for 1 hour at 37° C.

6. Wash 3× with 300 μl/well PBST (0.05% Tween® 20)

7. Add 1:10,000 anti-chicken-HRP antibody in PBS (50 μl/well) and incubate for 1 hour at 37° C.

8. Wash 3× with 300 μl/well PBST (0.05% Tween® 20). Last wash with PBS.

9. Add 100 μl/well SureBlue TMB peroxidase substrate (KPL). Stop reaction with 1% HCl.

10. Measure absorbance at 450 nm.

REFERENCES

1. Thyagarajan A, Jones S M, Kemper A R, Pons L, Kulis M, Woo C, Yoo S, Burks A W, Shreffler W G: Basophil Suppression in Peanut Allergic Subjects undergoing Peanut Oral Immunotherapy (OIT), *Journal of Allergy and Clinical Immunology* 2009, 123:S214-S214.
2. Burks A W: Early peanut consumption: postpone or promote?, *J Allergy Clin Immunol* 2009, 123:424-425.
3. Burks W: Diagnosis of allergic reactions to food, *Pediatr Ann* 2000, 29:744-752.
4. Burks W: Current understanding of food allergy, *Ann NY Acad Sci* 2002, 964:1-12.
5. Burks W: Skin manifestations of food allergy, *Pediatrics* 2003, 111:1617-1624.
6. Burks W: Peanut allergy: a growing phenomenon, *J Clin Invest* 2003, 111:950-952.
7. Burks W: Food allergens, *Clin Allergy Immunol* 2004, 18:319-337.
8. Maloney J M, Sampson H A, Sicherer S H, Burks W A: Food allergy and the introduction of solid foods to infants: a consensus document, *Ann Allergy Asthma Immunol* 2006, 97:559-560; author reply 561-552.
9. Skripak J M, Wood R A: Mammalian milk allergy: avoidance strategies and oral desensitization, *Curr Opin Allergy Clin Immunol* 2009, 9:259-264.
10. Buchanan A D, Green T D, Jones S M, Scurlock A M, Christie L, Althage K A, Steele P H, Pons L, Helm R M, Lee L A, Burks A W: Egg oral immunotherapy in nonanaphylactic children with egg allergy, *J Allergy Clin Immunol* 2007, 119:199-205.
11. Sicherer S H, Wood R A, Stablein D, Burks A W, Liu A H, Jones S M, Fleischer D M, Leung D Y, Grishin A, Mayer L, Shreffler W, Lindblad R, Sampson H A: Immunologic features of infants with milk or egg allergy enrolled in an observational study (Consortium of Food Allergy Research) of food allergy). *J Allergy Clin Immunol* 2010, 125:1077-1083 e1078. PMCID: PMC2868273
12. Hofmann A M, Scurlock A M, Jones S M, Palmer K P, Lokhnygina Y, Steele P H, Kamilaris J, Burks A W: Safety of a peanut oral immunotherapy protocol in children with peanut allergy, *J Allergy Clin Immunol* 2009, 124:286-291, 291 e281-286. PMCID: PMC2731305.
13. Joshi, P., S. Mofidi, and S. H. Sicherer, Interpretation of commercial food ingredient labels by parents of food-allergic children. *J Allergy Clin Immunol*, 2002. 109(6): p. 1019-21.
14. Altschul, A. S., et al., Manufacturing and labeling issues for commercial products: relevance to food allergy. *J Allergy Clin Immunol*, 2001. 108(3): p. 468.
15. Vierk, K., et al., Recalls of foods containing undeclared allergens reported to the U S Food and Drug Administration, fiscal year 1999. *J Allergy Clin Immunol*, 2002. 109(6): p. 1022-6.
16. Sicherer, S. H., A. W. Burks, and H. A. Sampson, Clinical features of acute allergic reactions to peanut and tree nuts in children. *Pediatrics*, 1998. 102(1): p. e6
17. Sampson, H. A., et al., Symposium on the definition and management of anaphylaxis: summary report. *J Allergy Clin Immunol*, 2005. 115(3): p. 584-91.
18. Skolnick, H. S., et al., The natural history of peanut allergy. *J Allergy Clin Immunol*, 2001. 107(2): p. 367-74.
19. Bock, S. A., A. Munoz-Furlong, and H. A. Sampson, Fatalities due to anaphylactic reactions to foods. *J Allergy Clin Immunol*, 2001. 107(1): p. 191-3.
20. Frew, A. J., 25. Immunotherapy of allergic disease. *J Allergy Clin Immunol*, 2003. 111(2 Suppl): p. S712-9.
21. Wilson, D. R., M. T. Lima, and S. R. Durham, Sublingual immunotherapy for allergic rhinitis: systematic review and meta-analysis. *Allergy*, 2005. 60(1): p. 4-12.
22. Lehrer, S. B., et al., Immunotherapy for food allergies. Past, present, future. *Clin Rev Allergy Immunol*, 1999. 17(3): p. 361-81.
23. Oppenheimer, J. J., et al., Treatment of peanut allergy with rush immunotherapy. *J Allergy Clin Immunol*, 1992. 90(2): p. 256-62.
24. Nelson, H. S., et al., Treatment of anaphylactic sensitivity to peanuts by immunotherapy with injections of aqueous peanut extract. *J Allergy Clin Immunol*, 1997. 99(6 Pt 1): p. 744-51.

25. Kim, E. H., et al., Sublingual immunotherapy for peanut allergy: clinical and immunologic evidence of desensitization. *J Allergy Clin Immunol*, 2011. 127(3): p. 640-6 e1.
26. Varshney, P., et al., A randomized controlled study of peanut oral immunotherapy: clinical desensitization and modulation of the allergic response. *J Allergy Clin Immunol*, 2011. 127(3): p. 654-60.
27. Bousquet, J., Primary and secondary prevention of allergy and asthma by allergen therapeutic vaccines. *Clin Allergy Immunol*, 2004. 18: p. 105-14.
28. Kapsenberg, M. L., et al., The paradigm of type 1 and type 2 antigen-presenting cells. Implications for atopic allergy. *Clin Exp Allergy*, 1999. 29 Suppl 2: p. 33-6
29. Secrist, H., R. H. DeKruyff, and D. T. Umetsu, Interleukin 4 production by CD4+ T cells from allergic individuals is modulated by antigen concentration and antigen-presenting cell type. *J Exp Med*, 1995. 181(3): p. 1081-9.
30. Blumchen, K., et al., Oral peanut immunotherapy in children with peanut anaphylaxis. *J Allergy Clin Immunol*, 2010. 126(1): p. 83-91 e1.
31. Jones, S. M., et al., Clinical efficacy and immune regulation with peanut oral immunotherapy. *J Allergy Clin Immunol*, 2009. 124(2): p. 292-300, 300 e1-97.
32. Narisety, S. D., et al., Open-label maintenance after milk oral immunotherapy for IgE-mediated cow's milk allergy. *J Allergy Clin Immunol*, 2009. 124(3): p. 610-2.
33. Skripak, J. M., et al., A randomized, double-blind, placebo-controlled study of milk oral immunotherapy for cow's milk allergy. *J Allergy Clin Immunol*, 2008. 122(6): p. 1154-60.
34. Bock, S. A. and F. M. Atkins, Patterns of food hypersensitivity during sixteen years of double-blind, placebo-controlled food challenges. *J Pediatr*, 1990. 117(4): p. 561-7.
35. Burks A W, Jones S M, Wood R A, Fleischer D M, Sicherer S H, Lindblad R, Stablein D, Henning A K, Vickery B P, Liu A H, Scurlock A M, Shreffler W G, Plaut M, and Sampson H A for the Consortium of Food Allergy Research. Oral Immunotherapy for Treatment of Egg Allergy in Children. *N Engl J Med*, 2012 Jul. 19; 367: 233-243.
36. Bock S A, Sampson H A, Atkins F M, Zeiger R S, Lehrer S, Sachs M et al. Double-blind, placebo-controlled food challenge (DBPCFC) as an office procedure: A manual. *J Allergy Clin Immunol* 1988; 82:986-97.
37. Sicherer S H. Food allergy: when and how to perform oral food challenges, *Pediatr Allergy Immunol* 1999; 10(4):226-34.

ABBREVIATIONS

| | |
|---|---|
| ACE | Angiotensin-converting enzyme inhibitors |
| AE | Adverse Event |
| Ag | Antigen |
| ARB | Angiotensin-receptor blockers |
| ARC | Allergen Research Corporation |
| CFR | US Code of Federal Regulations |
| CFSE | Carboxyfluorescein Succinimidyl Ester |
| CPNA | Characterized Peanut Allergen |
| CRC | Clinical Research Center |
| CRF | Case Report Form |
| CTC | Common Toxicity Criteria |
| DBPCFCs = OFC | Double-Blind, Placebo-Controlled Food Challenges - Oral Food Challenge |
| DSMB | Data Safety Monitoring Board |
| EC | Ethics Committee |
| FDA | US Food and Drug Administration |
| cGCP | Current Good Clinical Practice |
| ICH | International Conference on Harmonization |
| IFNg | Interferon Gamma |
| IgA | Immunoglobulin A |
| IgE | Immunoglobulin E |
| IgG | Immunoglobulin G |
| IL | Interleukin |
| IND | Investigational New Drug Application |
| IRB | Institutional Review Board |
| $kU_A/L$ | Kilounits of Antibody per Liter |
| MedDRA | Medical Dictionary for Regulatory Activities |
| OFC = DBPCFC | Oral Food Challenge - Double Blind Placebo Controlled Food Challenge |
| OIT | Oral Immunotherapy |
| PI | Principal Investigator |
| PST | Prick Skin Tests |
| SAE | Serious Adverse Event |
| SAR | Serious Adverse Reaction |
| SUSAR | Suspected Serious Adverse Reaction |
| Th1 | T Helper 1 |
| Th2 | T Helper 2 |
| TLR | Toll-like Receptor |
| Tr1 | T Regulatory 1 |
| Tregs | Regulatory T cells |

While preferred embodiments have been shown and described herein, it will be obvious to those skilled in the art that such embodiments are provided by way of example only. Numerous variations, changes, and substitutions will now occur to those skilled in the art without departing from the embodiments. It should be understood that various alternatives to the embodiments described herein may be employed in practicing the embodiments. It is intended that the following claims define the scope of the embodiments and that methods and structures within the scope of these claims and their equivalents be covered thereby.

What is claimed is:

1. A method for treating peanut allergy in a subject, comprising:
    selecting a subject having a peanut allergy;
    orally administering to the subject a pharmaceutical composition comprising:
        peanut flour comprising 0.45 mg to 550 mg peanut protein;
        one or more diluents in an amount of from 1% to 99% w/w of the composition; and
        one or more lubricants in an amount of from 0.01% to 10% w/w of the composition.
2. The method of claim 1, wherein the pharmaceutical composition is administered daily over a period of at least two weeks.
3. The method of claim 1, wherein the pharmaceutical composition is formulated for oral administration.
4. The method of claim 1, wherein the pharmaceutical composition is formulated as a capsule, a tablet, a mini-tablet, a powder, or a sprinkle.
5. The method of claim 1, wherein the pharmaceutical composition is formulated as a food product.
6. The method of claim 1, wherein the one or more diluents is selected from the group consisting of alginic acid and salts thereof; a cellulose derivative; microcrystalline dextrose; amylose; magnesium aluminum silicate; polysaccharide acids; bentonite; gelatin; polyvinylpyrrolidone/vinyl acetate copolymer; crosspovidone; povidone; starch; pregelatinized starch; tragacanth; dextrin; a sugar; dicalcium phosphate; a natural or synthetic gum; polyvinylpyrrolidone; larch arabogalactan; Veegum®; polyethylene glycol; waxes; sodium alginate; sodium starch glycolate; a cross-linked starch; a cross-linked polymer; a cross-linked polyvinylpyrrolidone; alginate; a clay; sodium starch glycolate; a natural sponge; a surfactant; a resin; citrus pulp; sodium lauryl sulfate; sodium lauryl sulfate in combination with starch; and combinations thereof.

7. The method of claim 1, wherein the one or more lubricants is selected from the group consisting of stearic acid, calcium hydroxide, talc, corn starch, sodium stearyl fumerate, alkali-metal and alkaline earth metal salts, waxes, boric acid, sodium benzoate, sodium acetate, sodium chloride, leucine, a polyethylene glycol (PEG), a methoxypolyethylene glycol, propylene glycol, sodium oleate, glyceryl behenate, glyceryl palmitostearate, glyceryl benzoate, magnesium lauryl sulfate, sodium lauryl sulfate, and combinations thereof.

8. The method of claim 1, wherein the pharmaceutical composition is formulated in a dose of 0.45 mg to 0.55 mg, 0.9 mg to 1.1 mg, 9.0 mg to 11.0 mg, 90 mg to 110 mg, 427.5 mg to 522.5 mg, or 450 mg to 550 mg of peanut protein.

9. The method of claim 1, wherein the pharmaceutical composition comprises peanut flour in a concentration from 7.2% to 16.5%.

10. A method of identifying a pharmaceutical composition for treatment of peanut allergy in a subject, comprising:
determining the amounts of Ara h1, Ara h2 and Ara h6 in a sample of peanut flour by RP-HPLC;
comparing the amounts of Ara h1, Ara h2 and Ara h6 in the sample to amounts of Ara h1, Ara h2 and Ara h6 in a reference standard; and
identifying a pharmaceutical composition for treatment of peanut allergy in a subject, wherein the pharmaceutical composition includes:
peanut flour containing at least the amounts of Ara h1, Ara h2 and Ara h6 of the reference standard, and wherein a total characterized peanut protein amount is from 0.45 mg to 550 mg peanut protein;
one or more diluents in an amount of from 1% to 99% w/w of the pharmaceutical composition;
one or more lubricants in an amount of from 0.01% to 10% w/w of the pharmaceutical composition.

11. A method for treating peanut allergy in a subject, comprising:
selecting a subject having a peanut allergy;
orally administering to the subject a pharmaceutical composition identified according to claim 10.

12. The method of claim 10, further comprising comparing samples from one or more lots of peanut flour to determine the amounts of Ara h1, Ara h2 and Ara h6 in the samples.

13. A method for treating peanut allergy in a subject, comprising:
selecting a subject having a peanut allergy;
orally administering to the subject a pharmaceutical composition comprising:
peanut flour comprising 0.9 mg to 1100 mg peanut protein;
one or more diluents in an amount of from 1% to 99% w/w of the pharmaceutical composition; and
one or more lubricants in an amount of from 0.01% to 10% w/w of the pharmaceutical composition.

14. The method of claim 13, wherein the pharmaceutical composition is formulated for oral administration.

15. The method of claim 13, wherein the pharmaceutical composition is formulated as a capsule, a tablet, a mini-tablet, a powder, or a sprinkle.

16. The method of claim 13, wherein the pharmaceutical composition is formulated as a food product.

17. The method of claim 13, wherein the one or more diluents is selected from the group consisting of alginic acid and salts thereof; a cellulose derivative; microcrystalline dextrose; amylose; magnesium aluminum silicate; polysaccharide acids; bentonite; gelatin; polyvinylpyrrolidone/vinyl acetate copolymer; crosspovidone; povidone; starch; pregelatinized starch; tragacanth, dextrin, a sugar; dicalcium phosphate; a natural or synthetic gum; polyvinylpyrrolidone; larch arabogalactan; Veegum®; polyethylene glycol; waxes; sodium alginate; sodium starch glycolate; a cross-linked starch; a cross-linked polymer; a cross-linked polyvinylpyrrolidone; alginate; a clay; sodium starch glycolate; a natural sponge; a surfactant; a resin; citrus pulp; sodium lauryl sulfate; sodium lauryl sulfate in combination with starch; and combinations thereof.

18. The method of claim 13, wherein the one or more lubricants is selected from the group consisting of stearic acid, calcium hydroxide, talc, corn starch, sodium stearyl fumerate, alkali-metal and alkaline earth metal salts, waxes, boric acid, sodium benzoate, sodium acetate, sodium chloride, leucine, a polyethylene glycol (PEG), a methoxypolyethylene glycol, propylene glycol, sodium oleate, glyceryl benzoate, magnesium lauryl sulfate, sodium lauryl sulfate, and combinations thereof.

19. The method of claim 13, wherein the pharmaceutical composition is formulated in a dose of 0.9 mg to 1.1 mg, 9.0 mg to 11.0 mg 90 mg to 110 mg, 427.5 mg to 522.5 mg, 450 mg to 550 mg, or 900 mg to 1100 g of peanut protein.

20. The method of claim 13, wherein the pharmaceutical composition comprises peanut flour in a concentration from 7.2% to 16.5% w/w.

21. The method of claim 13, wherein the pharmaceutical composition is administered daily over a period of at least two weeks.

22. The method of claim 1, wherein the one or more diluents comprise 60% to 90% w/w of the pharmaceutical composition.

23. The method of claim 1, wherein the one or more diluents comprise 5% to 20% w/w of the pharmaceutical composition.

24. The method of claim 10, wherein the one or more diluents comprise 60% to 90% w/w of the pharmaceutical composition.

25. The method of claim 10, wherein the one or more diluents comprise 5% to 20% w/w of the pharmaceutical composition.

26. The method of claim 13, wherein the one or more diluents comprise 60% to 90% w/w of the pharmaceutical composition.

27. The method of claim 13, wherein the one or more diluents comprise 5% to 20% w/w of the pharmaceutical composition.

28. A method for treating a peanut allergy in a subject having a peanut allergy, comprising orally administering to the subject a pharmaceutical composition identified according to the method of claim 10.

29. A method for treating a peanut allergy in a subject having a peanut allergy, comprising:
orally administering to the subject a pharmaceutical composition comprising:
peanut flour comprising 0.45 mg to 1100 mg peanut protein;
one or more diluents in an amount of from 1% to 99% w/w of the composition; and
one or more lubricants in an amount of from 0.01% to 10% w/w of the composition.

30. The method of claim 29, wherein the peanut flour comprises 0.45 mg to 550 mg peanut protein.

31. The method of claim 29, wherein the pharmaceutical composition is administered daily over a period of at least two weeks.

32. The method of claim 29, wherein the pharmaceutical composition is formulated for oral administration.

33. The method of claim 29, wherein the pharmaceutical composition is formulated as a capsule, a tablet, a mini-tablet, a powder, or a sprinkle.

34. The method of claim 29, wherein the pharmaceutical composition is formulated as a food product.

35. The method of claim 29, wherein the pharmaceutical composition is formulated in a dose of 0.45 mg to 0.55 mg, 0.9 mg to 1.1 mg, 9.0 mg to 11.0 mg, 90 mg to 110 mg, 427.5 mg to 522.5 mg, 450 mg to 550 mg, or 900 mg to 1100 mg peanut protein.

36. The method of claim 29, wherein the pharmaceutical composition comprises peanut flour in a concentration from 7.2% to 16.5%.

37. The method of claim 29, wherein the one or more diluents comprise 60% to 90% w/w of the pharmaceutical composition.

38. The method of claim 29, wherein the one or more diluents comprise 5% to 20% w/w of the pharmaceutical composition.

* * * * *